United States Patent
Bloom et al.

(10) Patent No.: US 7,825,091 B2
(45) Date of Patent: Nov. 2, 2010

(54) MODIFICATION OF FEEDING BEHAVIOUR

(75) Inventors: Stephen Robert Bloom, Hampstead (GB); Mohammad Ali Ghatei, Ruislip (GB); Caroline Jane Small, London (GB); Catherine Louise Dakin, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 11/781,773

(22) Filed: Jul. 23, 2007

(65) Prior Publication Data

US 2008/0064636 A1 Mar. 13, 2008

Related U.S. Application Data

(62) Division of application No. 10/541,526, filed as application No. PCT/GB2004/000017 on Jan. 12, 2004, now abandoned.

(30) Foreign Application Priority Data

Jan. 10, 2003 (GB) ................................ 0300571.7

(51) Int. Cl.
*A61K 38/16* (2006.01)
(52) U.S. Cl. ....................................... 514/12
(58) Field of Classification Search ........................ None
See application file for complete search history.

(56) References Cited

U.S. PATENT DOCUMENTS

| | | |
|---|---|---|
| 3,773,919 A | 11/1973 | Boswell et al. |
| 4,002,531 A | 1/1977 | Royer |
| 4,175,122 A | 11/1979 | Lazarus |
| 4,179,337 A | 12/1979 | Davis |
| 4,220,653 A | 9/1980 | Vivino |
| 4,223,017 A | 9/1980 | Lazarus |
| 4,355,025 A | 10/1982 | Lazarus |
| 4,485,045 A | 11/1984 | Regen |
| 4,544,545 A | 10/1985 | Ryan et al. |
| 4,619,794 A | 10/1986 | Hauser |
| 4,698,327 A | 10/1987 | Nagarajan et al. |
| 4,701,441 A | 10/1987 | Kalra |
| 4,829,076 A | 5/1989 | Szilagyi et al. |
| 5,021,234 A | 6/1991 | Ehrenfeld |
| 5,026,685 A | 6/1991 | Boublik et al. |
| 5,122,614 A | 6/1992 | Zalipsky |
| 5,284,839 A | 2/1994 | Siren et al. |
| 5,349,052 A | 9/1994 | Delgado et al. |
| 5,428,128 A | 6/1995 | Mensi-Fattohi et al. |
| 5,432,156 A | 7/1995 | Matsuno et al. |
| 5,512,549 A | 4/1996 | Chen et al. |
| 5,574,010 A | 11/1996 | McFadden |
| 5,604,203 A | 2/1997 | Balasubramaniam |
| 5,635,503 A | 6/1997 | Poindexter et al. |
| 5,643,575 A | 7/1997 | Martinez et al. |
| 5,696,093 A | 12/1997 | Tseng et al. |
| 5,700,486 A | 12/1997 | Canal et al. |
| 5,728,396 A | 3/1998 | Peery et al. |
| 5,858,975 A | 1/1999 | Yano |
| 5,880,131 A | 3/1999 | Greenwald et al. |
| 5,889,016 A | 3/1999 | Bruce et al. |
| 5,912,227 A | 6/1999 | Croom et al. |
| 5,919,901 A | 7/1999 | Hu et al. |
| 5,936,092 A | 8/1999 | Shen |
| 5,939,380 A | 8/1999 | Wang |
| 5,965,392 A | 10/1999 | Hu et al. |
| 5,989,920 A | 11/1999 | Gerald et al. |
| 5,993,414 A | 11/1999 | Haller |
| 6,001,836 A | 12/1999 | Poindexter et al. |
| 6,001,970 A | 12/1999 | Cascieri et al. |
| 6,046,167 A | 4/2000 | Balasubramaniam |
| 6,048,900 A | 4/2000 | Connell et al. |
| 6,093,692 A | 7/2000 | Shen |
| 6,127,355 A | 10/2000 | Greenwald et al. |
| 6,140,354 A | 10/2000 | Dax et al. |
| 6,191,102 B1 | 2/2001 | DiMarchi et al. |
| 6,201,025 B1 | 3/2001 | Dax et al. |
| 6,218,408 B1 | 4/2001 | Marzabadi et al. |
| 6,225,330 B1 | 5/2001 | Marzabadi et al. |
| 6,225,445 B1 | 5/2001 | Shen et al. |
| 6,268,343 B1 | 7/2001 | Knudsen et al. |
| 6,316,203 B1 | 11/2001 | Gerald et al. |
| 6,340,683 B1 | 1/2002 | Marzabadi et al. |
| 6,348,472 B1 | 2/2002 | Poindexter et al. |
| 6,355,478 B1 | 3/2002 | Baez et al. |
| 6,372,743 B1 | 4/2002 | Darrow et al. |

(Continued)

FOREIGN PATENT DOCUMENTS

CA 2431800 6/2002

(Continued)

OTHER PUBLICATIONS

Adrian, et al., "Effect of peptide YY on gastric, pancreatic, and biliary function in humans," *Gastroenterology*, 89:494-499 (1985).
Bays, et al., "Current and investigational antiobesity agents and obesity therapeutic treatment targets", *Obes Res.*, 12(8):1197-211 (2004).
Cummings, et al., "A preprandial rise in plasma ghrelin levels suggests a role in meal initiation in humans", *Diabetes*, 50:1714-1719 (2001).
Dakin, et al., "Repeated ICV administration of oxyntomodulin causes a greater reduction in body weight gain than in pair-fed rats", *Am J Physiol Endocrinol Metab.*, 283(6):E1173-7 (2002).
Dakin, et al, "Oxyntomodulin inhibits food intake in the rat", *Endocrinilogy*, 142:4244-4250 (2001).

(Continued)

*Primary Examiner*—Andrew D Kosar
(74) *Attorney, Agent, or Firm*—Lando & Anastasi, LLP

(57) ABSTRACT

The present invention relates to compositions and methods for use in the prevention or treatment of excess weight in a mammal. The compositions comprise oxyntomodulin which is shown to reduce food intake and/or increase energy expenditure.

13 Claims, 29 Drawing Sheets

U.S. PATENT DOCUMENTS

| | | |
|---|---|---|
| 6,380,224 B1 | 4/2002 | Dax et al. |
| 6,391,877 B1 | 5/2002 | Islam et al. |
| 6,391,881 B2 | 5/2002 | Sit |
| 6,399,631 B1 | 6/2002 | Elliot et al. |
| 6,407,120 B1 | 6/2002 | Carpino et al. |
| 6,410,707 B2 | 6/2002 | Wagner |
| 6,410,792 B1 | 6/2002 | Connell et al. |
| 6,420,532 B1 | 7/2002 | Gerald et al. |
| 6,432,960 B2 | 8/2002 | Sit et al. |
| 6,436,091 B1 | 8/2002 | Harper |
| 6,444,675 B2 | 9/2002 | Sit |
| 6,447,743 B1 | 9/2002 | Devic |
| 6,447,753 B2 | 9/2002 | Edwards et al. |
| 6,458,924 B2 | 10/2002 | Knudsen |
| 6,583,111 B1 | 6/2003 | DiMarchi et al. |
| 6,586,403 B1 | 7/2003 | Mathison et al. |
| 6,608,098 B1 | 8/2003 | Nagase et al. |
| 6,620,910 B1 | 9/2003 | Calas et al. |
| 6,645,774 B1 | 11/2003 | Gerald et al. |
| 6,667,319 B2 | 12/2003 | Stamford et al. |
| 6,699,891 B1 | 3/2004 | Kawanishi et al. |
| 7,166,575 B2 | 6/2004 | Quay |
| 6,890,898 B2 | 5/2005 | Bachovchin et al. |
| 7,078,381 B2 | 7/2006 | Bachovchin et al. |
| 7,157,429 B1 | 1/2007 | Bachovchin et al. |
| 7,265,125 B2 | 9/2007 | Breu et al. |
| 7,396,809 B1 | 7/2008 | Lu et al. |
| 7,459,432 B2 | 12/2008 | Cowley et al. |
| 2001/0011071 A1 | 8/2001 | Knudsen et al. |
| 2001/0046956 A1 | 11/2001 | Hadcock |
| 2002/0141985 A1 | 10/2002 | Pittner et al. |
| 2002/0156010 A1 | 10/2002 | Lustig |
| 2004/0018975 A1 | 1/2004 | DiMarchi et al. |
| 2005/0070469 A1 | 3/2005 | Bloom et al. |
| 2005/0176630 A1 | 8/2005 | Cowley et al. |
| 2005/0176643 A1 | 8/2005 | Bridon et al. |
| 2006/0014678 A1 | 1/2006 | Cowley et al. |
| 2006/0171920 A1 | 8/2006 | Shecther |
| 2006/0189522 A1 | 8/2006 | Bloom et al. |
| 2008/0064636 A1 | 3/2008 | Bloom et al. |
| 2009/0181885 A1 | 7/2009 | Bloom |
| 2009/0209461 A1 | 8/2009 | Hecker et al. |

FOREIGN PATENT DOCUMENTS

| | | |
|---|---|---|
| CN | 1490333 | 4/2004 |
| DE | 32 18 121 | 11/1983 |
| EP | 0 036 676 | 9/1981 |
| EP | 0 052 322 | 5/1982 |
| EP | 0 058 481 | 8/1982 |
| EP | 0 088 046 | 9/1983 |
| EP | 0 102 324 | 3/1984 |
| EP | 0 133 988 | 3/1985 |
| EP | 0 142 641 | 5/1985 |
| EP | 0 143 949 | 6/1985 |
| EP | 0 267 050 | 5/1988 |
| EP | 0 401 384 | 12/1990 |
| EP | 0 619 332 | 10/1994 |
| EP | 0619332 | 10/1994 |
| EP | 0708179 | 4/1996 |
| EP | 0 795 562 | 9/1997 |
| EP | 0795562 | 9/1997 |
| EP | 0920864 | 11/1998 |
| EP | 0 955 314 | 11/1999 |
| EP | 1499277 | 1/2009 |
| JP | 60-007934 | 1/1985 |
| JP | 11-228447 | 8/1999 |
| JP | 2001-011095 | 1/2001 |
| WO | WO 80/01882 | 9/1980 |
| WO | WO 93/09227 | 5/1993 |
| WO | WO 93/19175 | 9/1993 |
| WO | WO 94/22467 | 10/1994 |
| WO | WO 95/06058 | 3/1995 |
| WO | 96/22783 | 8/1996 |
| WO | 97/37998 | 10/1997 |
| WO | 97/46579 | 12/1997 |
| WO | 98/20895 | 5/1998 |
| WO | WO 98/20885 | 5/1998 |
| WO | WO 98/20895 | 5/1998 |
| WO | 98/30231 | 7/1998 |
| WO | WO 98/32466 | 7/1998 |
| WO | 99/39702 | 8/1999 |
| WO | WO 99/43707 | 9/1999 |
| WO | WO 00/34236 | 6/2000 |
| WO | WO 00/42026 | 7/2000 |
| WO | WO 00/47219 | 8/2000 |
| WO | WO 00/59887 | 10/2000 |
| WO | WO 00/68197 | 11/2000 |
| WO | WO 00/78333 | 12/2000 |
| WO | WO 01/04156 | 1/2001 |
| WO | WO 01/14368 | 1/2001 |
| WO | WO 01/14368 | 3/2001 |
| WO | WO 01/14386 | 3/2001 |
| WO | WO 01/35988 | 5/2001 |
| WO | WO 01/51078 | 7/2001 |
| WO | 01/68699 | 9/2001 |
| WO | WO 01/66135 | 9/2001 |
| WO | WO 01/76631 | 10/2001 |
| WO | 01/87335 | 11/2001 |
| WO | WO 01/87335 | 11/2001 |
| WO | WO 01/89554 | 11/2001 |
| WO | WO 02/03978 | 1/2002 |
| WO | WO 02/47712 | 6/2002 |
| WO | WO 02/67918 | 6/2002 |
| WO | WO 02/066479 | 8/2002 |
| WO | WO 02/067918 | 9/2002 |
| WO | WO 03/022304 | 3/2003 |
| WO | 03/026591 | 4/2003 |
| WO | 03/057235 | 7/2003 |
| WO | 2004/062685 | 7/2004 |
| WO | 2005/035761 | 4/2005 |
| WO | WO 2005/118642 | 12/2005 |
| WO | WO 2006/082517 | 8/2006 |
| WO | 2006/095166 | 9/2006 |
| WO | 2006/34340 | 12/2006 |
| WO | 2007/056362 | 5/2007 |
| WO | 2007/100535 | 9/2007 |
| WO | 2007/146038 | 12/2007 |
| WO | 2008/003947 | 1/2008 |
| WO | 2008/071972 | 6/2008 |

OTHER PUBLICATIONS

Eng, et al., "Isolation and characterization of exendin-4, an exendin-3 analogue, from *Heloderma suspectum* venom. Further evidence for an exendin receptor on dispersed acini from guinea pig pancreas", *J Biol Chem*, 267:7402-7405 (1992).

English, "Food fails to suppress ghrelin levels in obese humans", *J Clin Endocrinol Metab*, 87:2984-87 (2002).

Ghatei et al., "Molecular forms of human enteroglucagon in tissue and plasma: plasma responses to nutrient stimuli in health and in disorders of the upper gastrointestinal tract", *J Clin Endocrinol Metab*, 57:488-495 (1983).

Kreymann, "Glucagon-like peptide-1 7-36: a physiological incretin in man", *Lancet*, 2:1300-1304 (1987).

Messer, "Vasopressin and Oxytocin", retrieved from http//www.neurosci.pharm.utoledo.edu/MBC3320/vasopressin.htm on Aug. 22, 2005.

"Oxyntomodulin", retrieved from http://www.glucagon.com/oxyntomodulin.htm>Mar. 3, 2001, on Aug. 30, 2006.

Parker, "Hormone Oxyntomodulin causes weight loss by Appetite reduction", retrieved from http//www.futurepundit.com/archives/002946.html, on Aug. 8, 2006.

Rudinger, "Characteristics of the amino acids as components of a peptide hormone sequence", In: Peptide Hormones, JA Parsons, Ed. pp. 1-7 (1976).

Schjoldager, et al., "Oxyntomodulin: a potential hormone from the distal gut. Pharmacokinetics and effects on gastric acid and insulin secretion in man" *Eur J Clin Invest.*, 18(5):499-503 (1988).

Senel and Hincal, "Drug permeation enhancement via buccal route: possibilities and limitations", *J Control Release*, 72(1-3):133-44 (2001).

Smilek, et al., "A single amino acid change in a myelin basic protein peptide confers the capacity to prevent rather than induce experimental autoimmune encephalomyelitis" *Proc Natl Acad Sci U S A.*, 88(21):9633-7 (1991).

Tatemoto, "Isolation and characterization of peptide YY (PYY), a candidate gut hormone that inhibits pancreatic exocrine secretion", *Proc. Natl. Acad. Sci.*, 79:2514-8 (1982).

The Wonders of Weight Loss, American Fitness, Jan./Feb., p. 18 (2006).

Uesaka, et al., "Glucagon-like peptide isolated from the eel intestine: effects on atrial beating", *J Exp Biol.*, 204(Pt 17):3019-26 (2001).

Voet and Voet, "Abnormal Hemoglobins", In: Biochemistry, $2^{nd}$ Edithion, pp. 235-241 (1995).

Wikosz and Bogner, "Transdermal drug delivery. Part 1: Current Status" In U.S. Pharmacist, retrieved from http//www.uspharmacist.com/index.asp?show=article&page=8_1061.htm on Aug. 29, 2006.

Wren, et al., "Ghrelin enhances appetite and increases food intake in humans", *J Clin Endocrinol Metab*, 86:5992-5 (2001).

Wynne, et al., "Subcutaneous oxyntomodulin reduces body weight in overweight and obese subjects: a double-blind, randomized, controlled trial", *Diabetes*, 54(8):2390-5 (2005).

Search Report dated Apr. 9, 2004 from International Application No. PCT/US02/31944.

International Preliminary Examination Report dated Jan. 28, 2005 from International Application No. PCT/US02/31944.

Search Report dated Sep. 19, 2003 from International Application No. PCT/GB03/00062.

Search Report dated Mar. 13, 2007 from International Application No. PCT/GB2006/002155.

Search Report dated Oct. 19, 2007 from International Application No. PCT/GB2007/002473.

Search Report dated May 21, 2008 from International Application No. PCT/GB2007/004779.

U.S. Appl. No. 60/256,216, Pittner et al., filed Dec. 14, 2000.

U.S. Appl. No. 60/324,406, Cowley et al., filed Sep. 24, 2001.

Abuchowski, "Cancer therapy with chemically modified enzymes. I. Antitumor properties of polyethylene glycol-asparaglnase conjugates", *Cancer Biochem. Biophys.*, 7(2):175-86 (1984).

Adrian, "Distribution and postprandial release of procine peptide YY", *J. Endocr.*, 113:11 (1987).

Adrian, "Human distribution and release of a putative new gut hormone, peptide yy", *Gastroenterology*, 89:1070-1077 (1985).

Adrian, "Peptide YY Abnormalities in Gastrointestinal Diseases", *Gastroenterology*, 90:379 (1986).

Adrian, "Effect of Peptide YY on Gastric, Pancreatic, and Biliary Function in Humans", *Experimental Physiology*, 89:494 (1985).

Adrian, "Elevated Plasma Peptide YY in Human Neonates and Infants," *Pediatric Research*, 20(12) (1986).

Adrian, "Plasma Peptide YY (PYY) in Dumping Syndrome", *Digestive Diseases & Sciences*, 30(12):1145 (1985).

Adrian, "Release of peptide YY (PYY) after resection of small bowel, colon, or pancreas in man," *Surgery*, 101(6), 715 (987).

Allen, "Effects of Peptide YY and Neuropeptide Y on Gastric Emptying in Man", Digetsion, 30:255 (1984).

Allen, "Radioimmunoassay of neuropeptide y", *Regulatory Peptides*, 8:61-70 (1984).

Allen, "Two novel related peptides, neuropeptide Y (NPY) and Peptide YY (PYY) inhibit the contraction of the electrically stimulated mouse vas deferens", *Neuropeptides*, 3 71, (1982).

Asakawa, "Mouse pancreatic polypeptide modulates food intake, while not influencing anxiety in mice", *Peptides*, 20:1445 (1999).

Assuncao, "Weight gain management in patients with schizophrenia during treatment with olanzapine in association with nizatidine", *Rev. Bras. Psiquiatr.*, 28(4):270-276 (2006).

Bagnol, et al., "Anatomy of an Endogenous Antagonist: Relationship between Agouti-Related Protein and Proopiomelanocortin in Brain," *J. Neurosci. (Online)*, 19, RC26. (1999).

Balasubramaniam, "Syntheses and receptor affinities of partial sequences of peptide yy (pyy)", *Pept. Res.*, 1(1):32-5 (1998).

Barlow and Dietz, "Obesity evaluation and treatment: Expert Committee recommendations. The Maternal and Child Health Bureau, Health Resources and Services Administration and the Department of Health and Human Services", *Pediatrics*, 102:E29 (1998).

Barrachina, "Leptin-induced decrease in food intake is not associated with changes in gastric emptying in lean mice", *Am. J. Physiol.*, 272:R1007-11 (1997).

Barsh, "Genetics of body-weight regulation," *Nature*, 404, 644 (2000).

Batterham, "Gut hormone PYY(3-36) physiologically inhibits food intake", *Nature*, 418(6898):650-4 (2002).

Bays, "Current and investigational antiobesity agents and obesity therapeutic treatment targets", *Obes Res.*, 12(8):1197- 211 (2004).

Beck-Sickinger and Jung, "Structure-activity relationships of neuropeptide y analogues with respect to $Y_1$ and $Y_2$ receptors", *Biopolymers*, 37:123-142 (1995).

Beer, "The effect of a 72-h fast on plasma levels of pituitary, adrenal, thyroid, pancreatic and gastrointestinal hormones in healthy men and women," *J. Endocr.*, 120,337 (1989).

Berglund, "Binding Properties of Three Neuropeptide Y Receptor Subtypes from Zebrafish: Comparison with Mammalian Y1 Receptors", *Biochem. Pharmacol.*, 60(12):1815-22, (2000).

Bowie, "Deciphering the message in protein sequences: tolerance to amino acid substitutions", *Science*, 247:1306-1310 (1990).

Broberger, "Subtypes Y1 and Y2 of the neuropeptide Y receptor are respectively expressed in pro-opiomelanocortin- and neuropeptide-Y-containing neurons of the rat hypothalamic arcuate nucleus", *Neuroendocrinology*, 66:393-408, 1997.

Buchwald, "Long-term, continuous Intravenous heparin administration by an implantable infusion pump in ambulatory patients with recurrent venous thrombosis", *Surgery*, 88:507-516 (1980).

Buse, "Effects of exenatide (exendin-4) on glycemic control over 30 weeks in sulfonylurea-treated patients with type 2 diabetes", *Diabetes Care*, 27(11):2628-2635 (2004).

Butler, "Melanocortin-4 receptor is required for acute homeostatic responses to increased dietary fat", *Nature Neuroscience*, 4:605-611(2001).

Butler, "A Unique Metabolic Syndrome Causes Obesity in the Melanocortin-3 Receptor-Deficient Mouse", *Endocrinology*, 141,3518 (2000).

Cabrele, "Molecular characterization of the ligand—receptor interaction of the neuropeptide Y family", *J. Pept. Sci.*, 6(3):97-122 (2000).

Calam, "Regional Differences in Concentrations of Regulatory Peptides in Human Colon Mucosal Biopsy", *Digestive Diseases & Sciences*, 34(8)1193 (1989).

Caliceti, "Biopharmaceutical properties of uricase conjugated to neutral and amphiphilic polymers", *Bioconjug. Chem.*, 10(4):638-46 (1999).

Campbell, "Oxygen-dependent K+ influxes in Mg2+-clamped equine red blood cells", *J. Physiol. (Lond.)* 515, 439. (1999).

Campfield, "Recombinant Mouse OB Protein: Evidence for a Peripheral Signal Linking Adiposity and Central Neural Networks", *Science*, 269:546 (1995).

Chelikani, "Intravenous infusion of peptide YY(3-36) potently inhibits food intake in rats", *Endocrinology*, 146(2):879-88 (2005).

Clapham, "Anti-obesity drugs: a critical review of current therapies and future opportunities", *Pharmacol. Ther.*, 89(1):81-121 (2001).

"Clinical Guidelines on the Identification, Evaluation, and treatment of Overweight and Obesity in Adults—The Evidence Report", National Institutes of health, *Obesity Research*, 6(Suppl 2):51S-209S (1998).

Cohen, "Oxyntomodulin suppresses appetite and reduces food intake in humans", *J. Clin. Endocrinol. Metab.*, 88(10):4696-4701 (2003).

Comuzzie, "A major quantitative trait locus determining serum leptin levels and fat mass is located on human chromosome 2", *Nature Genetics*, 15:273 (1997).

Cone, "The Central Metanocortin System and Energy Homeostasis," *Trends Endoerinol. Metab.*, 10,211(1999).
Cowley, "Leptin activates anorexigenic POMC neurons through a neural network in the arcuate nucleus", *Nature*, 411:480-484 (2001).
Cowley, "Integration of NPY, AGRP, and Melanocortin Signals in the Hypothalamic Paraventricular Nucleus: Evidence of a Cellular Basis for the Adipostat," *Neuron*, 24, 155 (1999).
Cox and Randich, "Enhancement of feeding suppression by PYY(3-36) in rats with area postrema ablations", *Peptides*, 25(6):985-9 (2004).
Csiffart, "Neuropeptide Y Innerveration of ACTH-Immunoreactive neurons in the arcuate nucleus of rats: a correlated light and electron microscopic double immunolabeling study", *Brain Research*, 506:215-222 (1990).
D. Voet and J.G. Voet, Biochemistry, $2^{nd}$ Edition, pp. 235-241 (1995).
Dakin, "Oxyntomodulin inhibits food intake in the rat", *Endocrinology*, 142:4244-4250 (2001).
Dakin, "Peripheral oxyntomodulin reduces food intake and body weight gain in rats", *Endocrinology*, 145:2687-2695 (2004).
Dakin, "Repeated ICV administration of oxyntomodulin causes a greater reduction in body weight gain than in pair-fed rats", *Am. J. Physiol. Endocrinat. Metab.*, 283:E1173-E1177(2002).
Delgado, "The uses and properties of PEG-linked proteins", *Crit. Rev. Ther. Drug Carrier Syst.*, 9(3-4):249-304 (1992).
Donckier, "Age-related changes in regulatory peptides in rectal mucosa", *Acta Gastro-Enterologica Belgica*, vol. L, 405 (1987).
Doods, "Pharmacological characterization of the selective nonpeptide neuropeptide Y Y1 receptor antagonist BIBP 3226", *J. Pharmecol. Exp. Ther.* 275(1):136-42 (1995).
Dreborg, "Immunotherapy with monomethoxypolyethylene glycol modified allergens", *Crit. Rev. Ther. Drug Carrier Syst.*, 6(4):315-65 (1990).
Dumont, "Characterization of a selective neuropeptide Y/peptide YY Y2 receptor radioligand", *Society for Neuroscience Abstracts*, 19:726 (1993).
Eberlein, "A new molecular form of PYY: structural characterization of human PYY(3-36) and PYY(1-36)", *Peptides*, 10:797-803 (1989).
Edwards, "Exendin-4 reduces fasting and postprandial glucose and decreases energy intake in healthy volunteers", *Am. J. Physiol. Endocrinol. Metab.*, 281: E155-E166 (2001).
Ekblad, "Distribution of pancreatic polypeptide and peptide YY," *Peptides*, 23, 251 (2002).
Elias, Leptin Differentially Regulates NPY and POMC Neurons Projecting to the Lateral Hypothalamic Area, *Neuron*, 23, 775 (1999).
Eng, "Isolation and characterization of exendin-4, an exendin-3 analogue, from Heloderma suspectum venom. Further evidence for an exendin receptor on dispersed acini from guinea pig pancreas", *J. Biol. Chem.*, 267(11):7402-5 (1992).
Epstein, "Biological activity of liposome-encapsulated murine interferon gamma is mediated by a cell membrane receptor", *Proc. Natl. Acad. Sci. U.S.A.* 82:3688-3692 (1985).
Fan, et al., "Role of melanocortinergic neurone in feeding and the agouti obesity syndrome," *Nature*, 385,165 (1997).
Farooqi, "Effects of Recombinant Leptin Therapy in a Child with Congenital Leptin Deficiency", *New England J. Med.*, 341:879 (1999).
Ferri, "Intramural distribution of regulatory peptides in the sigmoid-recto-anal region of the human gut", *Gut*, 29,762 (1988).
Fiiebl, et al., "Peptide YY in Diabetest Treated Chronically with an Intestinal Gluosidase Inhibitor," *Klinische Wochen-schrift*, 66985 (1988).
Fournier, "Conformational and biological studies of neuropeptide Y analogs containing structural alterations", *Mol. Pharmacol.*, 45(1):93-101 (1994).
Francis, "PEGylation of cytokines and other therapeutic proteins and peptidei: the importance of biological optimisation of coupling techniques", *Int. J. Hematol.*, 68(1):1-18 (1998).
Fried, "Temporal Relationships of Cholecystokinin Release, Pancreatobiliary Secretion, and Gastric Emptying of a Mixed Meal", *Gastroenterology*, 95:1344 (1988).

Fuessl, "The effect of a long-acting somatostatin analogue (SMS 201-995) on intermediary metabolism and gut hormones after a test meal in normal subjects", *Aliment. Pharmacol. Therap.*, 1:321 (1987).
Garrow, "Does cimetidine cause weight loss?", *BMJ.*, 306(6885):1084 (1993).
Gehlert, "Multiple receptors for the pancreatic polypeptide (pP-fold) family: Physiological implications", *Proc. Soc. Exp. Biol. Med.*, 218:7-22 (1998).
Ghatei, "Fermentable dietary fibre, intestinal microflora and plasma hormones in the rat", *Clinical Science*, 93:109 (1997).
Glaum, "Leptin, the Obese Gene Product, Rapidly Modulates Synaptic Transmission in the Hypothalamus", *Mol. Pharmacol.*, 50: 230 (1996).
Goodlad, "Effects of an elemental diet, inert bulk and different types of dietary fibre on the response of the intestinal epithelium to refeeding in the rate and relationship to plasma gastrin, enteroglucagon, and PYY concentrations", *Gut*, 28:171 (1987).
Goodlad, "Glucagon 1-21 Reduces Intestinal Epithelial Cell Proliferation in Parenterally Fed Rats", *Experimental Physiology*, 76:943 (1991).
Goodlad, "Is Peptide YY Trophic to the Intestinal Epithelium of Parentally Fed Rats?", *Digestion*, 46(82):177 (1990).
Goodlad, "Proliferative effects of 'fibre' on the intestinal epithelium: relationship to gastrin, enteroglucagon and PPY", *Gut*, 28(S1):221 (1987).
Goodlad, "Insulin and Intestinal Epithelial Cell Proliferation", *Experimental Physiology*, 78 697 (1993).
Goodlad, "Does the response of the intestinel epithelium to keratinocyte growth factor vary according to the method of administration?", *Regulatory Peptides*, 87, 83 (2000).
Goodlad, "Plasma Enteroglucagon, Gastrin and Peptide YY in Conventional and Germ-Free Rats Refed with a Fibre-Free or Fibre-Supplemented Diet", *Quarterly Journal of Experimental Physiology*, 74:437 (1989).
Graffner, "Effects of Physiological Increases of Plasma Noradrenaline on Gastric Acid Secretion and Gastrointestinal Hormones", *Digestive Diseases & Sciences*, 32(7):715 (1987).
Grandt, "Characterization of two forms of peptide YY, PYY(1.36) and PYY(3-36), in the rabbit", *Regul. Pept.*, 51:151-159 (1994).
Grandt, "Neuropeptide Y 3-36 is an endogenous ligand selective for Y2 receptors", *Peptides*, 15(5):815-820 (1994).
Grandt, "Two molecular forms of peptide YY (PYY) are abundant in human blood: characterization of a radloimmunoassay recognizing PYY 1-36 and PYY 3-36", *Regulatory Peptides*, 67(1):33-7 (1996).
Grieco, et al., "D-Amino Acid Scan ofr-Melanocyte-Stimulating Hormone: Importance of Trp8 on Human MC3 Receptor Selectivity," *J. Med. Chem.*, 43:4998 (2000).
Grove, "Neuropeptide y y5 receptor protein in the cortical/limbic system and brainstem of the rat: expression on g-aminobutyric acid and corticotropin-releasing hormone neurons", *Neuroscience*, 100(4):731-740 (2000).
Grundemar, "Ligand binding and functional effects of systematic double D-amino acid residue substituted neuropeptide Y analogs on Y1 and Y2 receptor types", *Regulatory Peptides*, 62:131-136 (1996).
Hagan, "Peptide YY: a key mediator of orexigenic behavior," *Peptides*, 23, 377 (2002).
Hager, "A genome-wide scan for human obesity genes reveals a major susceptibility locus on chromosome 10", *Nature Genetics*, 19:155 (1998).
Hakansson, "Leptin receptor immunoreactivity in chemically defined target neurons of the hypothalamus", *J. Neurosci.*, 18:559-72 (1998).
Hammer, "Pituitary-Specific and Hormonally Regulated Gene Expression Directed by the Rat Prooplomelanocortin Promoter in Transgenic Mice," *Mol. Endocrin.*, 4(11):1689 (1990).
Harding, "Identification and Characterization of the Emetic Effects of Peptide YY", *Peptides*, 10:21 (1989).
Haynes, "Interactions Between the Melanocortin System and Leptin in Control of Sympathetic Nerve Traffic", *Hypertension*, 33(1), 542. (1999).
Haynes, et al., "Receptor-mediated Regional Sympathetic Nerve Activation by Leptin", *J. Clin. Invest.*, 100:270 (1997).

Heisler, "Activation of Central Melanocortin Pathways by Fenfluramine", *Science*, 297(5581):609 (2002).

Hoffman, "c-Fos and Related Immediate Early Gene Products as Markers of Activity in Neuroendocrine Systems", *Front. Neuroendocrinol.*, 14:173 (1993).

Holst, "Enteroglucagon", *Ann. Rev. Physiol.*, 59:257-271 (1997).

Holz and Habener, "Black widow spider alpha-latrotoxin: a presynaptic neurotoxin that shares structural homology with the glucagon-like peptide-1 family of insulin secretagogic hormones", *Comp. Biochem. Physiol. Part B* 121:177-184 (1998).

Horvath, "Gabaergic and Catecholaminergic Innervation of Mediobasal Hypothalamic PEndorphin Cells Projecting to the Medial Preoptic Area", *Neurosciences*, 51:391(1992).

Horvath, "Heterogeneity in the neuropeptide Y-contalnin neurons of the rat arcuate nucleus: GABAergic and non-GABAergic subpopulations", *Brain Res.*, 756, 283. (1997).

Hwang, "Hepatic uptake and degradation of unilamellar sphingomyelin/cholesterol liposomes: A kinetic study", *Proc. Natl. Acad. Sci. U.S.A.*, 77:4030-4034 (1980).

Iyengar, et al., "Characterization of Neuropeptide Y-Induced Feeding in Mice: Do Y1-Y6 Receptor Subtypes Mediate Feeding?" *J. of Pharmacology and Experimental Therapeutics*, 289(2),1031 (1999).

Jequier, "Energy, obesity, and body weight standard", *Am. J. Clin. Nutr.*, 45:1035-47 (1987).

Kalra, "Interacting appetite-regulating pathways in the hypothalamic regulation of body weight", *Endocr. Rev.*, 20:68-100 (1999).

Kanatani, "L-152,804: Orally active and selective neuropeptide Y Y5 receptor antagonist", *Biochem. Biophys. Res. Commun.*, 272(1):169-73 (2000).

Keire, et al., "Primary structures of PYY, [Pro34]PYY, and PYY-(3-36) confer different conformations and receptor selectivity," *Am. J. Physiol. Gastrointest. Liver Physiol.*, 279, G126 (2000).

Kelly, "Qpioids Hyperpolarize p-Endorphin Neurons via JI-Receptor Activation of a Potassium Conductance", *Neuroendocrinology*, 52:268 (1990).

Kenchaiah, "Obesity and the risk of heart failure", *N. Engl. J. Med.*, 347(5):305-13 (2002).

Kim, "Hypothalamic localization of the feeding effect of agouti-related peptide and alpha-melanocyte-stimulating hormone", *J. Clin. Invest.*, 105:1005-11 (2000).

Kim, "The central melanocortin system affects the hypothalamopituitary thyroid axis and may mediate the effect of leptin", *Diabetes*, 49:177-82 (2000).

Kimmel, "Isolation and characterization of chicken insulin", *Endocrinology*, 83:1323-30 (1968).

King, "Regulation of neuropeptide Y release by neuropeptide Y receptor ligands calcium channel antagonists in hypothalamic slices", *J. Neurochem.*, 73:641-6 (1999).

Kirby, "Neuropeptide Y: Y1 and Y2 affinities of the complete series of analogues with single D-residue substitutions", *J. Med. Chem.*, 38:4579-86 (1995).

Kirby, "Y1 and Y2 receptor selective neuropeptide Y analogues: Evidence of a Y1 receptor subclass", *J. Med. Chem.*, 36:3802-08 (1993).

Kirby, "Defining Structural Requirements for Neuropeptide Y Receptors Using Truncated and Conformationally Restricted Analogues", *J. Med. Chem.*, 36:385 (1983).

Kopelman, "Obesity as a medical problem", *Nature*, 404:635-43 (2000).

Kreymann, "Developmental Patterns of Glucagon - Like Peptide-I-(7-36) Amide and Peptide-YY in Rat Pancras and Gut", *Endocrinology*, 129:1001 (1991).

Krode, "Implications of Proopiomelanocortin (pOMC) Mutations in Humans: The POMC Deficiency Syndrome", *Trends Endocrinol. Metab.*, 11(1):15 (2000).

Krode, "Severe early-onset obesity, adrenal insufficiency and red-hair pigmentation caused by POMC mutations in humans", *Nature Genetics*, 19:155 (1998).

Langer, "Biocompatibility of polymeric delivery systems for macromolecules", *J. Biomed. Mater. Res.*,15:167-277 (1981).

Langer, "Controlled release of macromolecules", *Chem. Tech.*, 12:98-105 (1982).

Langer, "New methods of drug delivery", *Science*, 249:1527-1533 (1990).

Leban, "Novel modified carboxy terminal fragments of neuropeptide Y with high affinity for Y2-type receptors and potent functional antagonism at a Y1-type receptor", *J. Med. Chem.*, 38:1150-57 (1995).

Liu, "DNA elements with AT-rich core sequences direct pituitary cell-specific expression of the pro-opiomelanocortin gene in transgenic mice", *Biochem. J.*, 312, 827 (1995).

Liu, "Identification of DNA Elements Cooperatively Activating Proopiomelanocortin Gene Expression in the Pituitary Glands of Transgenic Mice", *Mol & Cell Biol.*, 12(9):3978 (1992).

Liu, "Synthetic peptide YY analog binds to a cell membrane receptor and delivers fluorescent dye to pancreatic cancer cells", *J. Gastrointest Surg.*, 5(2):147-52 (2001).

Low, et al., "Post-translational Processing of Proopiomelanocortin (pOMC) in Mouse Pituitary Melanotroph Tumors Induced by a POMC-Simian Virus 40 Large T Antigen Transgene," *J.BioL Chem.*, 268 (33), 24967 (1993).

Lundberg and Modin, "Inhibition of sympathetic vasoconstriction in pigs in vivo by the neuropeptide Y-Y1 receptor antagonist BIBP 3226", *Br. J. Pharmacol.*, 116(7):2971-82 (1995).

Lyznicki, "Obesity: assessment and management in primary care", *Am. Fam. Phys.*, 63:2185-96 (2001).

Lyznicki, "Obesity: Assessment and Management in Primary Care", *Amer. Family Phys.*, 63(11):2185 (2001).

Malaisse-Lagae, "Pancreatic polypeptide: A possible role in the regulation of food intake in the mouse. Hypothesis", *Experientia*, 33(7):915 (1977).

Malik, "Polyethylene glycol (PEG)-modified granulocyte-macrophage colony-stimulating factor (GM-CSF) with conserved biological activity", *Exp. Hematol.*, 20(8):1028-35 (1992).

Malmstrom, "Existence of both neuropeptide Y, Y1 and Y2 receptors in pig spleen evidence using subtype-selective antagonists in vivo", *Life Sci.*, 69(17):1999-2005 (2001).

Malmstrom, "Pharmacology of H 394/84, a dihydropyridine neuropeptide Y Y1 receptor antagonist, in vivo", *Eur. J. Pharmacol.*, 418(1-2):95-104 (2001).

Marks, et al., "Role of the Central Melanocortin System in Cachexia," *Cancer Research*, 61:1432 (2001).

Massie, "Obesity and heart failure—risk factor or mechanism?", *N. Engl. J. Med.*, 347:358 (2002).

McGowan and Bloom, "Peptide YY and appetite control", *Curr. Opin. Pharmacol.*, 4(6):583-8 (2004).

McNeely, "Sibutramine. A review of its contribution to the management of obesity", *Drugs*, 56(6)1093-1124 (1998).

Melagros, "Release of vasodilator, but not vasoconstrictor, neuropeptides and of enteroglucagon by intestinal ischaemia/reperfusion in the rat", *Gut*, 35:1701 (1994).

Messer, "Vasopressin and Oxytocin", web documents updated Apr. 3, 2000; <http://www.neurosci.pharm.utoledo.edu/MBC3329/vassopressin.htm>.

Moran, "Cholecystokinin and satiety: Current perspectives", *Nutrition*, 16:858-865 (2000).

Moran, "Peptide YY(3-36) inhibits gastric emptying and produces acute reductions in food intake in rhesus monkeys", *Am. J. Physiol. Regul. Integr. Comp. Physiol.*, 288(2):R384-8 (2005).

Morgan, "Inhibition of glucose stimulated insulin secretion by neuropeptide Y is mediated via the YI receptor and inhibition of adenylyl cyclase in RIN 5AH rat insulinoma cells", *Diabetologia*, 41:1481 (1998).

Morgan, "Reduced NPY Induced Feeding in Diabetic but not Steroid-Treated Rats: Lack of Evidence for Changes in Receptor Number or Affinity", *J. of Neuroendocrinology*, 8:283 (1996).

Morpurgo, "Covalent modification of mushroom tyrosinase with different amphiphic polymers for pharmaceutical and biocatalysis applications", *Appl. Biochem. Biotechnol.*, 56(1):59-72 (1996).

National Institutes of Health, National Heart, Lung, and Blood Institute (NHLBI), "Clinical Guidelines on the Identification, Evaluation, and Treatment of Overweight and Obesity in Adults—The Evidence Report, National Institutes of Health", *Obes. Res.*, 6 (suppl. 2):51S-209S (1998).

Naveilhan, "Normal feeding behavior r, body weight and leptin response require the neuropeptide Y Y2 receptor", *Nature Medicine*, 5(1):1188 (1999).
Naveilhan, "Attenuation of hypercholesterolemia and hyperglycemia in ob/ob mice by NPY Y2 receptor ablation," *Peptides*, 23(6):1087 (2002).
Navelihan, et al., "Distinct roles of the Y1 and Y2 receptors on neuropeptide Y-induced sensitization to sedation," *J. Neurochem.*, 78,1201 (2001).
Nightingale, "Gastrointestinal hormones in short bowel syndrome. Peptide YY may be the 'colonic brake' to gastric emptying", *Gut*, 39:267 (1996).
Okada, Abstract 520, 7- Meeting of Endocrine Society (1993).
"Oxyntomodulin" Internet Document http://www.glucagon.com/oxyntomodulin.htm> Mar. 13, 2001 2 pages, accessed Aug. 30, 2006.
Parker, Internet Document http://www.futurepundit.com/archives/002946.html> Aug. 17, 2005, accessed Aug 29, 2006.
Pedersen-Bjergaard, "Influence of meal composition on postprandial peripheral plasma concentrations of vasoactive peptides in man", *Scand. J. Clin. Lab. Invest.*, 56:497-503 (1996).
Pittner, "Effects of PYY[3-36] in rodent models of diabetes and obesity", *Int. J. Obes. Relat. Metab. Disord.*, 28(8):963-71 (2004).
Playford, "Effects of peptide YY on the human cardiovascular system: reversal of responses to vasoactive intestinal peptide", *Am. J. Physiol.*, 263:E740 (1992).
Playford, "Preliminary report: role of peptide YY in defence against diarrhea", *The Lancet*, 335, 1555 (1990).
Playford, "Comparison of the Effects of Transforming Growth Factor a and Epidermal Growth Factor on Gastrointestinal Proliferation and Hormone Release", *Digestion* 57:362 (1996).
Potter, "A novel neuropeptide Y analog, N-acetyl[Leu28, Leu31]neuropeptide Y-(24-36), with functional specificity for the presynaptic (Y2) receptor", *Eur. J. Pharmacol.*, 267(3):253-262 (1994).
Powis, "Leptin depolarizes rat hypothalamic paraventricular nucleus neurons", *Am. J. Physiol.*, 274 R1468 (1998).
Raben, "The reproducibility of subjective appetite scores", *Br. J. Nutr.*, 73:517-530 (1995).
Rasmussen, "Cimetidine suspension as adjuvant to energy restricted diet in treating obesity", *BMJ*, 306(6885):1093-1096 (1993).
Rissanen, "Risk of disability and mortality due to overweight in a Finnish population", *British Med. J.*, 301:835-837 (1990).
Rist, "The bioactive conformation of neuropeptide Y analogues at the human Y2-receptor", *Eur. J. Biochem.*, 247:1019-1028 (1997).
Rossi and Bloom, "Central Nervous System Neuropeptides Involved in Obesity", in *Handbook of Experimental Pharmacology*, pp. 313-341; eds. D.H. Lockwood and T.G Heffner, Springer, New York, (2000).
Rubinstein, "Rat and Mouse Proopiomelanocortin Gene Sequences Target Tissue-Specific Expression to the Pituitary Gland but not to the Hypothalamus of Transgenic Mice", *Neuroendocrinology*, 58:373 (1993).
Rudinger, In: Peptide Hormones, JA Parsons, Ed. (1976) 1-7.
Sarson, "Gut hormone changes after jejunoileal (JIB) or biliopancreatic (BPB) bypass surgery for morbid obesity", *Int. J. Obes.*, 5:471-480 (1981).
Saudek, "A preliminary trial of the programmable implantable medication system for insulin delivery", *N. Engl. J. Med.*, 321:574 (1989).
Savage, "Effects of peptide YY (PYY) on mouth to caecum intestinal transit time and on the rate of gastric emptying in healthy volunteers", *Gut*, 28:166 (1987).
Savage, "Is raised plasma peptide YY afer intestinal resection in the rate responsible for the trophic response?", *Gut*, 26:1353 (1985).
Schjoldager, "Oxyntomodulin: a potential hormone from the distal gut. Pharmacokinetics and effects on gastric acid and insulin secretion in man", *Eur. J. Clin. Invest.*, 18(5):499-503 (1988).
Schober, "The neuropeptide Y Y1 antagonist, 1229U91, a potent agonist for the human pancreatic polypeptide-preferring (NPY Y4) receptor", *Peptides*, 19(3):537-42 (1998).
Schutz, "Exercise and postprandial thermogenesis in obese women before and after weight loss", *Am. J. Clin. Nutr.*, 45(6):1424-32 (1987).
Schwartz, "Central nervous system control of food intake", *Nature*, 404:661-671(2000).
Sefton, "Implantable pumps", *CRC Crit. Ref. Biomed. Eng.*, 14:201 (1987).
Senel, "Drug permeation enhancement via buccal route: possibilities and limitations," *J. Control Release*, 72(1-3):133-144 (2001).
Sheikh "Neuropeptide Y and peptide YY: major modulators of gastrointestinal blood flow and function", *Am. J. Physiol.*, 261:G701-15 (1991).
Sherwood, "The origin and function of the pituitary adenylate cyclase-activating polypeptide (PACAP)/glucagon superfamily", *Endocrine Reviews*, 21(6):619-670 (2000).
Shiraishi, et al., "Leptin Effects on Feeding-Related Hypothalamic and Peripheral Neuronal Activities in Normal and Obese Rats," *Nutrition*, 15,576 (1999).
Sidman, "Controlled release of macromolecules and pharmaceuticals form synthetic polypeptides based on glutamic acid", *Biopolymers*, 22:547-556 (1983).
Simanowski, "Effects of Acute and Chronic Ethanol Administration on the Gastrointestinal Hormones Gastrin, Enteroglucagon, Pancreatic Glucagon and Peptide YY in the rat" *Digestion*, 42:167 (1989).
Slugg, "Effect of the JI-Opiod Against DAMGO on Medial Basal Hypothalamic Neurons in Beta-Endorphin Knockout Mice", *Neuroendocrinology*, 72:208 (2000).
Small, "Peptide analogue studies of the hypothalamic neuropeptide Y receptor mediating pituitary adrenocorticotrophic hormone release", *Proc. Natl. Acad. Sci. U.S.A.*, 94:11686-91 (1997).
Smilek, "A single amino acid change in a myelin basic protein peptide confers the capacity to prevent rather than induce experimental autoimmune encephalomyelitis", *Proc. Natl. Acad. Sci. U.S.A.*, 1:88(21):9633-7 (1991).
Soderberg, "Zebrafish genes for neuropeptide Y and peptide YY reveal origin by chromosome duplication from an ancestral gene linked to the homeobox cluster", *J. Neurochem.*, 75:908-18 (2000).
Soll, "Novel analogues of neuroppeitde Y with a preference for the YI-receptor", *Eur. J. Biochem.*, 268(10):2828-37 (2001).
Spanswick, "Leptin inhibits hypothalamic neurons by activation of ATP-sensitive potassium charmed," *Nature*, 390, 521 (1997).
Spiller, "Further characterisation of the 'ileal brake' reflex in man—effect of ileal infusion of partial digests of fat, protein, and starch on jejunal motility and release of neurotensin, enteroglucagon, and peptide YY", *Gut*, 29:1042 (1988).
Stoa-Birketvedt, "Cimetidine reduces weight and improves metabolic control in overweight patients with Type 2 diabetes", *International Journal of Obesity Relat. Metab. Disord.*, 22(11):1041-1045 (1998).
Stoa-Birketvedt, "Effect of cimetidine suspension on appetite and weight in overweight subjects", *BMJ*, 306(6885):1091-1093 (1993).
Stoa-Birketvedt, "$H_2$-receptor antagonist reduces food intake and weight gain in rats by non-gastric acid secretory mechanisms", *Scandinavian Physiological Society*, 161(4):489-494 (1997).
Tarling, "A model gastric emptying using paracetamol absorption in intensive care patients", *Intensive Care Med.*, 23:256-260 (1997).
Tatemoto, "Neuropeptide Y: Complete amino acid sequence of the brain peptide", *Proc. Natl. Acad. Sci. U.S.A.*, 79:5485-9 (1982).
"The Wonders of Weight Loss", *American Fitness*, Jan./Feb. p. 18 (2006).
Tsukada, "Functional Analysis of the Cell-Specific Enhancer in the Human Proopiomelanocortin Gene by B-Galactosidase Histochemical Staining", *DNA and Cell Biol.*, 13(7):755 (1994).
Uesaka, "Glucagon-like peptide isolated from the eel intestine: effects on atrial beating", *Journal of Experimental Biology*, 204:3019-3026 (2001).
Verma, "Human fos gene", *Cold Spring Harb. Symp. Quant. Biol.*, 51:949-58 (1986).
Vorobjev, "Oligonucleotide conjugated to linear and branched high molecular weight polyethylene glycol as substrates for RNase H", *Nucleosides & Nucleotides*, 18(11-12):2745-50 (1999).
Walan and Strom, "Metabolic consequences of reduced gastric acidity", Scand. J. Gastroenterol. Suppl., 111:24-30 (1985).
Walker, "Neuropetide Y modulates Neurotransmitter Release and $Ca^{2+}$ Currents in Rat Sensory Neurons", *J. Neuroscience*, 8:2438-2446 (1988).

Wang and Hanson, "Parenteral Formulations of Proteins and Peptides: Stability and Stabilizers", *Journal of Parenteral Science and technical Technology*, 42:S4-S26 (1988).

Wardlaw, "Obesity as a Neuroendocrine Disease: Lessons to be Learned from Proopiomelanocortin and Melancortin Receptor Mutations in Mice and Men," *J. Clin. Endocrin. & Metab.*, 86(4):1442 (2001).

Wilkosz, "Transdermal Drug delivery", *U.S. Pharmacist, A jobson publication*, 28(4):1-15(2003).

Wolfe and Morton, "Weighing in on bariatric surgery: procedure use, readmission rates, and mortality", *JAMA*, 294:1960-1963(2005).

Wynne, "Oxyntomodulin increases energy expenditure in addition to decreasing energy intake in overweight and obese humans: a randomised controlled trial", *Intenational Journal of Obesity*, 12:1729-1736 (2006).

Wynne, "Subcutaneous oxyntomodulin reduces body weight in overweight and obese subjects: a double-blind, randomized, controlled trial", *Diabetes*, 54: 2390-2395 (2005).

Yoshinaga, "Structural requirements of peptide YY for biological activity at enteric sites", *Am. J. Physiol.*, 263:G698-G701 (1992).

Yoshinaga, et al., "Structural requirements of peptideYY for biological activity at enteric sites," *Am. J. Physiol. Gastrointest. Liver Physiol.* 263, G695 (1992).

Young, et al., "Authentic Cell-Specific and Developmentally Regulated Expression of Pro-Opiomelanocortin Genomic Fragments in Hypothalamic and Hindbrain Neurons of Transgenic Mice," *J. Neurosci*, 18,6631 (1998).

Zhang, "Positional cloning of the mouse obese gene and its human homologue", *Nature*, 372:425 (1994).

P01275 (gi45644939): "Glucagon precursor", GenBank Record dated Jan. 23, 2007, (GenBank [online] Bethesda, MD USA: United States National Library of Medicine, retrieved on Jun. 9, 2007, retrieved from internet using <URL:http://www.ncbLnlm.nih.gov/entrezlviewer.fcgi?db=protein&va1=45644939>, GenBank Accession No. P01275 (gi45644939).

P01275 (gi121484): "Glucagon precursor", GenBank Record dated Aug. 20, 2001, (GenBank [online]Bethesda, MD USA: United States National Library of Medicine, retrieved on Jun. 9, 2007, retrieved from internet using <URL:http://www.ncbi.nlm.nih.gov/entrezlviewer.fcgi?121484: )OLD09:43184>, GenBank Accession No. P01275 (gi121484).

P01273 (gi1346151): "Glucagon precursor", GenBank Record dated Jul. 10, 2007, (GenBank [online]Bethesda, MD USA: United States National Library of Medicine, retrieved on Jun. 9, 2007, retrieved from internet using <URL:http://www.ncbi.nlm.nih.gov/entrezlviewer.fcgi?db=protein&val=1346151 >, GenBank Accession No. P01273 (gi1346151).

P01275: "GLUe_HUMAN", ExPASy [online] Swiss Institute of Bioinformatics (SIB), Gasteiger E., Gattiker A., Hoogland C., Ivanyi I., Appel R.D., Bairoch A. ExPASy: the proteomics server for in-depth protein knowledge and analysis Nucleic Acids Res. 31:3784-3788(2003), retrieved on May 27, 2005, retrieved from internet using <URL:http://www.au.expasy.org/cgi-bin/sprot-ft-details.pl?P01275@PEPTIDE@53@89>, ExPASy Accession No. P01275.

P01272 (gi121474): "Glucagon precursor", GenBank Record dated Aug. 21, 2001, (GenBank [online]Bethesda, MD USA: United States National Library of Medicine, retrieved on Jun. 9, 2007, retrieved from internet using <URL:http://www.ncbi.nlm.nih.gov/entrezlviewer.fcgi?db=protein&val=121479>, Genbank Accession No. P01272 (gi121479).

P06883 (gi121496): "Glucagon precursor", GenBank Record dated Jul. 10, 2001, (GenBank [online]Bethesda, MD USA: United States National Library of Medicine, retrieved on Jun. 9, 2007, retrieved from internet using <URL:http://www.ncbi.nlm.nih.gov/entrezlviewer.fcgi?db=protein&val=121496>, Genbank Accession No. P06883 (gi121496).

Anderson & Rasmussen, "Cimetidine and obesity: Conflicting evidence", Intl. J. Obesity 23:550 (1999).

Aubuchowski, "Cancer therapy with chemically modified enzymes I. Antitumor properties of polyethylene glycolasparaginase conjugates", Cancer Biochem. Biophys., 7(2):175-86 (1984).

Bagger, "Nasal bioavailability of peptide T in rabbits: Absorption enhancement by sodium glycocholate and glycofurol" Eur. J. Pharm. Sci. 14:69-74 (2001).

Dakin, "Novel Actions of Oxyntomodulin in the Central Nervous System", Dept. of Endocrinology & Metabolism, Imperial College School Medicine, Hammersmith Hospital, Du Cane Road, London. W12 ONN, Journal of Endocrinology, Mar. 2000. vol. 164 Supplement (Abstract #181).

Dakin, "Novel Actions of Oxyntomodulin in the Central Nervous System", Dept. of Endocrinology & Metabolism, Imperial College School Medicine, Hammersmith Hospital, Du Cane Road, London, W12.

ONN. UK presented at the 19th Joint Meeting of the British Endocrine Societies, with the European Federation of Endocrine Societies, Mar. 13-16, 2000.

CAA27627 (gi762941): "unnamed protein product [Homo sapiens]", NCBI Record dated Dec. 3, 2009, (Database Medline [online], Bethesda, MD, USA: US National Library of Medicine (NLM), retrieved from internet using <URL:http://www.ncbi.nlm.nih.gov/protein/762941, NCBI Accession No. CAA27627 (gi1762941).

ExPasy Proteomics Tools, Compute pI/MW, http://ca.expasy.org/cgi-bin/pi_tool, printed on Apr. 10, 2007.

Kawana, "Nasal immunization of mice with peptide having a cross-neutralization epitope on minor capsid protein L2 of human papillomavirus type 16 elicit systemic and mucosal antibodies" Vaccine 19:1496-1502 (2001).

Leger, "Identification of CJC-1131-Albumin Bioconjugate as a Stable and Bioactive GLP-1(7-36) Analog", Bioorganic & Medicinal Chemistry Letters, Oxford, GB, 14:17 (2004) 4395-4398.

Qin, "Direct interaction of Gβγ with a C-terminal Gβγ-binding domain of the $Ca^{2+}$ channel $a_1$ subunit is responsible for channel inhibition by G protein-coupled receptors", PNAS, 94, 8878 (1997).

Lloyd, "Inhibitory effect of PYY on vagally stimulated acid secretion is mediated predominantly by $Y_1$ receptors", American Journal of Physiology, 270(1):123-127 (Jan. 1996).

Search Report dated Jan. 23, 2003 from International Application No. PCT/GB02/04082.

Tani, "Oxyntomodulin and related peptides control somatostatin secretion in RIN T3 cells" Biochim. Biophys. Acta 1095:249-254 (1991).

Tzotsas, "Use of somatostatin analoQues in obesity" Drugs 68: 1963-1973(2008).

Bado, A. et al., "Neurotensin and Oxyntomodulin-(30-37) potentiate PYY regulation of gastric acid and somatostatin secretions," Am. J. Physiol., 1993, vol. 265, No. 1 Pt. 1, p. G113-7.

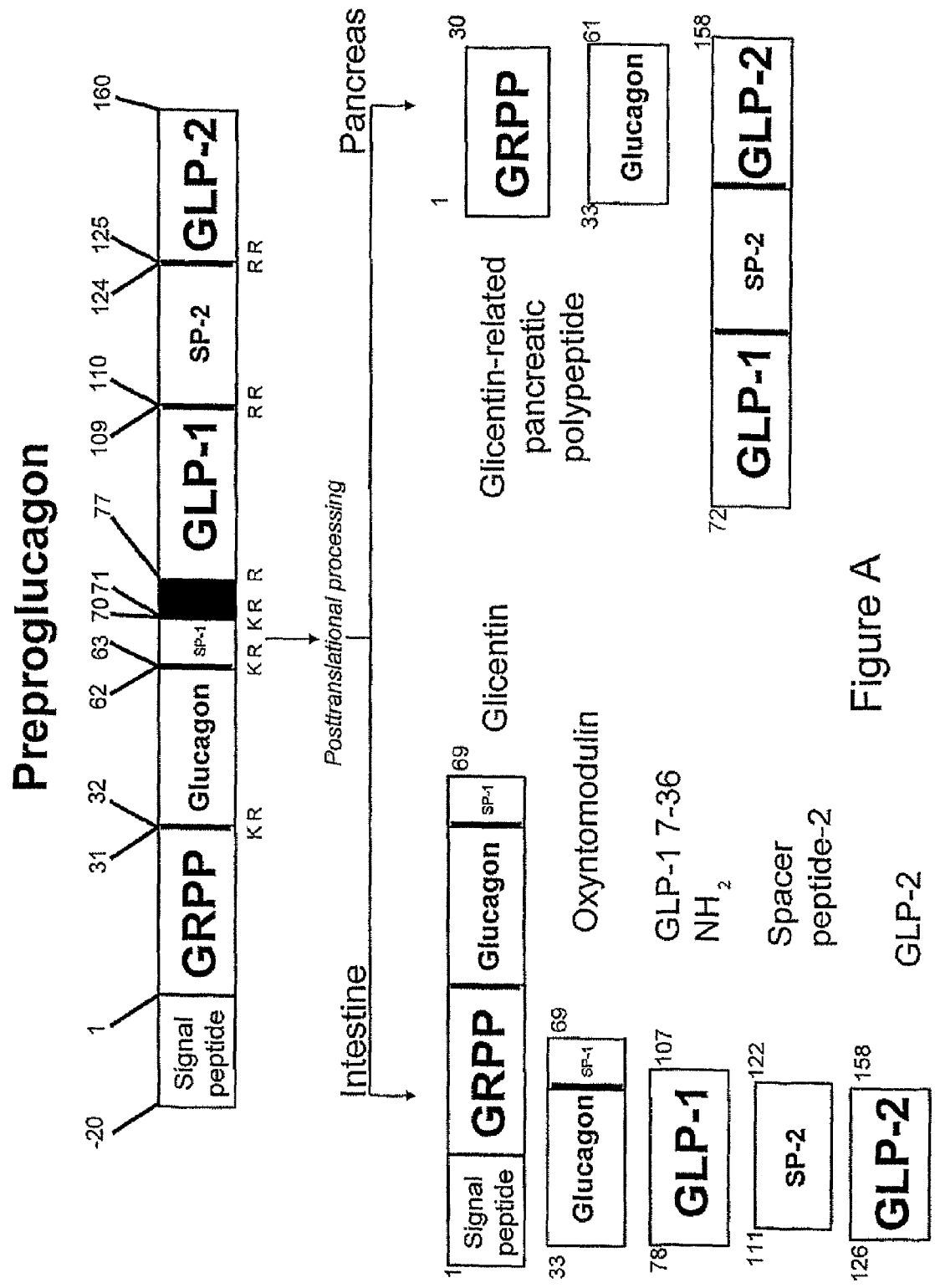
Figure A

A

B

A)

B)

C)

MODIFICATION OF FEEDING BEHAVIOUR

CROSS-REFERENCE TO RELATED APPLICATIONS

This application is a divisional application of U.S. Ser. No. 10/541,526 filed on Jul. 7, 2005, which is a §371 filing of PCT/GB2004/000017, filed Jan. 12, 2004, which claims priority under 35 U.S.C. § 119 to United Kingdom Application No. GB 0300571.7, filed on Jan. 10, 2003.

INTRODUCTION

The present invention relates to compositions and methods for use in weight loss in mammalian animals.

BACKGROUND OF THE INVENTION

One of the diseases with the highest incidence but which lacks effective treatment is obesity. It is a debilitating condition which reduces quality of life and substantially increases the risk of other diseases.

In the USA 25% of the adult population is now considered to be clinically obese. It has been estimated that $45 billion of US healthcare costs, or 8% per annum of total healthcare spend, is a direct result of obesity. In Europe the problem is increasing. It has been predicted that without new approaches over 20% of the UK population will be clinically obese by 2005. The fact that obesity is a metabolic disease is being increasingly recognized by the medical profession and the health authorities. There is, however, a shortage of effective and safe drugs which can be used in conjunction with diet and exercise for the long-term management of obesity.

It is an object of the present invention to provide such drugs and also to provide means to identify and develop further such drugs.

Preproglucagon is a 160 amino acid polypeptide which is cleaved in a tissue specific manner by prohormone convertase-1 and -2 giving rise to a number of products with a variety of functions in both the central nervous system (CNS) and peripheral tissues. In the intestine and in the CNS, the major post-translational products of preproglucagon cleavage are glucagon-like peptide-1 (GLP-1), glucagon-like peptide-2 (GLP-2), glicentin and oxyntomodulin (OXM), as shown in Figure A. While GLP-1 and GLP-2 have been shown to inhibit food intake, no such role has been demonstrated in humans for the distinct peptide OXM. The importance of OXM as a biologically active peptide in humans has not been demonstrated.

SUMMARY OF THE INVENTION

The present invention is based on our surprising observations that the OXM peptide can inhibit food intake, reduce weight and increase energy expenditure in humans, and also that OXM infusion suppresses fasting plasma ghrelin.

The present invention provides a method for the prevention or treatment of excess weight in a mammal, the method comprising administering a composition comprising OXM to a mammal. The mammal is likely to be in need of prevention or treatment of excess weight. The weight loss may be cosmetic. The composition comprising OXM will be administered in an effective concentration.

The present invention also provides the following methods of treatment of a subject: a method for decreasing calorie intake in a subject, a method for decreasing appetite in a subject, a method for decreasing food intake in a subject, a method for weight control or treatment in a subject, a method for reduction or prevention of obesity, and a method for increasing energy expenditure; in particular any one or more of the following: preventing and reducing weight gain; inducing and promoting weight loss; and reducing obesity as measured by the Body Mass Index. The methods include control of any one or more of appetite, satiety, hunger and energy expenditure, in particular any one or more of the following: reducing, suppressing and inhibiting appetite; inducing, increasing, enhancing and promoting satiety and sensations of satiety; and reducing, inhibiting and suppressing hunger and sensations of hunger; and increasing energy expenditure. The methods further include maintaining any one or more of a desired body weight, a desired Body Mass Index, a desired appearance and good health. In all the above methods OXM is administered to a subject, generally by a peripheral route of administration.

The present invention also provides a method for improving lipid profile in a subject. The method includes administering to the subject an effective amount of OXM. An improvement in lipid profile includes, but is not limited to, at least one method of reducing cholesterol levels, reducing triglyceride levels and increasing HDL cholesterol levels. OXM can be administered peripherally, such as in a single or divided dose.

In another embodiment, a method is disclosed herein for alleviating a condition or disorder which can be alleviated by reducing nutrient availability and/or increasing energy expenditure. The method includes administering to a subject a therapeutically effective amount of OXM.

The present invention provides a pharmaceutical composition comprising OXM and a pharmaceutically suitable carrier, in a form suitable for oral, rectal, parenteral e.g. intravenous, intramuscular, or intraperitoneal, mucosal e.g. buccal, sublingual, nasal, subcutaneous or transdermal administration, including administration by inhalation. If in unit dosage form, the dose per unit may be, for example, as described below or as calculated on the basis of the per kg doses given below.

The present invention also includes OXM or an agonist thereof for use in the manufacture of a medicament for administration by a route peripheral to the brain for any of the methods of treatment described above. Examples of peripheral routes include oral, rectal, parenteral e.g. intravenous, intramuscular, or intraperitoneal, mucosal e.g. buccal, sublingual, nasal, subcutaneous or transdermal administration, including administration by inhalation. Preferred dose amounts of OXM for the medicaments are given below.

The present invention provides a method for cosmetic weight loss in a mammal, the method comprising administering a composition comprising OXM to a mammal. In this circumstance, the weight loss is purely for the purposes of cosmetic appearance. The present invention further provides the use, in combination, of OXM and another agent that has an influence in any way on weight and/or food intake, for example, an agent that has any one of more of the following effects: reduces food intake and/or reduces hunger, reduces weight, reduces or prevents obesity, increases energy expenditure or reduces nutrient availability in a mammal, especially a human. The other agent is, for example, GLP-1 or an agonist thereof receptor, or PYY or an agonist thereof, or another substance that is or is derived from a naturally food influence substance, for example, amylin, leptin, exendin-4 or agonists thereof. If desired, more than one other agent may be used in combination with OXM, for example, GLP-1 or an agonist thereof and PYY or an agonist thereof may be used. (It will be understood that a reference to a substance "or an agonist thereof" includes mixtures of the substances and one or more agonists thereof, and also mixtures of two or more agonists.)

In the methods of the invention, OXM is administered in an amount effective to achieve the desired result, as is any other agent used in combination with OXM. In each case, the subject, generally a human, may be overweight and/or may be diabetic.

BRIEF DESCRIPTION OF THE FIGURES

Figure A is a graphical representation of preproglucagon and its component parts.

FIG. 1 is a comparison of the effects of ICV and iPVN proglucagon-derived and related products on food intake in fasted rats.

FIG. 2 shows two graphs of the effects of ICV and iPVN OXM on food intake in fasted rats.

FIG. 4 shows two bar graphs of the inhibition of OXM and GLP-1 effects on food intake by exendin-(9-39).

DETAILED DESCRIPTION OF THE INVENTION

Figure 1A:
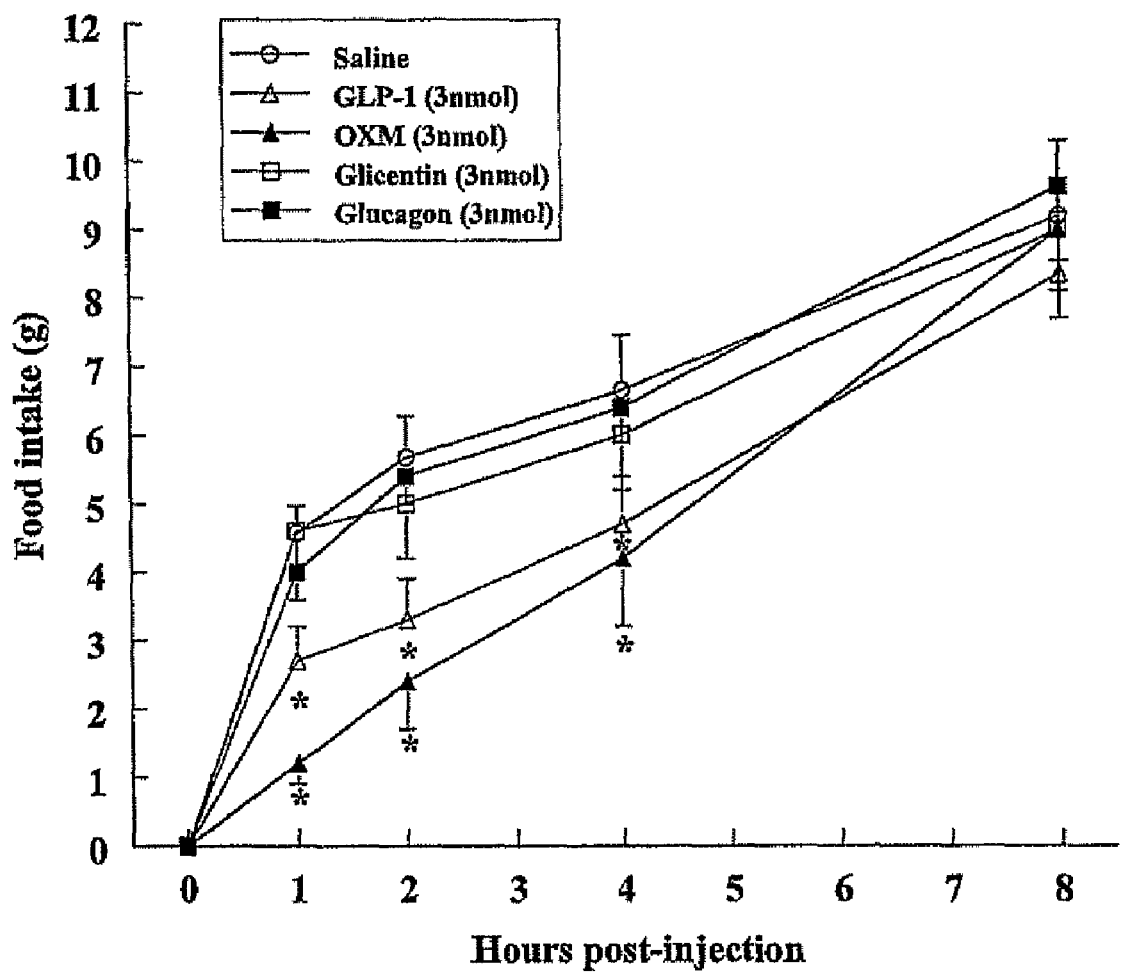
FIG. 1A illustrates the cumulative food intake (g) up to 8 h after ICV injection of GLP-1, OXM, glucagon, or glicentin (all 3 nmol) into fasted animals, *, P<0.05 vs. saline control.

The present invention is based on the surprising observation that, found that contrary to expectations, the OXM peptide can inhibit food intake and reduce weight.

In this text, the term "oxyntomodulin" is the same as "OXM" and relates to any composition which includes an OXM peptide sequence or an analogue thereof as follows:

OXM sequences are well known and documented in the art. The present invention relates to all of the sequences recited herein including, in particular, the OXM human sequence SEQ ID NO: 9 (which is the same as the rat, and hamster OXM sequence), as follows:

```
                                          SEQ ID NO: 9
His Ser Gln Gly Thr Phe Thr Ser Asp Tyr Ser Lys

Tyr Leu Asp Ser Arg Arg Ala Gln Asp Phe Val Gln

Trp Leu Met Asn Thr Lys Arg Asn Arg Asn Asn Ile

Ala
``` the OXM angler fish sequence SEQ ID NO: 2 as follows:

```
                                          SEQ ID NO: 2
    His Ser Glu Gly Thr Phe Ser Asn Asp Tyr

Ser Lys Tyr Leu Glu Asp Arg Lys Ala Gln

Glu Phe Val Arg Trp Leu Met Asn Asn Lys

Arg Ser Gly Val Ala Glu
``` and the eel OXM sequence SEQ ID NO: 3 as follows:

```
                                          SEQ ID NO: 3
    His Ser Gln Gly Thr Phe Thr Asn Asp Tyr

Ser Lys Tyr Leu Glu Thr Arg Arg Ala Gln

Asp Phe Val Gln Trp Leu Met Asn Ser Lys

Arg Ser Gly Gly Pro Thr
```

The term OXM used in this text also covers any analogue of the above OXM sequence, wherein the histidine residue at position 1 is maintained or replaced by an aromatic moiety carrying a positive charge or a derivative thereof preferably wherein the moiety is an amino acid, more preferably wherein it is a histidine derivative, while 1, 2, 3, 4, 5, 6, 7, 8, 9, 10, 11, 12, 13, 14, 15, 16, 17, 18, 19, 20, 21 or 22 of the other amino acids in the above OXM sequence can be independently replaced by any other independently chosen amino acid, with the exception of histidine in position 1.

Any one or more (to 22) other alpha-amino acid residue in the sequence can be independently replaced by any other one alpha-amino acid residue. Preferably, any amino acid residue other than histidine is replaced with a conservative replacement as well known in the art i.e. replacing an amino acid with one of a similar chemical type such as replacing one hydrophobic amino acid with another.

As discussed above, 1 to 22 of the amino acids can be replaced. In addition to the replacement option above, this may be by a non-essential or modified or isomeric form of an amino acid. For example, 1 to 22 amino acids can be replaced by an isomeric form (for example a D-amino acid), or a modified amino acid, for example a nor-amino acid (such as norleucine or norvaline) or a non-essential amino acid (such as taurine). Furthermore, 1 to 22 amino acids may be replaced by a corresponding or different amino acid linked via its side chain (for example gamma-linked glutamic acid). For each of the replacements discussed above, the histidine residue at position 1 is unaltered or defined above.

In addition, 1, 2, 3, 4 or 5 of the amino acid residues can be removed from the OXM sequence with the exception of histidine at the 1 position (or as defined above). The deleted residues may be any 2, 3, 4 or 5 contiguous residues or entirely separate residues.

The C-terminus of the OXM sequence may be modified to add further amino acid residues or other moieties. The OXM above may be provided as the corresponding salt thereof. Examples of pharmaceutically acceptable salts of OXM and its analogues include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts may be prepared in a conventional manner using methods well known in the art. Acid addition salts of said basic compounds may be prepared by dissolving the free base compounds in aqueous or aqueous alcohol solution or other suitable solvents containing the required acid. Where OXM contains an acidic function a base salt of said compound may be prepared by reacting said compound with a suitable base. The acid or base salt may separate directly or can be obtained by concentrating the solution e.g. by evaporation. OXM may also exist in solvated or hydrated forms. The OXM of the present invention may be conjugated to one or more groups such as a lipid, sugar, protein or polypeptide. The OXM can be conjugated by being attached to the group (for example via a covalent or ionic bond) or can be associated therewith. The conjugated link is preferably not through the C or N terminus amino acid, when the OXM is attached to the group. The OXM can be conjugated to a polymer such as polyethylene glycol, polyvinylpyrrolidone, polyvinylalcohol, polyoxyethylene-polyoxypropylene copolymers, polysaccharides such as cellulose, cellulose derivatives, chitosan, acacia gum, karaya gum, guar gum, xanthan gum, tragacanth, alginic acid, carrageenan, agarose, and furcellarans, dextran, starch, starch derivatives, hyaluronic acid, polyesters, polyamides, polyanhydrides, and polyortho esters.

The OXM can be chemically modified. In particular, the amino acid side chains, the N terminus and/or the C acid terminus of OXM can be modified. For example, the OXM can undergo one or more of alkylation, disulphide formation, metal complexation, acylation, esterification, amidation, nitration, treatment with acid, treatment with base, oxidation or reduction. Methods for carrying out these processes are well known in the art. In particular the OXM is provided as a lower alkyl ester, a lower alkyl amide, a lower dialkyl amide, an acid addition salt, a carboxylate salt or an alkali addition salt thereof. In particular, the amino or carboxylic termini of the OXM may be derivatised by for example, esterification, amidation, acylation, oxidation or reduction. In particular, the carboxylic terminus of the OXM can be derivatised to form an amide moiety.

The OXM can be treated with metals, in particular with divalent metals. For the purposes of this invention the OXM can therefore be provided in the presence of one or more of the following metals, zinc, calcium, magnesium, copper, manganese, cobalt, molybdenum or iron.

The OXM can be provided in the form of a pharmaceutical composition in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The OXM can be provided as a crystalline solid, a powder, an aqueous solution, a suspension or in oil.

The compositions according to the invention for use in the aforementioned indications may be administered by any convenient method, for example by oral, rectal, parenteral e.g. intravenous, intramuscular, or intraperitoneal, mucosal e.g. buccal, sublingual, nasal, subcutaneous or transdermal administration, including administration by inhalation, and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions, including compositions for subcutaneous administration, comprise a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

OXM may be administered peripherally at a dose of, for example, 0.1 nmoles or more per kg body weight of the subject, for example, 0.2 nmoles or more, for example, 0.5 nmoles or more, for example, 1 nmole or more, for example, 1.5 nmoles or more, for example, 2 nmole or more, for example, 2.5 nmoles or more, for example, 3 nmoles or more, for example, 4 nmoles or more, for example, 5 nmoles or more, for example, 6 nmoles or more, for example, 7 nmoles or more, for example, 8 nmoles or more, for example, 9 nmoles or more, for example, 10 nmoles, for example, 11 nmoles or more, for example, up to 12 nmoles per kg body weight. The amount used may be up to 11 nmoles per kg body weight, for example, up to 10 nmoles, for example, up to 9 nmoles, for example, up to 8 nmoles, for example, up to 7 nmoles, for example, up to 6 nmoles, for example, up to 5 nmoles, for example, up to 4 nmoles, for example, up to 3 nmoles, for example, up to 2 nmoles, for example, up to 1 nmoles, for example, up to 0.5 nmoles, for example, up to 0.4 nmoles, for example, up to 0.2 nmoles per kg body weight. The dose is generally in the range of from 0.1 to 12 nmoles per kg body weight, for example, within any combination of upper and lower ranges given above. A dose may be calculated on an individual basis or on the basis of a typical subject, often a 70 or 75 kg subject. The dose may be administered before each meal.

For subcutaneous administration, a dose of OXM within the range of from 100 nmol to 500 nmol i.e. about 0.5 mg to about 2 mg, which dose is calculated on the basis of a 75 kg subject, may be administered, generally before meals.

A pharmaceutical preparation in unit dosage form for peripheral administration preferably comprises an amount of OXM calculated on the basis of the per kg doses given above. Typically, the dose may be calculated on the basis of a 70 or 75 kg subject. A composition for subcutaneous administration, for example, may comprise a unit dose of OXM within the range of from 100 nmol to 500 nmol i.e. about 0.5 mg to about 2 mg, calculated on the basis of a 75 kg subject.

The OXM can be used as a prophylaxis to prevent excess weight gain or can be used as a therapeutic to lose excess weight.

The excess weight is typically obesity, although the mammal will not be certified as clinically obese in order to be suffering from excess weight. The OXM may be in liquid, solid or semi-solid form.

In today's society, the prevention or treatment of excess weight in a mammal is a real need. Preferably the mammal is a human, although it may also include other mammalian animals, such as horses, canine animals (in particular domestic canine animals), feline animals (in particular domestic feline animals) as well as mammals which are produced for meat, such as porcine, bovine and ovine animals. The present invention can be used to prevent excess weight in such animals in order to maximise lean meat production.

Throughout this text, the term "prevention" means any effect which mitigates any excess weight, to any extent. Throughout this text, the term "treatment" means amelioration of excess weight, to any extent.

Suitable doses of OXM include those that raise the concentration of OXM significantly above the basal concentration of OXM, such as, but not limited to, a dose that that mimic postprandial serum concentrations of OXM. Thus, in one embodiment, OXM is administered to a reduction in calorie intake, food intake, or appetite equivalent to the reduction in calorie intake, food intake, or appetite, or to increase the energy expenditure, caused by the postprandial level of OXM.

For all methods disclosed herein, the dose of OXM can be based on the physiological levels observed post-prandially. A single dose may be administered per day, or divided doses can be used (see above).

It is preferable to administer OXM via a peripheral route of administration, that is to say, via a route other than directly to the brain. Examples of such routes include oral, rectal, parenteral e.g. intravenous, intramuscular, or intraperitoneal, mucosal e.g. buccal, sublingual, nasal, subcutaneous or transdermal administration, including administration by inhalation.

The present invention provides a pharmaceutical composition comprising OXM and a pharmaceutically suitable carrier, in a form suitable for oral, rectal, parenteral e.g. intravenous, intramuscular, or intraperitoneal, mucosal e.g. buccal, sublingual, nasal, subcutaneous or transdermal administration, including administration by inhalation. If in unit dosage form, the dose may per unit may be calculated on the basis of the per kg doses given above.

The present invention also includes OXM or an agonist thereof for use in the manufacture of a medicament for administration by a peripheral route for any of the methods of treatment described above. Examples of peripheral routes include oral, rectal, parenteral e.g. intravenous, intramuscular, or intraperitoneal, mucosal e.g. buccal, sublingual, nasal, subcutaneous or transdermal administration, including administration by inhalation. Preferred dose amounts of OXM for the medicaments are given above.

The present invention provides a method for cosmetic weight loss in a mammal, the method comprising administering a composition comprising OXM to a mammal. In this circumstance, the weight loss is purely for the purposes of cosmetic appearance.

All preferred features given above apply to this aspect of the invention.

Without being bound to this theory, it is understood that the present invention provides the prevention or treatment of excess weight by the administration of OXM which acts as an inhibitor to food intake to the mammalian body and/or increases energy expenditure. Such reduced food intake and/or increased energy expenditure results in the prevention or treatment of excess weight in a mammal. In this text the term "food" includes a substance which is ingested and which has calorific value. Furthermore, we have found that OXM infusion suppresses fasting plasma ghrelin. This is an important finding because ghrelin is a powerful stimulant of appetite in man and preprandial rises in plasma ghrelin have been suggested to be a trigger for meal initiation. Without being bound by the hypothesis, we consider that inhibition of the normal preprandial rise in ghrelin by OXM is likely to be one mechanism by which OXM infusion reduces appetite.

The present invention further provides the use, in combination, of OXM and another agent that has an influence in any way on weight and/or food intake, for example, an agent that has any one of more of the following effects: reduces food intake and/or reduces hunger, reduces weight, reduces or prevents obesity, increases energy expenditure or reduces nutrient availability in a mammal, especially a human. The other agent is, for example, GLP-1 or an agonist thereof receptor, or PYY or an agonist thereof, or another substance that is or is derived from a naturally food influence substance, for example, amylin, leptin, exendin-4 or agonists thereof. If desired, more than one other agent may be used in combination with OXM, for example, GLP-1 or an agonist thereof and PYY or an agonist thereof may be used. (It will be understood that a reference to a substance "or an agonist thereof" includes mixtures of the substances and one or more agonists thereof, and also mixtures of two or more agonists.)

In one embodiment OXM may be used with GLP-1 or an agonist thereof. OXM appears to have an arcuate site of action, whereas GLP-1 acts via the brain stem. The use of the two agents in combination may give a synergistic effect.

GLP-1, like OXM, is a post-translational product of preproglucagon, see Figure A. The initial post-translational product is GLP-1 (1-37). Human GLP-1 (1-37) has the following amino acid sequence, SEQ ID NO: 4:

```
                                         SEQ ID NO: 4
His Asp Glu Phe Glu Arg His Ala Glu Gly Thr Phe

Thr Ser Asp Val Ser Ser Tyr Leu Glu Gly Gln Ala

Ala Lys Glu Phe Ile Ala Trp Leu Val Lys Gly Arg

Gly
```

Further modifications give GLP-1 (1-36) SEQ.ID.NO: 5, and the amide thereof GLP-1 (1-36) $NH_2$; GLP-1 (7-37) SEQ.ID.NO:6; and GLP-1 (7-36) SEQ.ID.NO:7 and the amine thereof, GLP-1 (7-36) $NH_2$, which is the most biologically active of the GLP-1 peptides. The term "GLP-1" is used herein to denote any of the GLP-1 peptides defined above, especially GLP-1 (7-36) $NH_2$, also known as GLP-1 (7-36) amide. The terms encompasses GLP-1 peptides of any animal origin, especially the human peptides.

A GLP-1 agonist is a peptide, small molecule, or chemical compound that preferentially binds to the GLP-1 receptor and stimulates the same biological activity as does GLP-1. In one embodiment, an agonist for the GLP-1 receptor binds to the receptor with an equal or greater affinity than GLP-1. In another embodiment, an agonist selectively binds the GLP-1 receptor, as compared to binding to another receptor. Exendin-4, which is a 39-amino acid peptide isolated from the salivary glands of the Gila monster (*Heloderma suspectum*) (Eng J et al J Biol Chem 267:7402-7405, 1992) is an example of an agonist at the GLP-1 receptor. Molecules derived from exendin-4 and that also have GLP-1 agonist activity are further examples of GLP-1 agonists. GLP-1 agonists include GLP-1 related peptides and peptides that result from natural or synthetic enzymatic or chemical processing of preproglucagon or of a GLP-1 peptide or a related peptide.

Any compound that is described as being a GLP-1 agonist may be used in the present invention, as may any compound that is tested for GLP-1 agonist activity, for example, as described above, and found to function as a GLP-1 agonist. A recombinant GLP-1 receptor suitable for use in screening is disclosed in WO93/19175. Many GLP-1 agonists are known and are described in the art. Examples of published patent specifications that disclose GLP-1 agonists are the following: WO2002/67918, WO2002/66479, WO2002/03978, WO2001/89554, WO2001/14386, WO2001/66135, WO2001/35988, WO2001/14368, WO2001/04156, WO2000/78333, WO2000/59887, WO2000/42026, HP 0955314, and WO99/43707. Examples of GLP-1 agonists are Arg34, Lys26(N-epsilon-(gamma-Glu(N-alpha-hexadecanoyl)))-GLP-1 (7-37), IP7-GLP-1 (7-37)OH.

It may be advantageous to use PYY or an agonist thereof with OXM. PYY has a sustained duration of action, for example, when administered peripherally, it continues to act after it has been cleared from the circulating blood, for example, for up to 24 hours after administration. Accordingly, PYY is effective when two or even one dose per day is administered. Without being limited by the following, OXM appears to have an immediate effect, which may not be sustained for a prolonged period. OXM may be administered several times per day, for example, before a meal. The use of long acting PYY with short acting OXM enables "fine tuning" of administration regimes to the needs of the user.

PYY is a 36-residue peptide amide isolated originally from porcoine intestine (Tatemoto et al. Proc. Natl. Acad. Sci. 79:2514, 1982). The term as used herein includes PYY obtained or derived from any species. Thus, PYY includes the human full length polypeptide, which has the following sequence, SEQ ID NO: 8:

```
                                          SEQ ID NO: 8
Tyr Pro Ile Lys Pro Glu Ala Pro Gly Glu Asp Ala

Ser Pro Glu Glu Leu Asn Arg Tyr Tyr Ala Ser Leu

Arg His Tyr Leu Asn Leu Val Thr Arg Gln Arg Tyr
``` and species variations of PYY, including e.g. murine, hamster, chicken, bovine, rat, and dog. In one embodiment, PYY agonists do not include NPY. The term PYY as used herein also includes $PYY_{3-36}$. It may be advantageous to use $PYY_{3-36}$. A PYY agonist is any compound which binds to a receptor that specifically binds PYY, and elicits an effect of PYY. In one embodiment, a PYY agonist is a compound that affects food intake, caloric intake, or appetite, and/or which binds specifically in a Y receptor assay or competes for binding with PYY, such as in a competitive binding assay with labeled PYY. PYY agonists include, but are not limited to, compounds that bind to the Y2 receptor.

PYY agonists and compounds that may be used as PYY agonists are disclosed in the art. For example, contemplated as useful PYY agonists are Y2 specific NPY peptide agonists as described in U.S. Pat. No. 5,026,685; U.S. Pat. No. 5,574,010; U.S. Pat. No. 5,604,203; U.S. Pat. No. 5,696,093; U.S. Pat. No. 6,046,167. There may also be used variants of PYY and of neuropeptide Y that are analogous to the variants and modifications of OXM described above.

If desired, OXM may be used in with both GLP-1 or an agonist thereof and PYY or an agonist thereof.

The use of a combination of any of OXM and GLP-1 or an agonist thereof and PYY or an agonist thereof may serve to increase the effectiveness of any of the agents compared with its use alone, for example, as described above. Alternatively or in addition, use of the two or three agents in combination may reduce any tendency for "escape" when using an agent alone. The term "escape" is used to denote a reduction in effect of an agent with time. For example, if any one of the agents above has been used alone, its effect may reduce with time. Use of one or both of the other agents in addition may reduce or prevent the tendency for that reduction in effectiveness. For example, PYY has a sustained effect and may be used for prolonged periods. If the effect of PYY should appear to reduce, or to reduce or prevent any such reduction in effect OXM may be administered in addition to the PYY. GLP-1 may also be used for the same purpose, with OXM or with OXM and PYY.

If desired, one or more other agents, such as, but not limited to, an additional appetite suppressant, may also be administered. Specific, non-limiting example of an additional appetite suppressant include amfepramone (diethylpropion), phentermine, mazindol and phenylpropanolamine, fenfluramine, dexfenfluramine, and fluoxetine. When used in combination with another agent, OXM may be administered simultaneously or substantially simultaneously as the other agent, or sequentially, in either order. OXM and the other agent may be administered in a single pharmaceutical composition or in separate compositions, and they may be administered by the same route or by different routes. It is generally more convenient to administer all the active agents in a single composition. However, in some cases it may be necessary or appropriate to administer the active agents by different routes. For example, peptides are generally not stable on oral administration unless modified or formulated in a special way, so must generally be administered via a non-oral route. Some agonists, for example, GLP-1 agonists, are chemical compounds that are stable when administered orally. It may be appropriate to administer OXM non-orally and the other component by a non-oral route.

According to a preferred aspect of the invention, a therapeutically effective amount of OXM or an agonist thereof is administered with a therapeutically effective amount of GLP-1 or an agonist thereof and/or PYY or an agonist thereof. The term "GLP-1/PYY" is used herein to denote GLP-1 or an agonist thereof and/or PYY or an agonist thereof.

The OXM or agonist thereof and the GLP-1/PYY may be administered simultaneously or substantially simultaneously, or sequentially, in any order. The OXM or agonist thereof and the GLP-1/PYY may be administered in a single pharmaceutical composition or in separate compositions, and they may be administered by the same route or my different routes.

If the OXM and the GLP-1/PYY are to be administered in a single pharmaceutical composition, that composition may be any of those described above for OXM or an agonist thereof. The composition may enable simultaneous or substantially simultaneous administration of the OXM or agonist thereof and the GLP-1/PYY. If desired, the OXM or agonist thereof and the GLP-1/PYY may be compartmentalized in the composition, for example, in different layers of a tablet, or in different granules in a capsule. If desired, such compartmentalization may be designed to give different release properties to the components to enable delivery of the OXM or agonist component and the GLP-1/PYY at different times, for example, sequentially.

Alternatively, the OXM or agonist thereof and the GLP-1/PYY may be formulated in separate pharmaceutical compositions, for example, any of the pharmaceutical compositions described above for OXM and agonists thereof. Such separate compositions may be administered simultaneously or substantially simultaneously, or they may be administered sequentially, in any order. For example, PYY may be administered two times or even once per day, with OXM being administered up to several times per day, for example, before meals.

If administered separately, whether sequentially or simultaneously (or substantially simultaneously), the OXM or agonist thereof and the GLP-1/PYY may be administered by the same route or by different routes, for example, as described above.

When used in combination therapy as described above, OXM may be used in a dose as disclosed above in relation to peripheral administration when used alone, that is to say, OXM may be administered peripherally at a dose of, for example, 0.1 nmoles or more per kg body weight of the subject, for example, 0.2 nmoles or more, for example, 0.5 nmoles or more, for example, 1 nmole or more, for example, 1.5 nmoles or more, for example, 2 nmole or more, for example, 2.5 nmoles or more, for example, 3 nmoles or more, for example, 4 nmoles or more, for example, 5 nmoles or more, for example, 6 nmoles or more, for example, 7 mmoles or more, for example, 8 nmoles or more, for example, 9 nmoles or more, for example, 10 nmoles, for example, 11 nmoles or more, for example, up to 12 nmoles per kg body weight. The amount used may be up to 11 nmoles per kg body weight, for example, up to 10 nmoles, for example, up to 9 nmoles, for example, up to 8 nmoles, for example, up to 7 nmoles, for example, up to 6 nmoles, for example, up to 5 nmoles, for example, up to 4 nmoles, for example, up to 3 nmoles, for example, up to 2 nmoles, for example, up to 1 nmoles, for example, up to 0.5 nmoles, for example, up to 0.4 nmoles, for example, up to 0.2 nmoles per kg body weight. The dose is generally in the range of from 0.1 to 12 nmoles per kg body weight, for example, within any combination of upper and lower ranges given above.

GLP-1 or an agonist thereof may be administered peripherally at a dose of, for example, 0.1 nmoles or more per kg body weight of the subject, for example, 0.2 nmoles or more, for example, 0.4 nmoles or more, for example, 0.6 nmoles or more, for example, 0.8 nmoles or more, for example, 1.0 nmole or more, for example, 1.2 nmoles or more, for example, 1.4 nmoles or more, for example, 1.6 nmoles or more, for example, 1.8 nmoles or more, for example, 2.0 nmoles or more, for example, 2.2 nmoles or more, for example, 2.4 nmoles or more, for example, 2.6 nmoles or more, for example, 2.8 nmoles, for example, 3.0 nmoles or more, for example, up to 3.2 nmoles per kg body weight. The amount used may be up to 3.0 nmoles per kg body weight, for example, up to 2.8 nmoles, for example, up to 2.6 nmoles, for example, up to 2.4 nmoles, for example, up to 2.2 nmoles, for example, up to 2.0 nmoles, for example, up to 1.8 nmoles, for example, up to 1.4 nmoles, for example, up to 1.2 nmoles, for example, up to 1.0 nmoles, for example, up to 0.8 nmoles, for example, up to 0.6 nmoles, for example, up to 0.4 nmoles, for example, up to 0.2 nmoles per kg body weight. The dose is generally in the range of from 0.1 to 3.2 nmoles per kg body weight, for example, within any combination of upper and lower ranges given above.

PYY or an agonist thereof may be used at a dose within the ranges disclosed above for GLP-1. The doses of the various agent may be independent of each other or, for example, equimolar doses may be used, for example, equimolar doses of GLP-1 or an agonist thereof and PYY or an agonist thereof. A dose may be calculated on an individual basis or on the basis of a typical subject, often a 70 or 75 kg subject.

A further embodiment of the present invention is a pharmaceutical composition comprising oxyntomodulin and one or more other agents having an influence in any way on weight and/or food intake, for example, an agent that has any one of more of the following effects: reduces food intake and/or reduces hunger, reduces weight, reduces or prevents obesity, increases energy expenditure or reduces nutrient availability in a mammal, especially a human, in admixture or conjunction with a pharmaceutically suitable carrier. The agents are as defined above and are, for example, GLP-1 or an agonist and/or PYY agonist thereof. The compositions may be, for example, as described above for OXM pharmaceutical compositions. Doses of the OXM and other agents are, for example, as described above.

A pharmaceutical preparation in unit dosage form for peripheral administration preferably comprises an amount of OXM calculated on the basis of the per kg doses given above. Typically, the dose may be calculated on the basis of a 75 kg subject A composition for subcutaneous administration, for example, may comprise a unit dose of OXM within the range of from 100 nmol to 500 nmol i.e. about 0.5 mg to about 2 mg, calculated on the basis of a 75 kg subject.

The present invention also provides the use of OXM in the manufacture of a medicament for the treatment of a subject according to any of the methods disclosed above.

When OXM and another agent that reduces food intake, for example, PYY or an agonist thereof and/or GLP-1 or an agonist thereof are used in the manufacture of a medicament for use in a treatment as described herein, the medicament may be a single pharmaceutical composition comprising all the components, as described above, or may be a two or more component medicament, one component being a pharmaceutical composition comprising OXM, the other component(s) each being a pharmaceutical composition comprising the other agent(s) that reduce food intake, see above.

The medicament, whether a one component medicament or a two or more component medicament as described above, will generally be packaged with instructions relating to its use. Such instructions will refer to the timing, dose and route of administration of the component(s).

The preferred features above relating to methods and compositions relating to OXM when used in combination with other agent also applies to its use in the manufacture of a medicament as described above.

In all embodiments of the invention, the particular dosage regime for which will ultimately be determined by the attending physician and will take into consideration such factors as the OXM being used, animal type, age, weight, severity of symptoms and/or severity of treatment to be applied, method of administration of the medicament, adverse reaction and/or contra indications. Specific defined dosage ranges can be determined by standard designed clinical trials with patient progress and recovery being fully monitored.

Such trials may use an escalating dose design using a low percentage of the maximum tolerated dose in animals as the starting dose in man. Examples of suitable doses are given above.

Preferred features of each aspect of the invention are as for each of the other aspects mutatis mutandis.

The present invention is now described by way of example only in the following non-limiting Examples.

EXAMPLES

Example 1

OXM Causes a Potent Decrease in Fasting-Induced Refeeding when Injected Both ICV and iPVN

Peptides and Chemicals

GLP-1, glicentin, glucagon, and SP-1 were purchased from Peninsula Laboratories, Inc. (St. Helens, UK). OXM was purchased from IAF BioChem Pharma (Laval, Canada). Exendin-4 and exendin-(9-39) were synthesised at Medical Research Council, Hemostasis Unit, Clinical Sciences Center, Hammersmith Hospital, London, UK using F-moc chemistry on an 396 MPS peptide synthesiser (Advanced ChemTech, Inc.) and purified by reverse phase HPLC on a $C_8$ column (Phenomex, Macclesfield, UK). The correct molecular weight was confirmed by mass spectrometry. All chemicals were purchases from Merck & Co. (Lutterworth, Leicester, UK) unless otherwise stated.

Animals

Adult male Wistar rats (ICSM, Hammersmith Hospital) were maintained in individual cages under controlled conditions of temperature (21-23° C.) and light (12 h of light, 12 h of darkness) with ad libitum access to food (RM1 diet, Special Diet Services UK Ltd., Witham, UK) and tap water. Animals were handled daily after recovery from surgery until completion of the studies. All animal procedures undertaken were approved by the British Home Office Animals (Scientific Procedures Act 1986 (Project License PIL 90/1077).

ICV and iPVN cannulation and infusions of test compounds

Animals had permanent stainless steel guide cannulas (Plastics One, Roanoke, Va.) stereotactically implanted ICV (intracerebraventricularly) or iPVN (into the hypothalamic paraventricular nucleus). All studies were carried out in the early light phase, between 0900-1100 h, after a 24-h fast, and food intake was measured 1, 2, 4, 8, and 24 h postinjection.

Feeding Study Protocols

Comparison of the effect of proglucagon-derived products and related peptides on food intake.

In study 1a, rats were injected ICV with 10 μl saline, GLP-1 (13 nmol), OXM (3 nmol), glucagon (3 nmol), or glicentin (3 nmol; n=8/group).

In all studies, OXM with the following sequence, SEQ ID NO: 1, was used:

```
                                            SEQ ID NO: 1
    His Ser Gln Gly Thr Phe Thr Ser Asp Tyr

Ser Lys Tyr Leu Asp Ser Arg Arg Ala Gln

Asp Phe Val Gln Trp Leu Met Asn Thr Lys

Arg Asn Lys Asn Asn Ile Ala
```

Human GLP-1 with the following sequence, SEQ ID NO: 7, was used:

```
                                            SEQ ID NO: 7
    His Ala Glu Gly Thr Phe Thr Ser Asp Val

Ser Ser Tyr Leu Glu Gly Gln Ala Ala Lys

Glu Phe Ile Ala Trp Leu Val Lys Gly Arg.
```

In study 1b, rats were injected iPVN with 1μ saline, GLP-1 (1.0 nmol), OXM (1.0 nmol), glicentin (1.0 nmol), glucagon (1.0 nmol), or SP-1 (3.0 nmol; n=12-15/group). Exendin-4, when injected ICV, inhibits food intake more potently than GLP-1. Therefore, exendin-4 was injected iPVN at a dose of 0.03 nmol.

Investigation of the Effect of Increasing Doses of OXM on Food Intake

In study 2a, rats were injected ICV with saline, GLP-1 (3 nmol), or OXM (0.3, 1, 3 or 10 nmol; n=8/group). In study 2b, rats were injected iPVN with saline, GLP-1 (1.0 nmol), or OXM (0.1, 0.3, or 1.0 nmol; n —12-15/group). To assess whether OXM acts via the GLP-1 receptor, a study using the GLP-1 receptor antagonist exendin-(9-39) was performed.

Night Time Feeding and Behavioural Analysis.

Study 3. It is possible that OXM inhibits food intake via nonspecific taste aversion, and that it is not a true satiety factor. Therefore, ICV cannulated rats were administered GLP-1 (3 nmol), OXM (3 nmol), or saline (n=6/group) at the onset of the dark phase. Food intake was measured 1 h postinjection (study 3a), and behaviour was assessed (study 3b). Rats were observed for 1 h postinjection using a behavioural score sheet.

In study 4a, rats were injected with ICV with saline, GLP-1 (3 nmol), GLP-1 (3 nmol) plus exendin-(9-39) (30 nmol), OXM (3 nmol), OXM (3 nmol) plus exendin-(9-39) (30 nmol), or exendin-(9-39) alone (30 nmol). In study 4b, rats were iPVN injected with saline, GLP-1 (1 nmol), GLP-1 (1 nmol) plus exendin-(9-39) (10 nmol), OXM (1 nmol), OXM (1 nmol) plus exendin-(9-39) (10 nmol), or exendin-(9-39) alone (10 nmol; n=10-12/group).

Receptor Binding Assays. Study 5.

Receptor binding assays were performed in a final volume of 0.5 ml rat hypothalamic membranes (200 μg protein), 500 Bq (100 pM) $[^{125}I]$GLP-1, and unlabeled competing peptides (GLP-1 and OXM) as specified. Membranes were incubated at room temperature for 90 min. Bound and free radioactivity were separated by centrifugation (2 min, 4° C.). Pelleted membranes were washed with assay buffer (0.5 ml, ice-cold), and the membranes were centrifuged as described above. The supernatant was removed, and the radioactivity in the pellet was counted using a γ-counter. Specific (saturable) binding was calculated as the difference between the amount of $[^{125}I]$ GLP-1 bound in the absence (total binding) and presence of 1 μm GLP-1 or OXM (nonsaturable binding). All curves were constructed with points in triplicate. $IC_{50}$ values were calculated using the Prism 3 program (GraphPad Software, Inc., San Diego, Calif.).

Statistics

For food intake analyses, data are presented as the mean ±SEM. Statistical differences between experimental groups were determined by ANOVA, followed by a post-hoc least significant difference test (Systat 8.0, Evanston, Ill.). For behavioural analyses, data are expressed as the median number of occurrences of each behaviour and the range. Comparisons between groups were made using the Mann-Whitney U test (Systat 8.0). In all cases, P<0.05 was considered statistically significant.

Results

Comparison of the effects of proglucagon-derived products and related peptides on food intake ICV Administration.

In study 1a, OXM and GLP-1 (3 nmol) significantly reduced refeeding. This inhibition of food intake lasted until 4 h postinjection (FIG. 1A). Glucagon and glicentin (3 nmol) failed to affect food intake at any time point (FIG. 1A).

iPVN Administration.

Figure 1B:
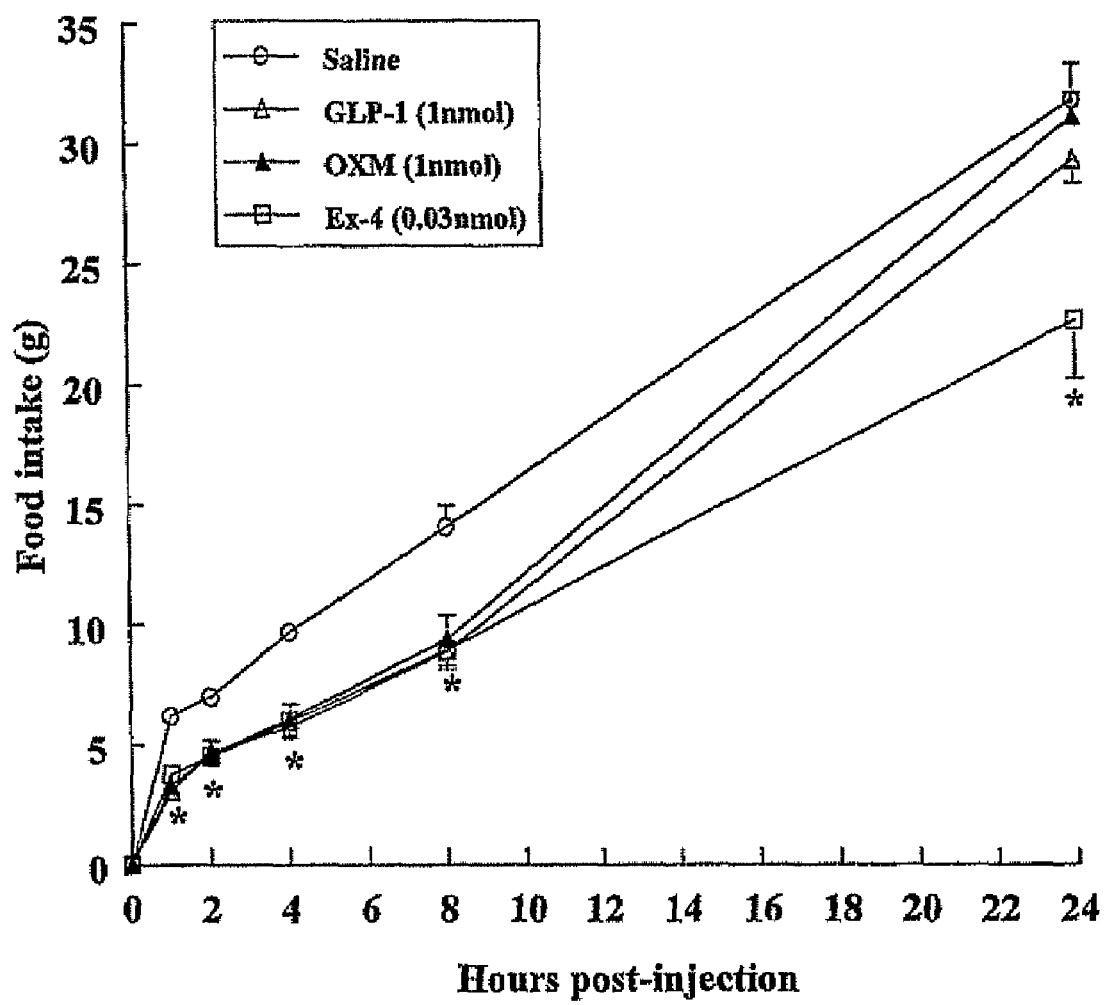
FIG. 1B illustrates cumulative food intake (g) up to 24 h after an acute iPVN injection of GLP-1, OXM (both 1 nmol), or exendin-4 (0.03 nmol) into fasted animals. *, P<0.01 vs. saline control for all groups at 1, 2, and 4 h. *, P<0.05 vs. saline control for exendin-4 only at 8 h.

In study 1b, OXM, GLP-1 (3 nmol) and exendin-4 (0.03 nmol) also inhibited reseeding when injected iPVN. This inhibition lasted at least 8 h postinjection, longer than when injected ICV (FIG. 1B). Glicentin, glucagon (1 nmol), and SP-1 (3 nmol) failed to affect food intake at any time point when injected iPVN.

Effects of increasing doses of OXM on food intake

ICV Administration.

Figure 2A:
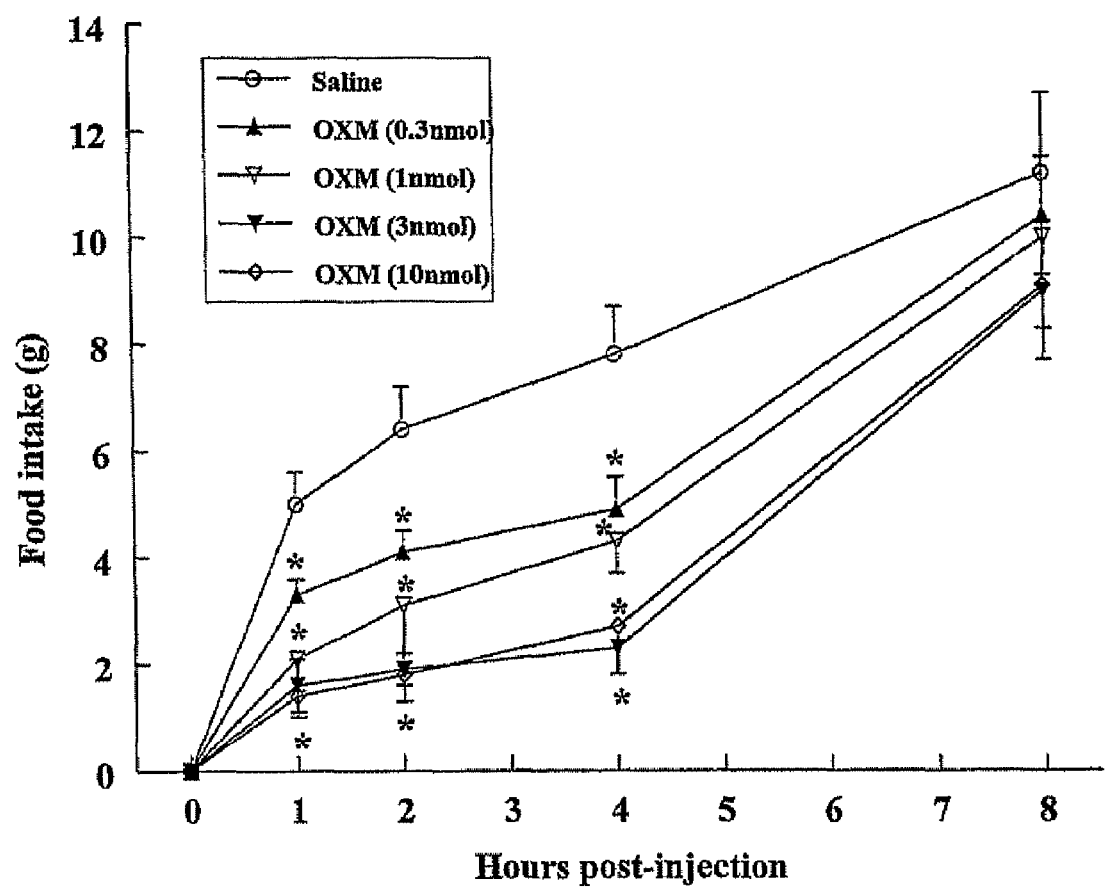
FIG. 2A, cumulative food intake (g) up to 8 h after an acute ICV injection of OXM (0.3, 1, 3, or 10 nmol).

In study 2a, when injected ICV, OXM reduced refeeding in a dose-dependent manner, reaching a maximal effect at a dose of 3 nmol 1, 2, and 4 h postinjection (FIG. 2A).

iPVN Administration.

Figure 2B:
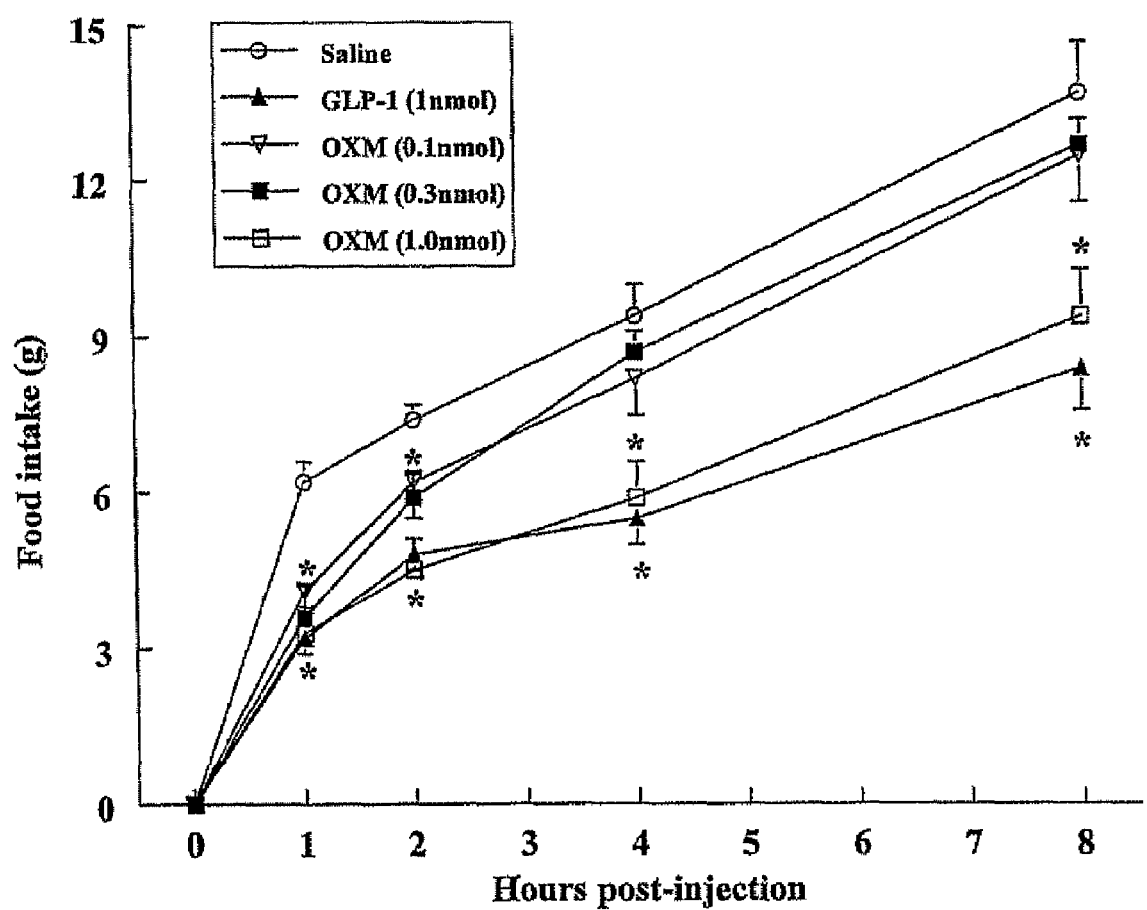
FIG. 2B, cumulative food intake (g) up to 8 h after an acute iPVN injection of OXM (0.1, 0.3, or 1.0 nmol) into fasted animals. *, P<0.05 vs. saline control.

In study 2b, food intake was significantly reduced by iPVN-injected GLP-1 and OXM (both 1 nmol) until 8 h postinjection (FIG. 2B).

Effect of OXM in ICV-Cannulated Sated Rats at the Onset of the Dark Phase.

The dark phase is the rats' natural feeding time. Therefore, assessing the effect of a putative satiety factor in non-fasted animals at this time would represent a more physiological effect.

Effect of OXM on Food Intake.

Figure 3A:
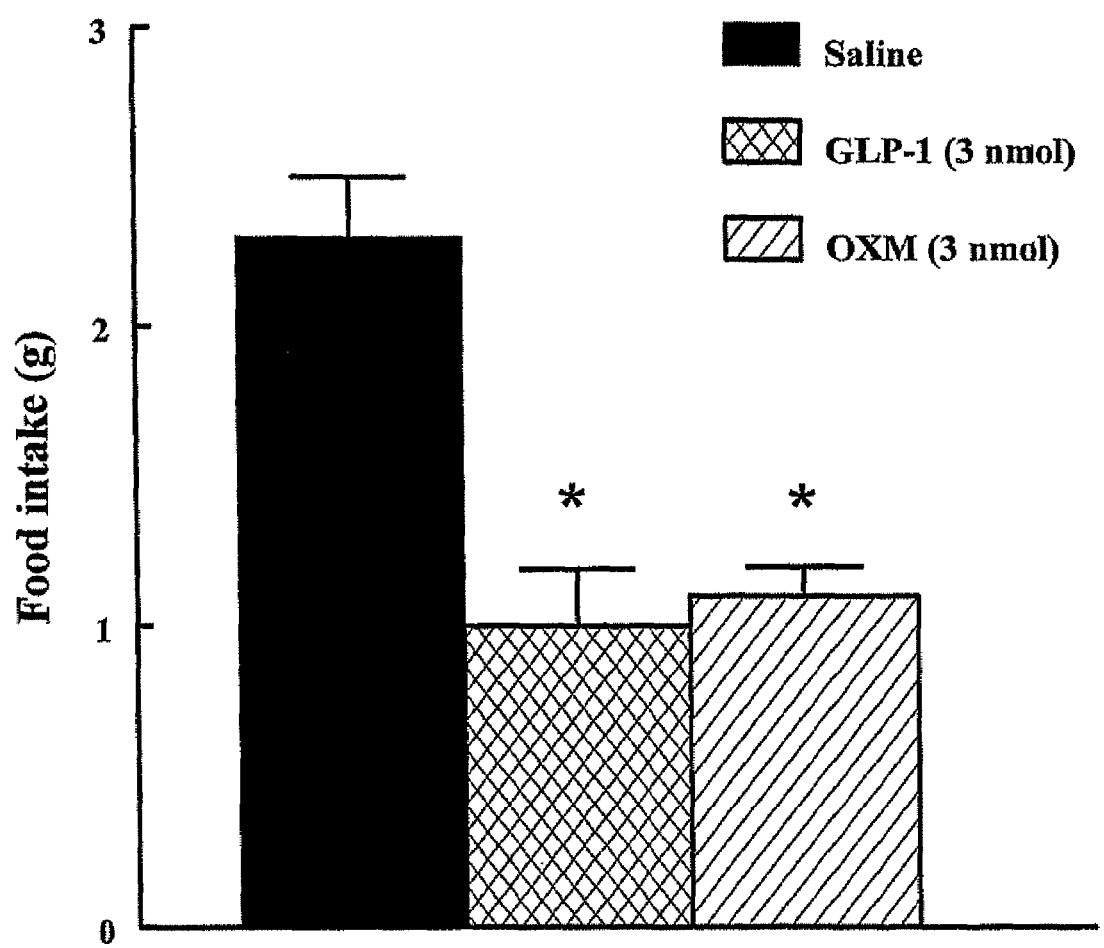
FIG. 3 shows two bar graphs of the effect of ICV OXM at the onset of the dark phase. Sated rats received an ICV injection of OXM, GLP-1 (3 nmol), or saline at the onset of the dark phase. Food intake (grams; A) and behaviors (B) at 1 h postinjection were determined. *, P<0/05 vs. saline control.

In study 3a, when injected in the early dark phase, both GLP-1 and OXM (3 nmol) significantly reduced food intake compared with that of saline-treated animals 1 h postinjection [FIG. 3A].

Observation of Behaviour after ICV Injection of OXM.

Figure 3B:
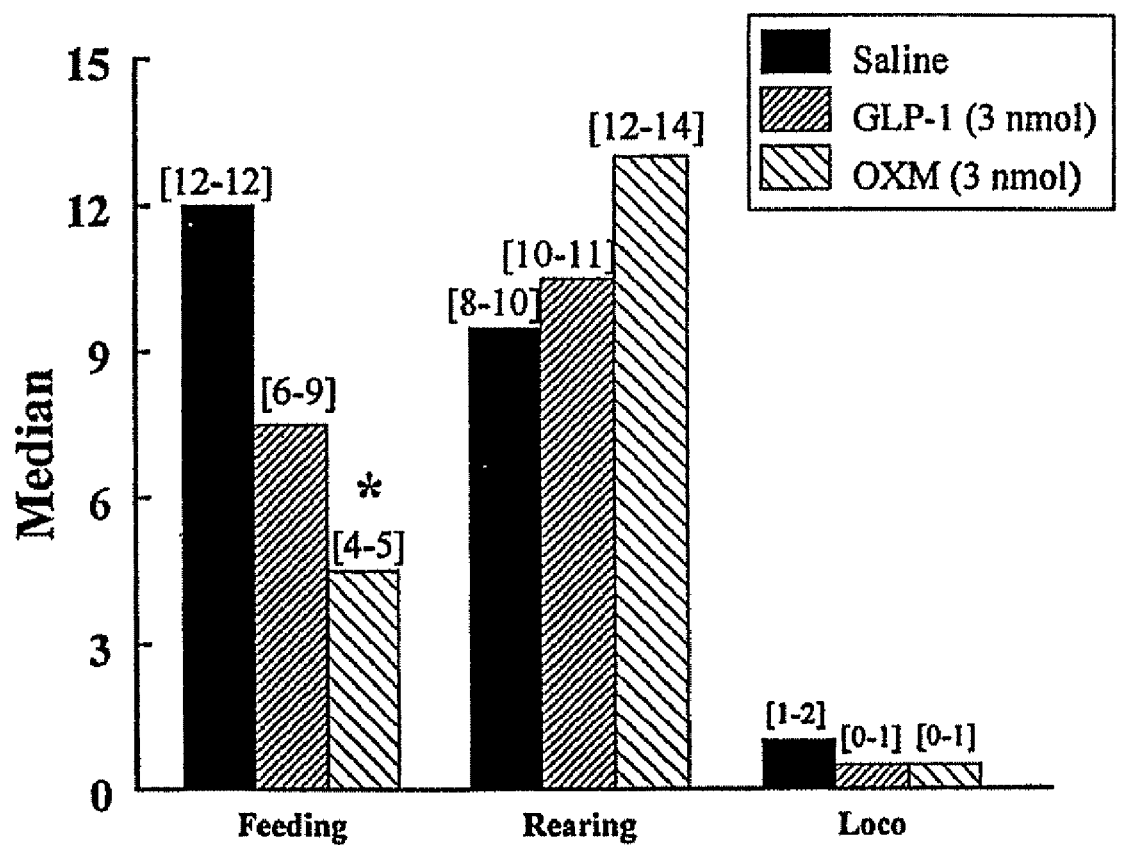

ICV administration of OXM (3 nmol) in the early dark phase led to a significant decrease in feeding episodes (study 3a) and an increase in rearing behaviour (study 3b) (FIG. 3B). There was no change in grooming, still, head down, burrowing, or locomotion episodes.

To assess whether OXM acts via the GLP-1 R, a study using the GLP-1 R antagonist, exendin-(9-39) was performed.

ICV Administration. Study 4.

Figure 4A:
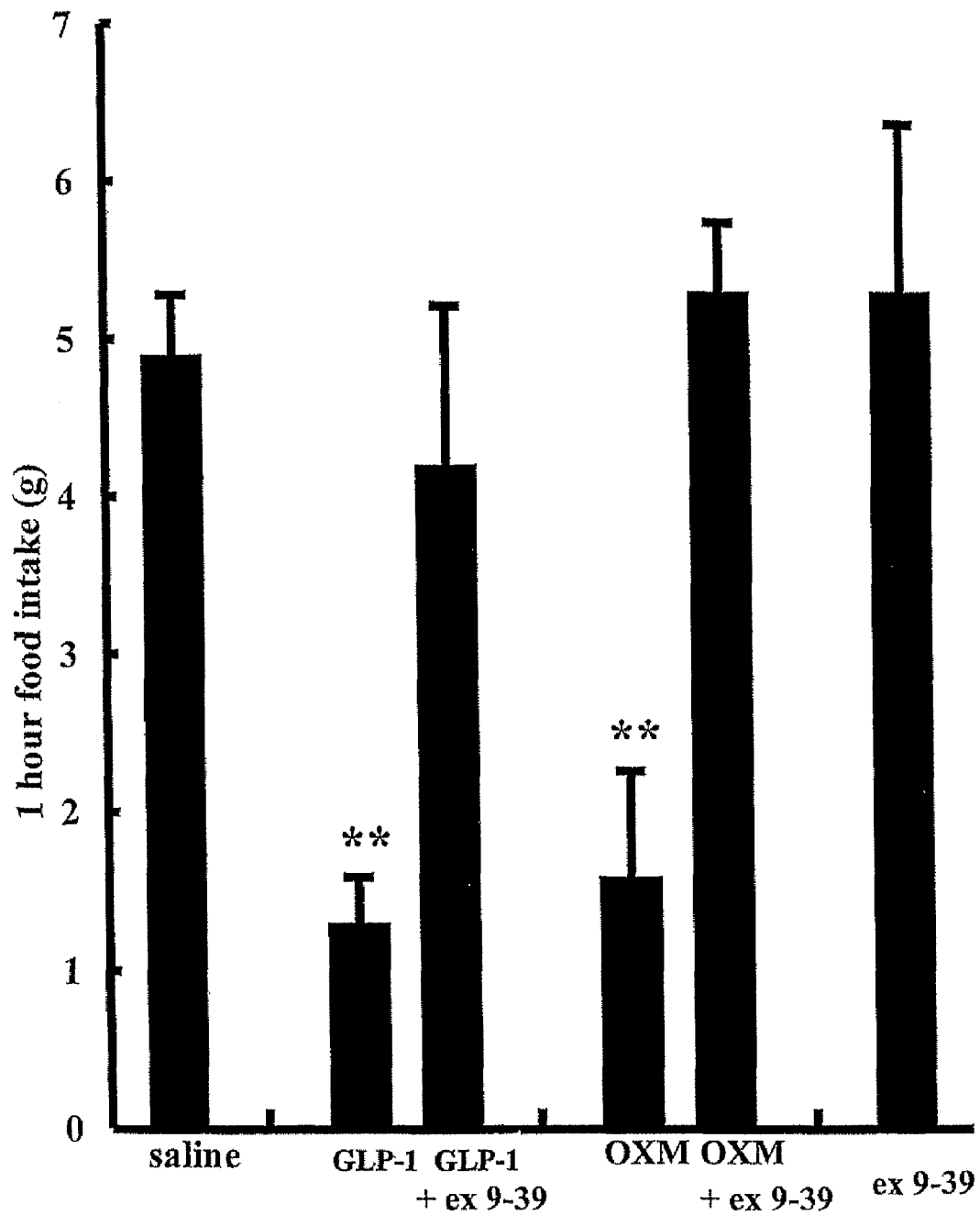
FIG. 4A, food intake 1 h after an acute ICV injection of GLP-1 (3 nmol), GLP-1 plus exendin-(9-39) (30 nmol), OXM (3 nmol), OXM and exendin-(9-39) (30 nmol), or exendin-(9-39) alone (30 nmol).

ICV coadministration of the GLP-1 receptor antagonist exendin-(9-39) with GLP-1 at a ratio of 10:1 (antagonist/agonist) blocked the anorectic effects of GLP-1 [FIG. 4A]. Furthermore, coadministration of exendin-(9-39) with OXM resulted in attenuation of the anorectic effect of OXM [FIG. 4A].

iPVN Administration.

Figure 4B:
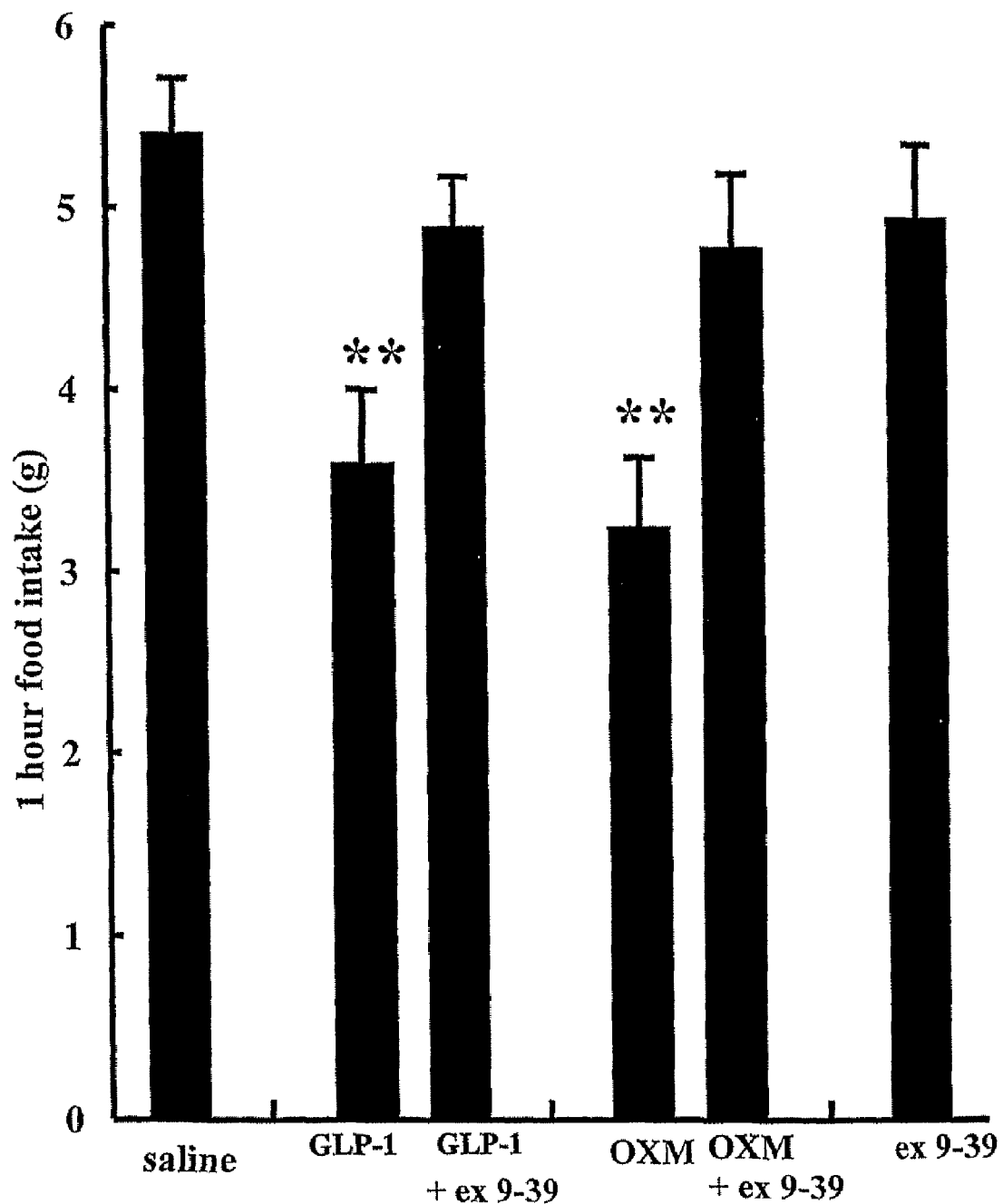
FIG. 4B, food intake after an acute iPVN injection of GLP-1 (1 nmol), GLP-1 and exendin-(9-39) (10 nmol), OXM (1 nmol), OXM and exendin-(9-39) (10 nmol), or exendin-(9-39) alone (10 nmol) into fasted animals. **, P<0.005 vs. saline control.

Similarly, when injected iPVN, the anorectic effects of both GLP-1 and OXM were blocked when coinjected with exendin-(9-39) [FIG. 4B].

Receptor Binding Assays. Study 5.

Figure 5:
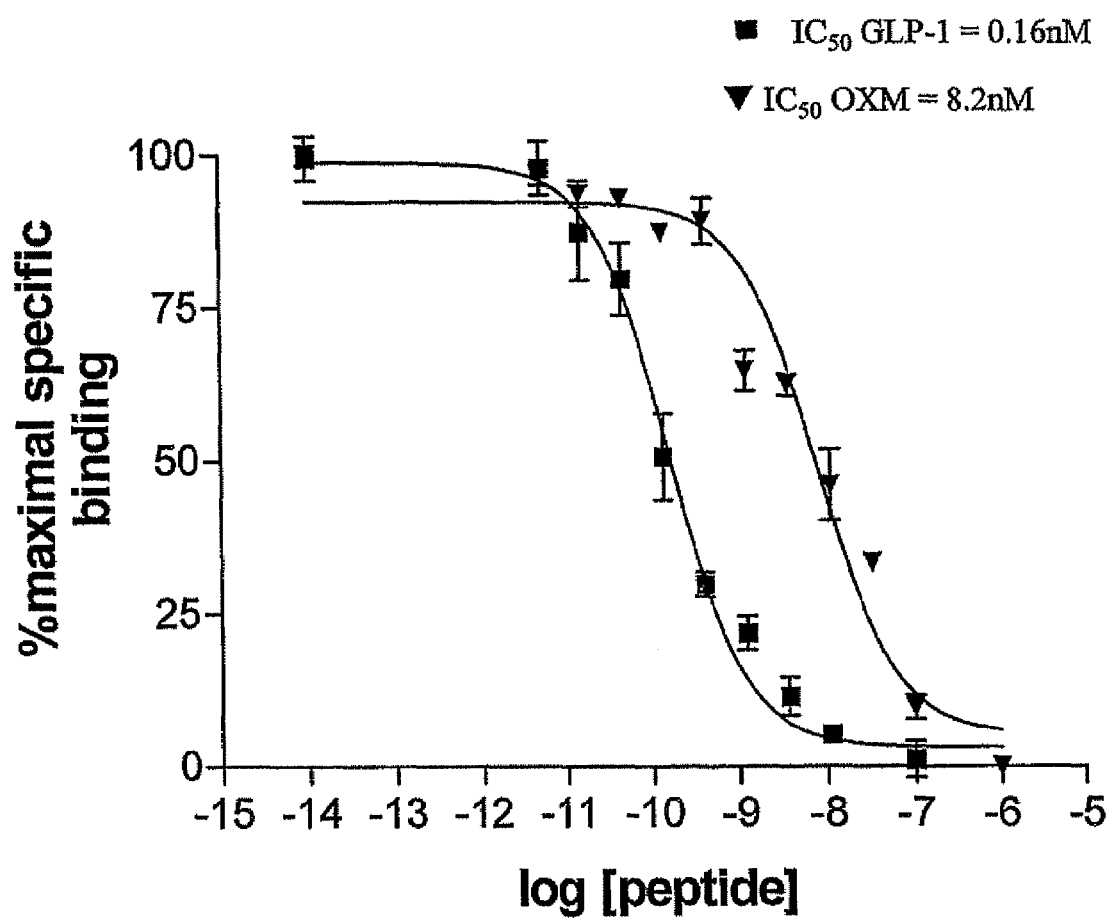
FIG. 5 is a graph of the competition of [$^{125}$I] GLP-1 binding in rat hypothalamic membranes by GLP-1 and OXM.

The affinity ($IC_{50}$) of GLP-1 for the GLP-receptor in rat hypothalamic membrane preparations was 0.16 nM (FIG. 5). The affinity of OXM for the GLP-1 receptor in the same membrane preparations was 8.2 nM (FIG. 5), which is approximately 2 orders of magnitude weaker than that of GLP-1.

Discussion.

OXM causes a potent decrease in fasting-induced refeeding when injected both ICV and iPVN. The effect was sustained until 8 h (iPVN) or 4 h (ICV) postinjection. The effect of OXM is approximately of the same magnitude and time course as that of GLP-1 when administered ICV and iPVN at equimolar doses. In addition, OXM inhibits food intake in nonfasted rats at the onset of the dark phase, and at that time they showed no signs of aversive behaviour.

It has been suggested that there is an OXM-specific binding site in gastric mucosa. However, no such binding site has been identified in the CNS. Therefore, it was proposed that OXM mediated its effects via the hypothalamic GLP-IR, as GLP-1 and OXM have similar potency in feeding studies. It has been shown that OXM has a nanomolar affinity for the GLP-IR ($IC_{50}$=8.2 nM). This affinity is approximately 2 orders of magnitude weaker than that of GLP-1 ($IC_{50}$=0.16 nM). Yet despite this reduced affinity for the GLP-1R, OXM reduces food intake to the same magnitude. One explanation for this is that OXM might act through both the GLP-1R and its own receptor in the hypothalamus. Thus, OXM could elicit a response comparable to that of GLP-1 despite its lower affinity for the GLP-IR.

Exendin-(9-39), a fragment of the GLP-1R agonist exendin-4, is a potent and selective antagonist at the CLP-1R. When GLP-1 and exendin-(9-39) are coinjected, the anorectic actions of GLP-1 are blocked. When OXM is coinjected with exendin-(9-39), the anorectic effects of OXM are also completely blocked. This would strengthen the argument that OXM is mediating its effects via the GLP-1R.

We investigated the effects of glicentin, and glucagon after an acute ICV injection in fasted rats. No effect on fasting-induced food intake was seen after the administration of these peptides. In addition, there was no effect of these peptides when they were administered iPVN. When SP-1, the putative minimal active structure of OXM, was injected iPVN, no inhibition of food intake was observed. Therefore the effect seen by OXM is specific.

Example 2

Peripheral Administration of OXM Also Reduces Food Intake and Body Weight

Peptides and Chemicals

OXM was purchased from IAF BioChem Pharma (Laval, Canada). GLP-1 was purchased from Peninsula Laboratories Inc. (St. Helens, UK). Exendin 9-39 was synthesised at Medical Research Council, Hemostasis Unit, Clinical Sciences Centre, Hammersmith Hospital, London, UK using F-moc chemistry on a 396 MPS peptide synthesizer (Advanced ChemTech Inc., Louisville, Ky.) and purified by reverse phase HPLC on a $C_8$ column (Phenomex, Macclesfield, UK), using a gradient of acetonitrile on 0.1% trifluoroacetic acid. Correct molecular weight was confirmed by mass spectrometry. All chemicals were purchases from Merck Eurolab Ltd. (Lutterworth, Leicestershire, UK), unless otherwise stated.

Animals

Adult male Wistar rats (180-200 g) were maintained in individual cages under controlled conditions of temperature (21-23° C.) and light (12 hours light, 12 hours dark) with ad libitum access to standard rat chow (RM1 diet, Special Diet Services UK Ltd., Witham, Essex, UK) and water. All procedures undertaken were approved by the British Home Office Animals (Scientific Procedures) Act 1986 (Project Licenses PPL: 90/1077, 70/5281 and 70/5516).

Intra-Arcuate Nucleus Cannulation

Animals had permanent indwelling, unilateral, stainless steel guide cannulae (Plastics One, Roanoke, Va.) stereotactically implanted into the arcuate nucleus of the hypothalamus, using a cannulation protocol using cannulae positioned 3.3 mm posterior to and 0.3 mm lateral to bregma and 9.0 mm below the outer surface of the skull.

Intra-Peritoneal (IP) Injections

All IP injections were delivered using a 1 ml syringe and a 25 gauge needle. The maximum volume of injection was 500 µl, and was adjusted according the weight of the individual animal. All peptides were dissolved in saline.

In these studies, the human OXM and human GLP-1 were used with the sequences provided on pages 15 and 16 above.

In Vivo Protocols

1. Investigating the Dose-Response Effect of Peripheral Administration of OXM on Food Intake in Fasted Animals:

Animals were fasted for 24 hours prior to the study. During the early light phase (09.00-10.00 hr), rats were given a single IP injection of saline, GLP-1 (30 nmol/kg body weight as a positive control) or OXM (10-300 nmol/kg body weight) (n=12 per group) in a volume of 500 µl. Following the injection, the animals were returned to their home cages and provided with a pre-weighed amount of chow. Food intake was measured 1, 2, 4, 8 and 24 hours post-injection.

2. Investigating the Effect of Peripheral Administration of OXM on Food Intake in Non-Fasted Animals During the Dark Phase:

The dark phase is the "normal" feeding time for rats. Therefore, any inhibition of food intake at this time could be considered to be more physiological than alterations to reseeding following a fast. Animals received a single IP injection of saline or OXM (3-100 nmol/kg body weight) (n=12 per group) prior to lights out (18.00-19.00 hr). Food intake was measured 1, 2, 4, 8 and 12 hours post-lights-out.

3. The Effect of Repeated IP Injections of OXM

45 Animals were randomised by weight into three groups (n=15 per group): 1) Saline-treated with ad libitum access to food, 2) OXM-treated (50 nmol/kg body weight per injection—a dose based on the previous dose-response experiment) with ad libitum access to food, 3) Saline-treated, but food restricted to the mean light and dark phase food intake of the OXM-treated group. Animals were injected twice daily (07.00 and 18.00 hr) for seven days. Food intake (g), body weight (g) and water intake (ml) were measured daily. On the eighth day, the animals were killed by decapitation. Epididymal white adipose tissue (WAT) and interscapular brown adipose tissue (BAT) were removed and weighed as an assessment of body adiposity.

4. Investigating the Effect of Peripheral Administration of OXM on Gastric Emptying Animals were fasted for 36 hours to ensure that the stomach was empty. During the early light phase (09:00-10:00) were allowed ad libitum access to a pre-weighed amount of standard rat chow for thirty minutes. After that time, the food was removed and reweighed. The animals were then IP injected with saline, OXM (50 nmol/kg body weight) or CCK-8 (15 nmol/kg body weight). Rats were then killed at the same times as those used in the previous feeding studies: 1, 2, 4 or 8 hours post-feeding (n=12 per group per timepoint). The CCK-8 group was used as a positive control for the experiment at the two-hour time-point only. Animals were killed by carbon dioxide asphyxiation. A laparotomy was rapidly performed and the stomach exposed. The pyloric junction was ligated (2.0 Mersilk, Johnson & Johnson, Belgium), followed by ligation of the gastro-oesophegeal junction and the stomach was removed. The gastric contents were then removed, placed in a pre-weighed weighing boat and left to air-dry for 48 hours. Once dry, the contents were weighed and the percentage of the chow ingested during the half-hour re-feeding period remaining in the stomach per rat was then calculated using the following formula:

$$\% \text{ food remaining in the stomach} = \frac{\text{dry weight of stomach content}}{\text{weight of food ingested}} \times 100$$

5. Investigating the Effect of Increasing Doses of Intra-Arcuate OXM

Intra-arcuate (Intra-ARC (iARC)) cannulated rats (n=12-15 per group) were randomised by weight into 6 groups. During the early light phase (0900-1000), 24-hour fasted rats received an iARC injection of saline, OXM (0.01, 0.03, 0.1, 0.3 or 110 nmoles). Food intake was measured 1, 2, 4, 8 and 24 hours post-injection.

6. Investigating Whether Peripherally Administered OXM is Acting Directly Via Arcuate Nucleus GLP-1 Receptors.

Rats cannulated into the arcuate nucleus were randomised into 6 groups (n=10-12 per group). During the early light phase (0900-1000) 24-hour fasted rats received an iARC injection of saline or exendin$_{9-39}$ (5 nmoles) followed by an IP injection of saline, OXM (30 nmoles/kg body weight) or GLP-1 (30 nmoles/kg body weight) 15 minutes later. The injection details are described in Table 1 below.

TABLE 1

| Group | Intra-ARC injection | IP injection |
|---|---|---|
| 1 | Saline | Saline |
| 2 | Saline | OXM (30 nmoles/kg) |
| 3 | Saline | GLP-1 (30 nmoles/kg) |
| 4 | Exendin 9-39 (5 nmoles) | Saline |
| 5 | Exendin 9-39 (5 nmoles) | OXM (30 nmoles/kg) |
| 6 | Exendin 9-39 (5 nmoles) | GLP-1 (30 nmoles/kg) |

Immunohistochemistry 90 minutes after an IP injection of OXM (50 nmol/kg), CCK (15 nmol/kg) or saline, rats were terminally anaesthetized was transcardially perfused with 0.1 M phosphate buffered saline (PBS) following by 4% PB-formalin (PBF). The brains were removed and post-fixed overnight in PBF and then transferred to PB-sucrose (20% w/v) overnight. 40 µm coronal sections of brain and brainstem were cut on a freezing microtome and stained for fos-like immunoreactivity (FLI) by the avitin-biotin-peroxidase method. The sections were then mounted on poly-L-lysine-coated slides, dehydrated in increasing concentrations of ethanol (50-100%), delipidated in xylene and coverslipped using DPX mountant. Slides were examined for FLI-positive nuclei using a light microscope (Nikon Eclipse E-800) and images captured using a microimager (Xillix MicroImager). The numbers of FLI-positive nuclei in the hypothalamus and brainstem were counted by an independent member of the research team who was blinded to the experimental groups. The average number of FLI-positive nuclei per section was calculated and expressed as an integer for each animal.

Hypothalamic Explant Static Incubation

A static incubation system was used. Male Wistar rats were killed by decapitation and the whole brain removed immediately. The brain was mounted, ventral surface uppermost, and placed in a vibrating microtome (Microfield Scientific Ltd., Dartmouth, UK). A 1.7 mm slice was taken from the basal hypothalamus, blocked lateral to the Circle of Willis and incubated in chambers containing 1 ml of artificial cerebrospinal fluid which was equilibrated with 95% $O_2$ and 5% $CO_2$. The hypothalamic slice encompassed the medial preoptic area, PVN (paraventricular hypothalamic nucleus), dorsomedial nucleus, ventromedial nucleus, lateral hypothalamus and ARC. The tubes were placed on a platform in a water bath maintained at 37° C. After an initial 2-hour equilibration period, each explant was incubated for 45 minutes in 600 µl aCSF (basal period) before being challenged with a test period. OXM, 100 nM was used as a dose representing a concentration ten times that of its $IC_{50}$ for the GLP-1 receptor. The viability of the tissue was confirmed by a final 45-minute exposure to aCSF containing 56 mM KCl. At the end of each experimental period, the aCSF was removed and stored at −20° C. until measurement of αMSH-immunoreactivity by radioimmunoassay.

Radioimmunoassay to Measure αMSH-IR

Alpha-MSH was measured using an in-house radioimmunoassay, developed using an antibody from Chemicon International Inc.

Statistical Analysis

Data from IP and iARC feeding studies were analyzed by ANOVA with post-hoc LSD (least significant difference) test. Fat pad weights from different treatment groups were analyzed using an unpaired t test. Data from the hypothalamic explant incubation study, in which each explant was compared with its own basal period, were analyzed by paired t test. In all cases P<0.05 was considered to be statistically significant.

Results

1. The Effect of Peripheral Administration of OXM In Fasted Animals

Figure 6A:
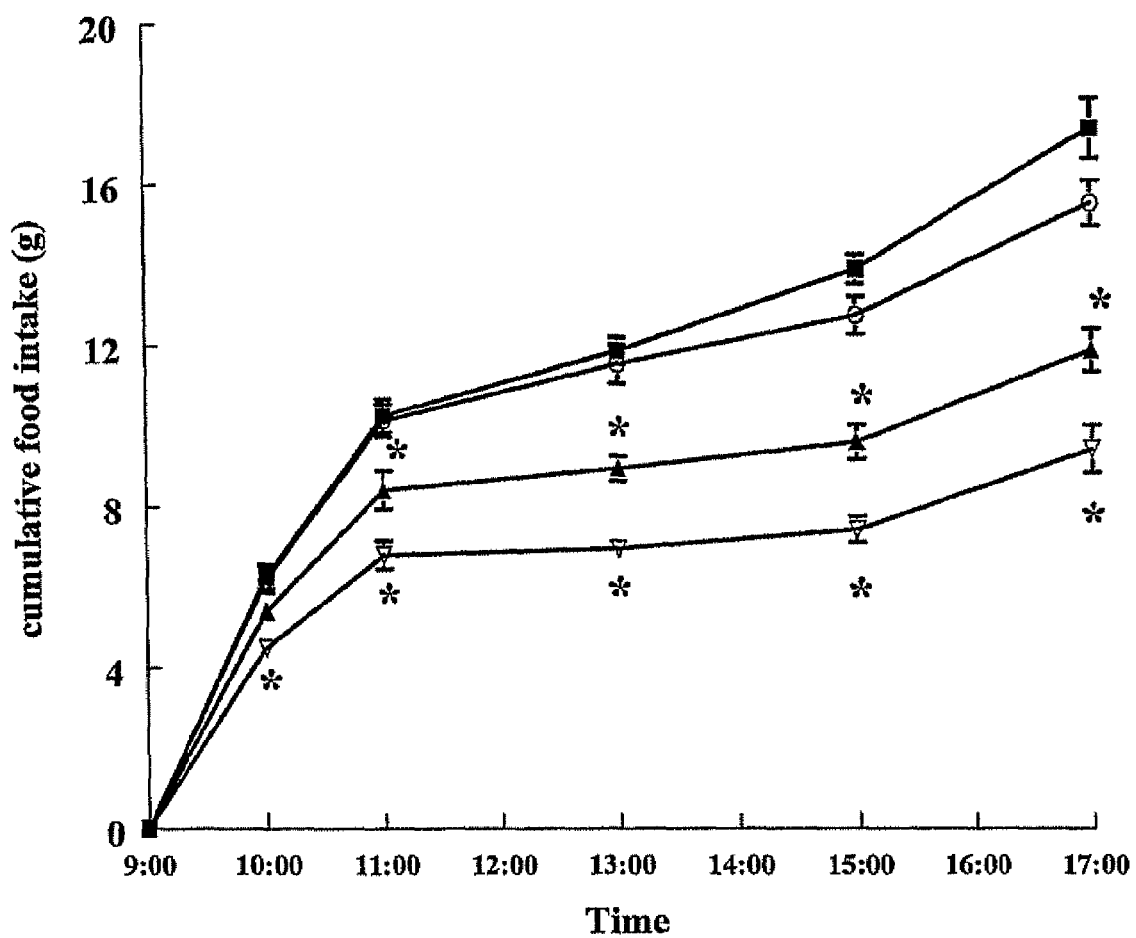
FIG. 6 illustrates the effect of a) IP OXM (30, 100 and 300 nmol/kg in 500 µl saline) or saline on cumulative food intake (g) in 24-hour fasted rats injected during the early dark phase (closed squares=saline, open circles=OXM 30 nmol/kg, closed triangles=OXM 100 nmol/kg, open triangles=OXM 300 nmol/kg); and b) IP OXM (30 and 100 nmol/kg in 500 µl saline) or saline on cumulative food intake in non-fasted rats injected prior to the onset of the dark phase (closed squares=saline, open circles=OXM 30 nmol/kg, closed triangles=OXM 100 nmol/kg). *P<0.05 vs. saline.

Intraperitoneal administration of OXM (100 nmol/kg and 300 nmol/kg) caused a significant inhibition in refeeding in 24-hour fasted animals one hour post-injection, compared with saline controls (1 hour: OXM 100 nmol/kg, 5.4±0.2 g (P<0.05), 300 nmol/kg, 4.5±0.2 g (P<0.05) vs. saline, 6.3±0.2 g). The reduction in food intake caused by 100 nmol/kg was sustained until 8 hours post-injection. However, the highest dose of OXM (300 nmol/kg) continued to significantly inhibited food intake 24 hours post-injection (8 hours: OXM, 300 nmol/kg, 9.5±0.6 g vs. saline, 17.5±0.7 g; P<0.05) (FIG. 6a). The 30 nmol/kg and 10 nmol/kg failed to alter food intake at any time-point investigated.

Figure 6B:
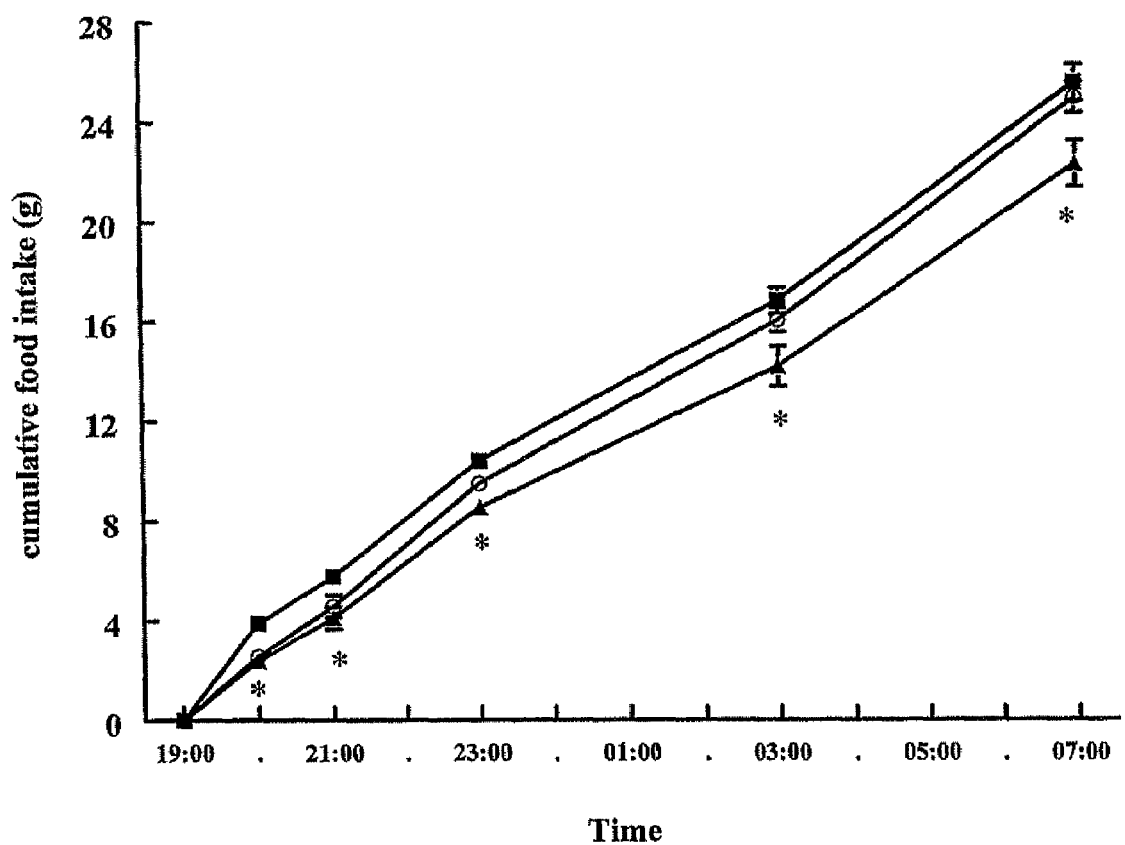

2. The Effect of Peripheral Administration of OXM in Non-Fasted Animals on Dark Phase Food Intake:

OXM, 3 and 10 nmol/kg, failed to affect food intake at any time-point investigated in nocturnally feeding rats injected immediately prior to the dark phase. However, OXM, 30 nmol/kg, significantly inhibited food intake until 2 hours post-injection (2 hours. OXM, 30 nmol/kg, 4.5±0.4 g vs. saline, 5.8±0.4 g; P<0.05). Food intake was reduced 4 hours post-injection, but this was not significant. OXM, 100 nmol/kg, significantly inhibited food intake throughout the dark phase (8 hours: OXM, 100 nmol/kg, 14.1±0.8 g vs. saline, 16.9±0.5 g; P<0.05) (FIG. 6b).

3. The Effect of Repeated IP Administration of OXM

Figure 7A:
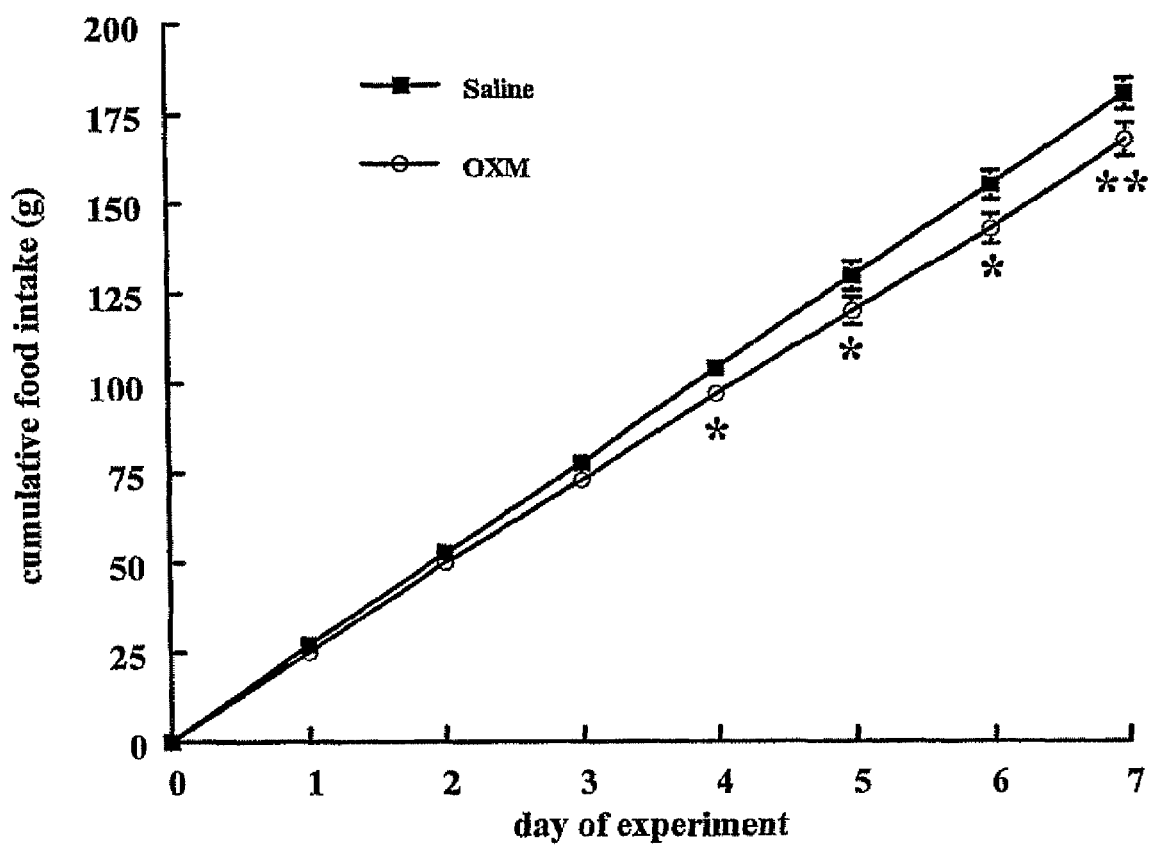
FIG. 7 illustrates the effect of twice daily IP injections of OXM (50 nmol/kg) or saline for seven days on a) cumulative food intake (g); and b) body weight gain (g). *P<0.05, P<0.01, *P<0.005 vs. saline.
Figure 7B:
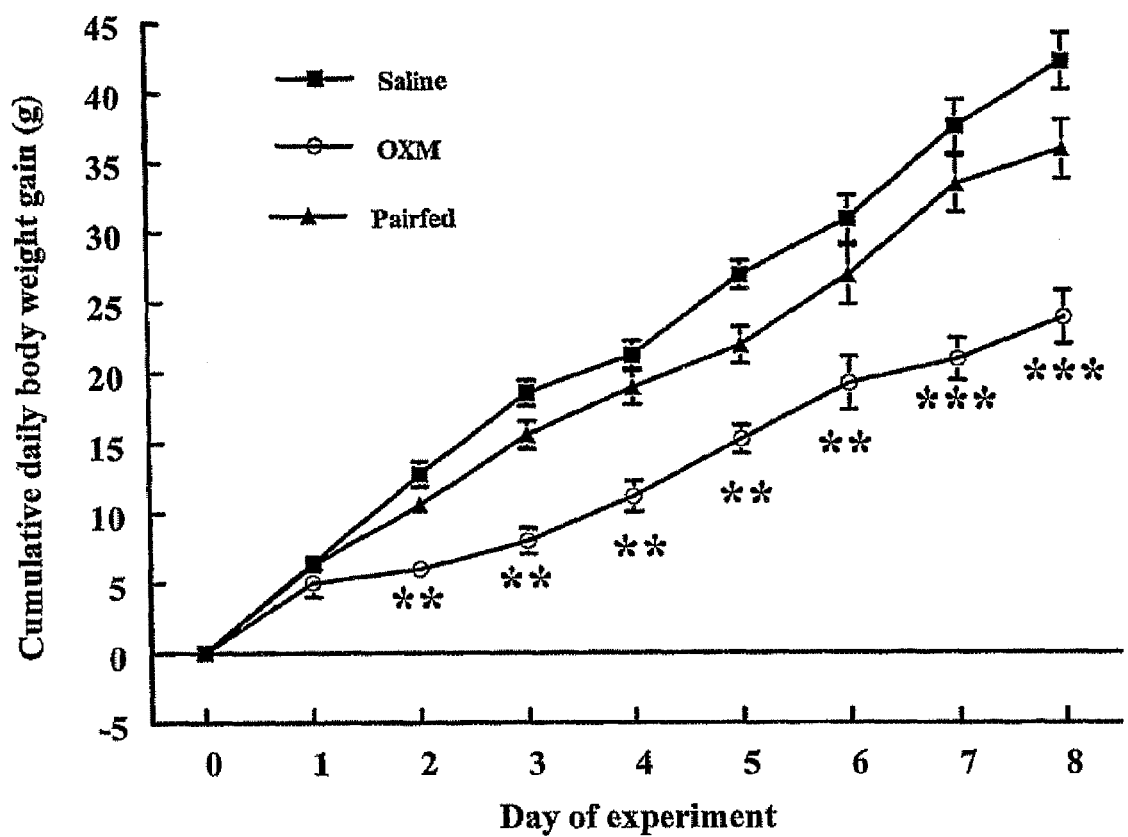

Twice-daily IP injections of OXM (50 nmol/kg) for seven days caused a significant decrease in cumulative daily food intake, compare with saline-treated control animals (Cumulative food intake day 7: OXM, 50 nmol/kg, 168±4.6 g vs. saline, 180±4.3 g; P<0.01) (FIG. 7a). Furthermore, OXM-treated animals gained weight significantly more slowly than saline controls (cumulative weight gain day 7: OXM, 50 nmol/kg, 21.0±1.5 g vs. saline, 37.6±1.9 g; P<0.005). Moreover, the food restricted "pair fed" animals did not gain weight as slowly as OXM-treated animals, despite receiving the same food intake (Day 7: pair fed, 33.5±2.0 g; P=NS vs. saline (ad libitum fed), P<0.05 vs. OXM) (FIG. 7b). In addition, chronic OXM caused a decrease in adiposity that was not seen in saline-injected pair fed animals (Table 2). Water intake was significantly reduced in OXM-treated animals on days 1 and 2 of the experiment (Day 1: OXM, 24.1±1.28 ml vs. saline, 28.1±1.33 ml; P<0.05). On subsequent days, there was an increase in daily water intake compared with saline-treated animals (days 3-6). However, by day 7, there was no difference in water intake between saline and OXM-treated groups (not shown). The body weight difference between the "pair fed" rats and the OXM treated rats is due to increased energy expenditure since the two groups ate the same amount of food.

TABLE 2

The effect of twice-daily IP administration of saline or OXM (50 nmol/kg) for seven days on the weight of epididymal WAT and interscapular BAT in food restricted and ad libitum fed rats.

| Tissue/hormone | Saline | OXM | Pairfed |
|---|---|---|---|
| WAT | 0.69 ± 0.02 | 0.51 ± 0.01$^a$ | 0.61 ± 0.02$^b$ |
| BAT | 0.16 ± 0.01 | 0.12 ± 0.01$^a$ | 0.15 ± 0.01$^b$ |

Figure 8:
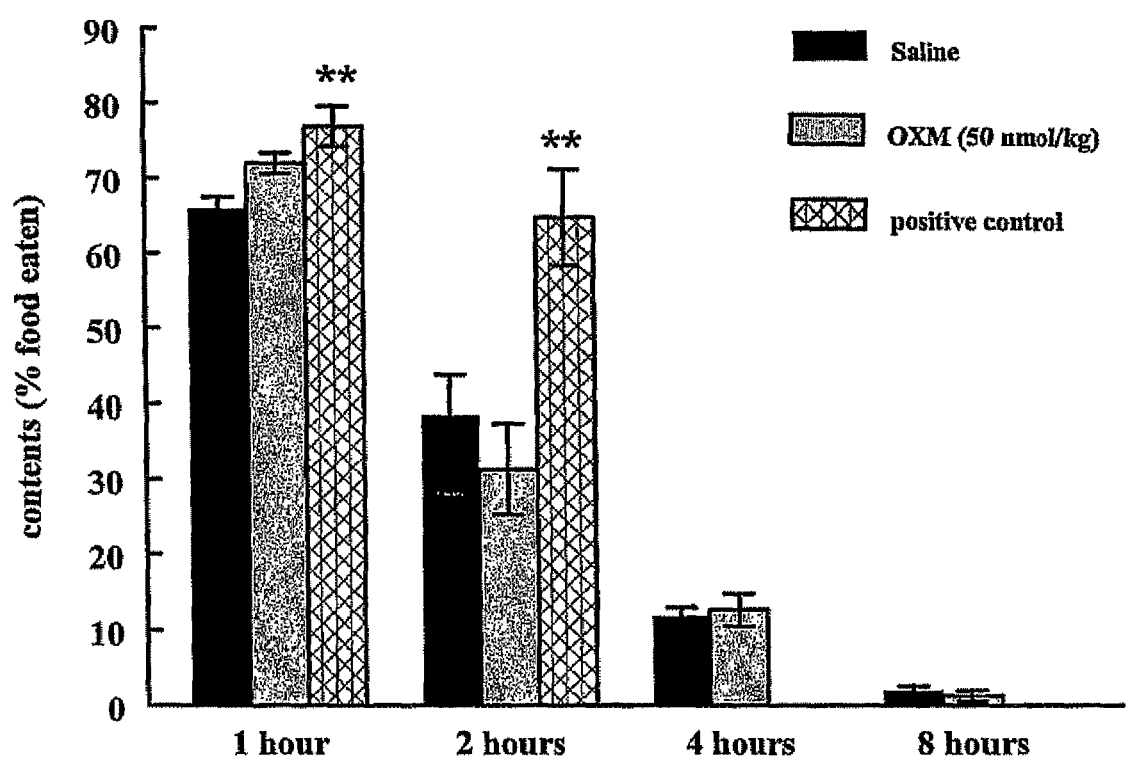
FIG. 8 illustrates the effect of IP OXM (50 nmol/kg), saline or a positive control (1 hour=GLP-1 (50 nmol/kg); 2 hours = CCK (15 nmol/kg)) on gastric emptying in 36-hour fasted rats. Contents (dry weight) of the stomach were expressed as a percentage of the food intake during the 30-minute feeding period. **P<0.01 vs. saline.

4. The Role of Delayed Gastric Emptying on the Anorectic Effect of OXM:

One hour after food was presented to the 36-hour fasted rats, the dry weight of the contents of the stomachs (as a percentage of the food consumed during the 30 minute feeding period) of GLP-1-treated animals were significantly greater than that of saline-treated animals (1 hour: GLP-1, 50 nmol/kg, 76.9±2.7 g vs. saline, 65.8±1.6 g; P<0.01), suggesting that GLP-1 caused a significant decrease in gastric emptying. The contents of the stomachs of OXM-treated animals were greater than those of the saline treated controls, although this was not statistically significant (1 hour: OXM, 50 nmol/kg, 72.0±1.4 g vs. saline 65.8±1.6 g; P=0.07). Two hours post-feed, OXM did not affect the contents of the stomach, compared with saline-treated animals. However, animals injected with the positive control for this time-point, CCK (15 nmol/kg), had significantly greater stomach content (2 hours: CCK, 15 nmol/kg, 64.7±6.4 g vs. saline, 38.5 g; P<0.01), suggesting that CCK caused a significant decrease in the rate of gastric emptying. There was no effect of OXM on the contents of the stomach, compared with saline-treated animals, at 4 or 8 hours post-feed (FIG. 8).

Figure 9:
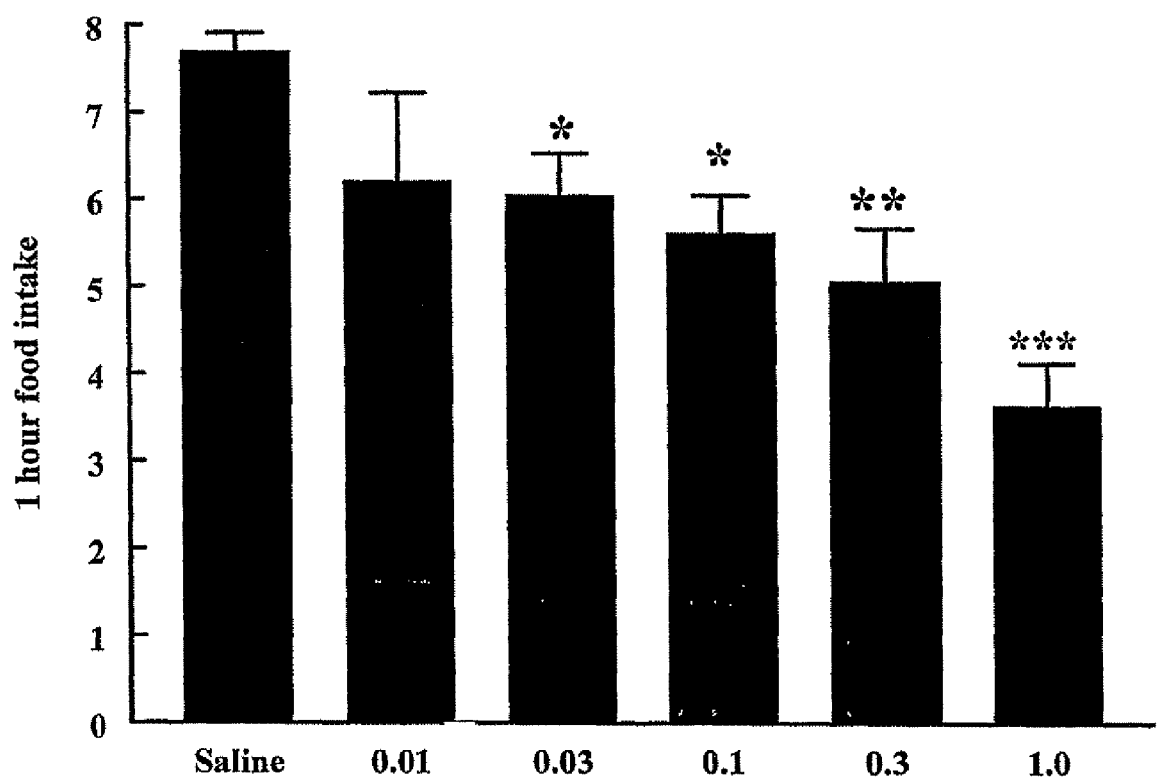
FIG. 9 illustrates the effect of increasing doses of OXM (0.01-1.0 nmole) on 1 hour food intake when administered into the arcuate nucleus of 24-hour fasted rats. *P<0.05, P<0.01, *P<0.05 vs. saline.

5. Investigating the Effect of Increasing Doses of OXM Injected Intra-Arcuate Nucleus Food intake was significantly inhibited by all doses (except 0.01 nmoles) of OXM administered iARC during the 1$^{st}$ hour of re-feeding following a 24-hour fast (1 hour: OXM 0.03 nmoles, 6.1±0.5 g (P<0.05); 0.1 nmoles, 5.6±0.4 g (P<0.05); 0.3 nmoles, 5.1±0.6 g (P<0.01); 1.0 nmole, 3.6±0.5 g (P<0.005) all vs. saline, 7.7±0.2 g) (FIG. 9). OXM 0.3 and 1.0 nmoles continued to significantly inhibit food intake until 8 hours post-injection. Twenty-four hours post-injection, food intake was inhibited by OXM 1.0 nmoles, although this was not significant (24 hours: OXM, 1.0 nmole, 37.8±3.0 g vs. saline, 40.8±1.6 g; P=NS).

Figure 10:
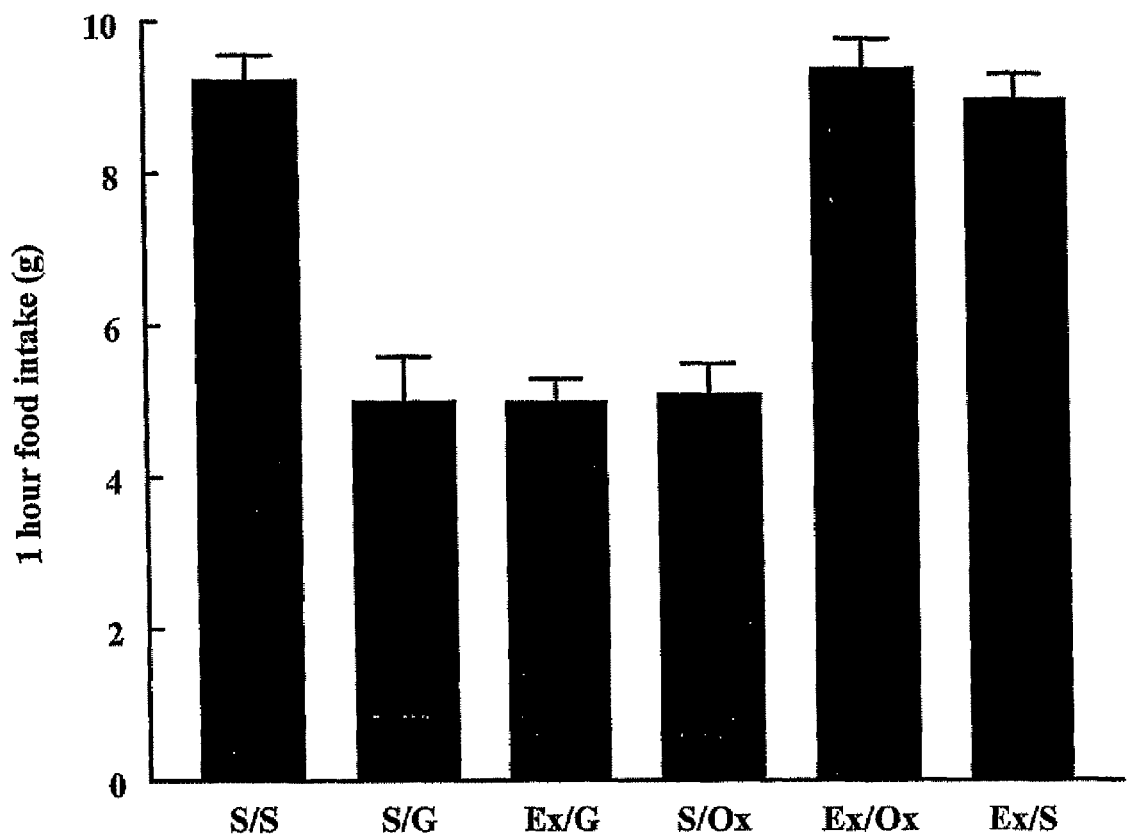
FIG. 10 illustrates the effect of iARC administration of exendin 9-39 (5 nmoles) or saline injected 15 minutes prior to IP administration of OXM (30 nmol/kg), GLP-1 (30 nmol/kg) or saline on 1 hour food intake (g). (S=saline, G=GLP-1 (30 nmol/kg), Ox=OXM (30 nmol/kg), Ex=exendin 9-39 (5 nmoles)).

6. Investigating Whether Peripherally Administered OXM is Acting Via Arcuate Nucleus GLP-1 Receptors Intraperitoneal administration of both GLP-1 (30 nmol/kg) and OXM (30 nmol/kg) caused a significant inhibition of food intake one hour into the dark phase (1 hour: GLP-1, 5.0±0.6 g, OXM, 5.1±0.4 g vs. saline, 9.2±0.3 g). However, the anorexia caused by IP administration of OXM was blocked by prior administration of the GLP-1 receptor antagonist, exendin 9-39 (300 nmol/kg), injected directly into the ARC (Table 3 & FIG. 10). Inhibition of food intake by IP GLP-1 was not affected by prior iARC administration of exendin 9-39.

TABLE 3

The effect of iARC administration of exendin 9-39 (5 nmoles) or saline injected 15 minutes prior to IP administration of OXM (30 nmol/kg), GLP-1 (30 nmol/kg) or saline on 1 hour food intake (g). (S = saline, G = GLP-1 (30 nmol/kg), Ox = OXM (30 nmol/kg), Ex = exendin 9-39 (5 nmoles)).

| Peptide | Food intake (g) | S.E.M. |
|---|---|---|
| Saline/saline | 9.2 | 0.3 |
| Saline/GLP-1 | 5.0 | 0.6 |
| Exendin 9-39/GLP-1 | 5.0 | 0.3 |
| Saline/OXM | 5.1 | 0.4 |
| Exendin 9-39/OXM | 9.4 | 0.4 |
| Exendin 9-39/saline | 9.0 | 0.3 |

Figure 11A:
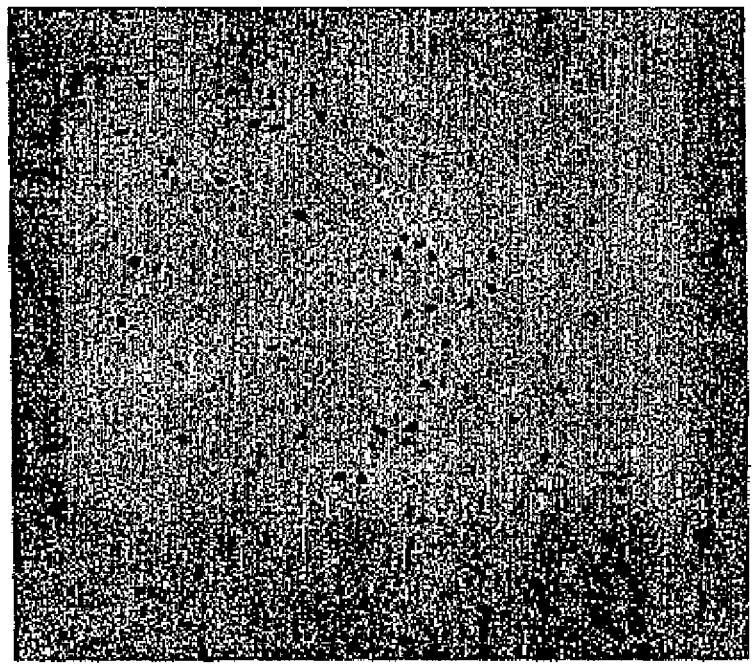
FIG. 11a illustrates the expression of fos-like immunoreactivity in response to A) IP saline or B) IP OXM (50 nmol/kg) in the arcuate nucleus of the hypothalamus (x40 magnification). ***P<0.005 vs. saline.
Figure 11A:
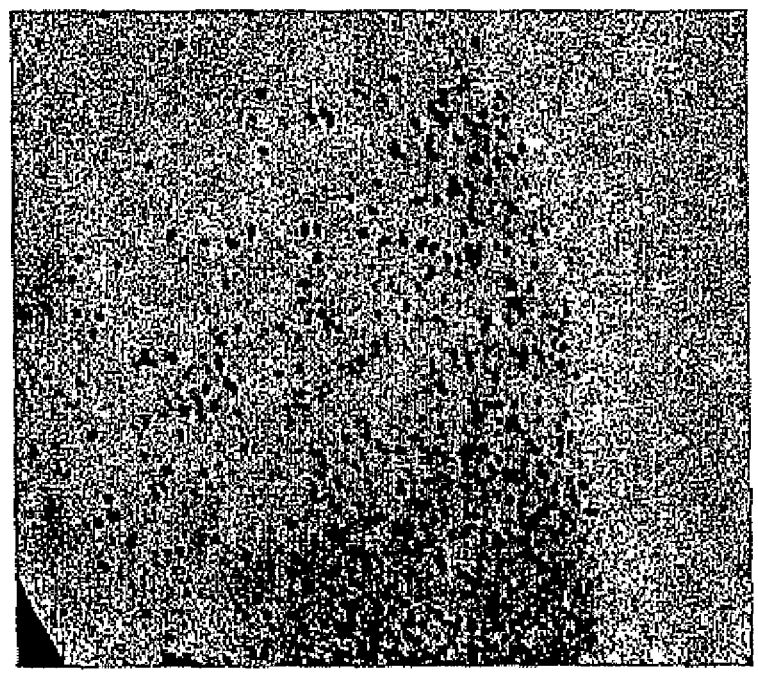

7. Mapping the Expression of FLI in the Hypothalamus in Response IP OXM:

After IP OXM administration (50 nmol/kg) dense staining of FLI was found almost exclusively in the hypothalamic arcuate nucleus (FIG. 11*a*). No other hypothalamic nuclei (PVN (paraventricular hypothalamic nucleus), DMH (dorsomedial hypothalamic nucleus), VMH (ventromedial hypothalamic nucleus)) demonstrated specific c-fos staining.

Figure 11B:
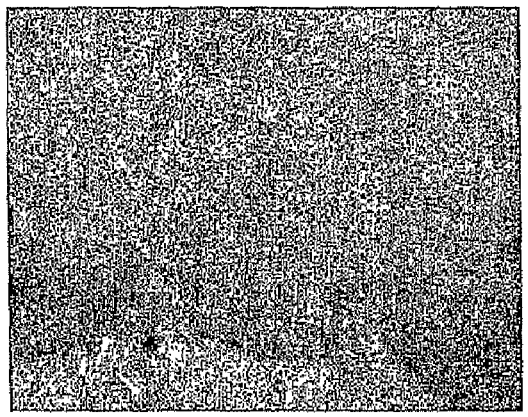
FIG. 11b illustrates the expression of fos-like immunoreactivity in response to A) IP saline, B) IP OXM (50 nmol/kg) or C) IP CCK (15 nmol/kg) in the NTS and AP of the brainstem.
Figure 11B:
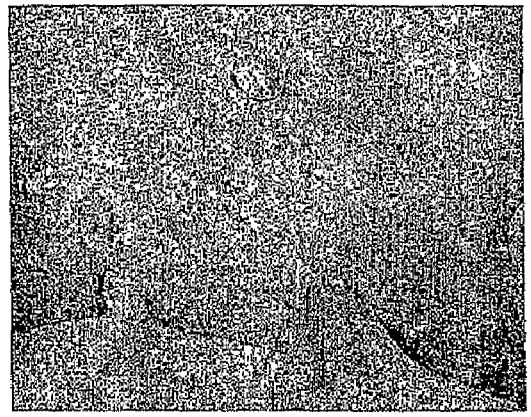
Figure 11B:
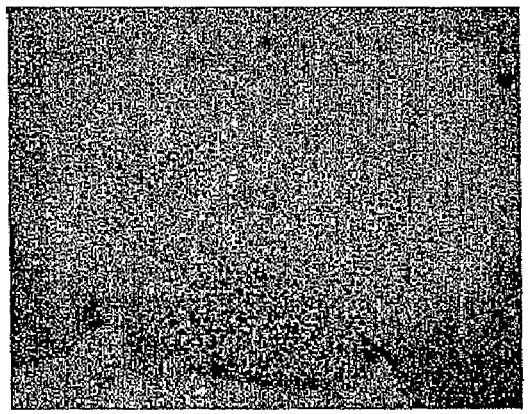

In the brainstem, IP CCK (15 nmol/kg) caused dense staining of FLI, most notably in the NTS (nucleus tractus solitarius) and the area postrema (FIG. 6*b*). However, neither IP saline nor IP OXM (50 nmol/kg) caused a specific increase in c-fos expression in the same brainstem nuclei investigated (FIG. 11*b*).

8. Changes in Alpha-MSH Release from Hypothalamic Explants when Incubated with OXM Incubating OXM (100 nM) was hypothalamic explants caused a significant increase in the release of α-MSH, compared with basal release (α-MSH: OXM, 100 nM, 4.1±0.6 fmol/explant vs. 2.6±0.5 fmol/explant; P<0.005). Explant viability was assessed by incubation with 56 mM KCl, and viability was confirmed in >80% of explants. Those explants that were not viable were excluded from the analysis.

Discussion

Peripheral administration of OXM causes a reduction in food intake in rats. This was seen following a fast in the light phase and during the nocturnal feeding phase. The anorectic effect was potent and sustained for periods up to 24 hours. Twice-daily IP administration of OXM for seven days caused a reduction in daily food intake compared with those treated with saline, with no tachyphylaxis. Animals treated with OXM gained significantly less weight than pair fed animals, despite the two groups receiving identical daily caloric intake. Intraperitoneal administration of OXM did transiently reduce water intake although this was not sustained, suggesting that the reduction in the rate of body weight gain was not due to dehydration. On conclusion of the chronic study, epididymal WAT and interscapular BAT were removed and weighed. It was found that there was a reduction in the weights of all fat pads in OXM-treated animals compared with pair-fed animals, despite identical food intake. Therefore it appears that peripheral OXM administration is also affecting other metabolic parameters.

A major contributor to satiety is delayed gastric emptying via vagally-mediated mechanism that leads to brainstem activation. Both GLP-1 and OXM are potent inhibitors of gastric emptying in rodents and humans and in the case of GLP-1, this is thought to be the dominant mechanism through which it promotes satiety. We hypothesized that OXM was acting in the same way, and that its effects on gastric emptying were the cause of sustained anorexia. However, although peripheral administration of OXM led to a slight delay in gastric emptying in the first hour after the re-introduction of food, this was non-significant and the effect was short-lived. This suggested that OXM does slow gastric emptying, but it is not likely to be responsible for the robust and sustained inhibition of food intake.

We report here that peripheral administration of OXM increases FLI in almost exclusively in the ARC. Furthermore, we found that incubating hypothalamic explant with OXM caused a significant increase in the release of the POMC (pro-opiomelanocortin)-derived product, αMSH from hypothalamic explants. IP OXM did not affect the expression of FLI in the NTS and AP—areas known to be important in integrating vagally mediated information, further strengthening the notion that OXM is not acting via these pathways.

It is thought that nuclei in the brainstem are the primary site of GLP-1 action, and information is subsequently relayed to the hypothalamic PVN, where its anorectic effects are mediated. Direct injection of OXM into the ARC, even at very low doses caused a robust and sustained inhibition of food intake, further supporting the hypothesis that that the ARC is the site of the actions of OXM. Anorectic effects caused by peripheral administration of OXM were blocked by prior administration of exendin 9-39 into the ARC. Interestingly, however, the anorectic actions of peripherally administered GLP-1 were not. This finding strongly indicates that OXM is acting via GLP-1 receptors in the ARC. In addition, it has identified distinct pathways which mediate the actions of GLP-1 and OXM.

Taken together, these data demonstrate that OXM is potentially important in both long and short-term regulation of food intake and body weight maintenance. Rather than reducing appetite via "traditional" satiety pathways, involving slowing of gastric emptying and activation of brainstem nuclei, circulating OXM is mediating its anorectic effects via direct interaction with the ARC, potentially by activating POMC (pro-opiomelanocortin) neurons within the nucleus. Therefore, OXM may be useful in the treatment or prevention of excess weight such as obesity in mammals, and further represents a novel target for the development of therapeutic agents in the treatment of excess weight such as obesity in mammals.

Example 3

Investigation of The Effect of OXM Infusion on Food Intake in Human Subjects

Methods

Study 1

Figure 12:
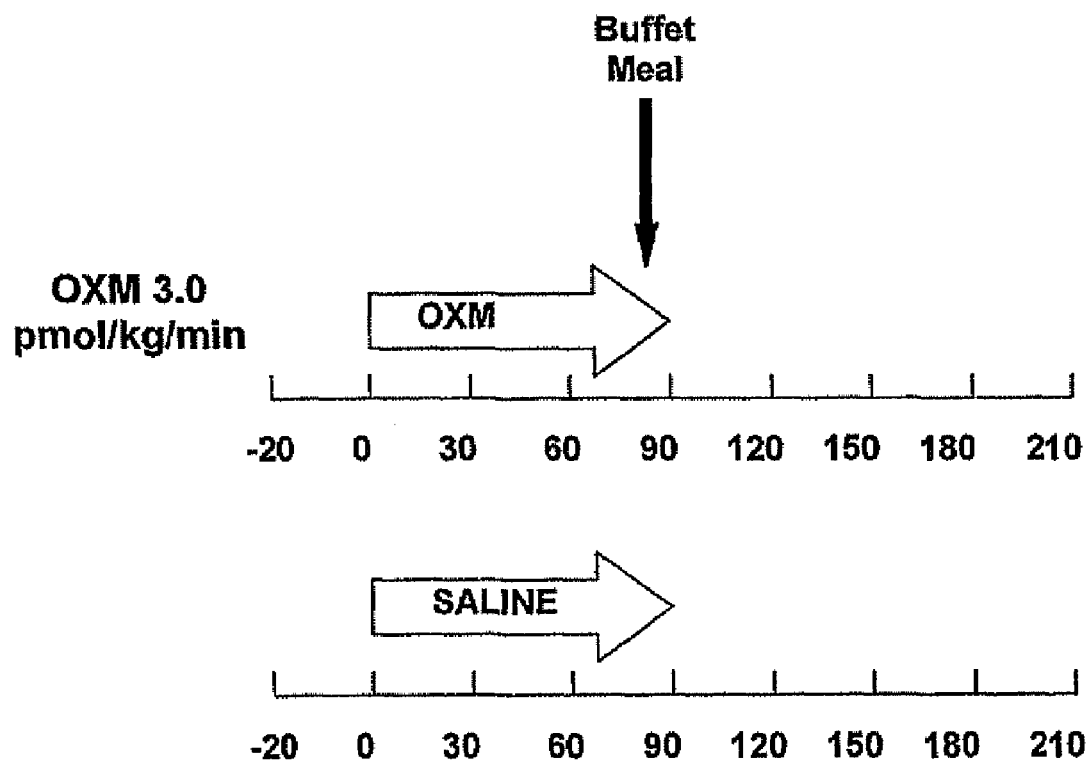
FIG. 12 shows the protocol of the study of the effect of intravenous infusion of OXM on food intake in human subject. The scale represents time (min) Infusion of OXM (3.0 pmol/kg/min) and saline was from 0-90 minutes. The buffet meal was presented at 75 minutes.

The study design was a double-blind placebo-controlled crossover, see FIG. 12. 13 healthy volunteers (age 27±2 yrs; BMI 25.3±0.7 $kg^{-2}$) received a 90 minute intravenous infusion of OXM (3.0 pmol/kg/min) and an infusion of saline≧1 week apart, in random order OXM was dissolved in saline containing haemaccel (5% by volume) to reduce adsorption to the syringe and tubing. Volunteers completed a food diary for three days prior to each infusion and for the subsequent 24 hours. Subjects were instructed to follow a similar diet on the days preceding each infusion. They consumed an identical meal (of their choice) on the night before each infusion and fasted from 9 pm.

On each study day intravenous cannulae were inserted bilaterally into arm veins, one for administration of the infusion, while the other was used for blood-sampling. Subjects were attached to a cardiac monitor and blood pressure was measured every 15 min. Blood samples were collected every 30 minutes into Lithium-Heparin tubes (LIP LTD, UK) containing 5,000 Kallikrein Inhibitor Units (0.2 ml) of aprotinin (Trasylol, Bayer) and stored on ice. Following centrifugation plasma was immediately separated and stored at −70° C. until analysis.

15 min before termination of the infusion, subjects were offered a buffet meal which was provided in excess so that all appetites could be satisfied and subjects would be unable to assess their own food intake. The choices consisted of chicken curry, plain boiled rice, fruit salad, and a variety of mini chocolate bars and fruit-flavoured sweets. Water was freely available. Dietary intake was calculated by weighing food and water pre and postprandially.

Food intake for 24 hours following the buffet meal was recorded in food diaries and energy intake was calculated with the aid of the Dietplan program (Forestfield Software LTD, West Sussex, UK).

Every 30 min subjects completed visual analogue scales (VAS) rating hunger, satiety, fullness, prospective food consumption and nausea. These consisted of 100 mm scales with the text expressing the most positive and the negative rating anchored at each end.

Study 2

The same protocol was followed as for Study 1, except that the eight healthy fasting volunteers were administered OXM subcutaneously at doses from 100 nmol to 250 nmol (in normal saline) thirty minutes before the buffet.

Results

Study 1

Figure 13:
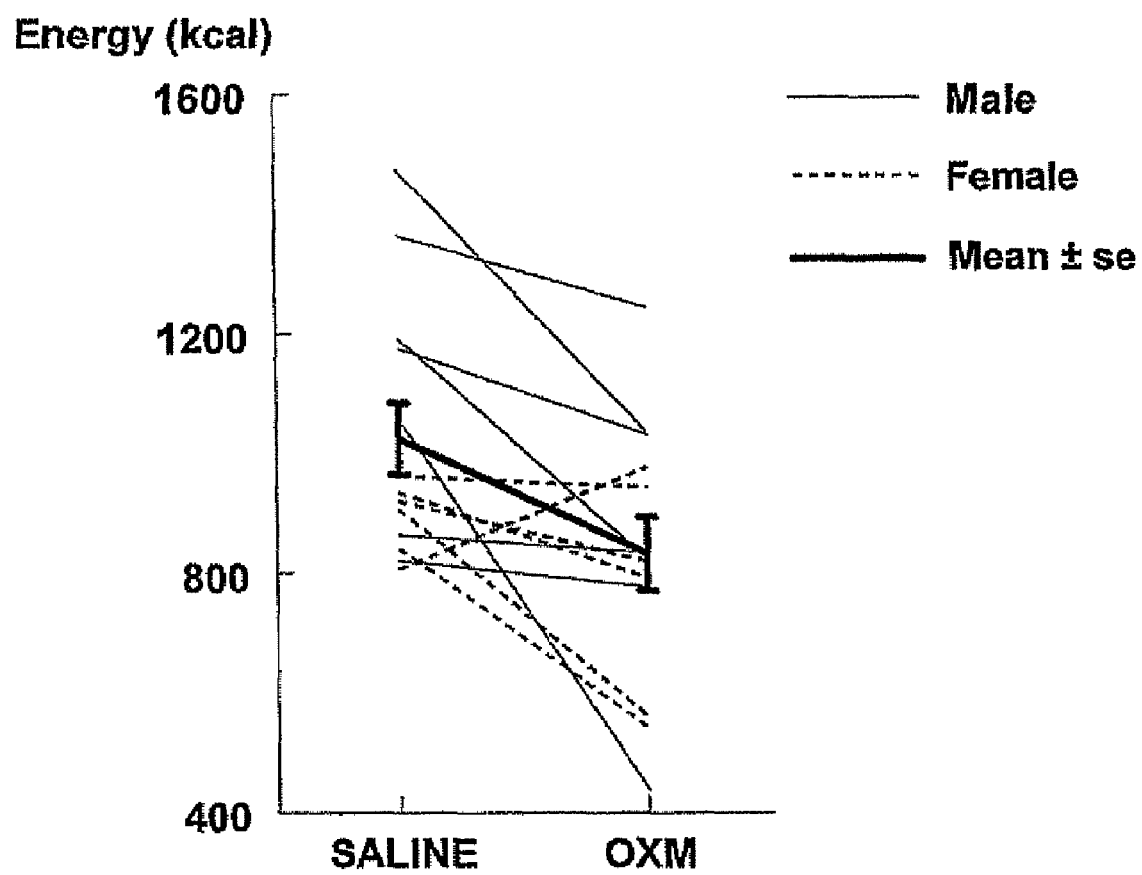
FIG. 13 shows the calories consumed by the human subject at the buffet meal. Each line represents the calories consumed by an individual subject with saline and OXM infusion. The bold line shows the mean calorie intake for all volunteers. The mean fall in calories with OXM infusion is 17.6±5.7%.
Figure 14:
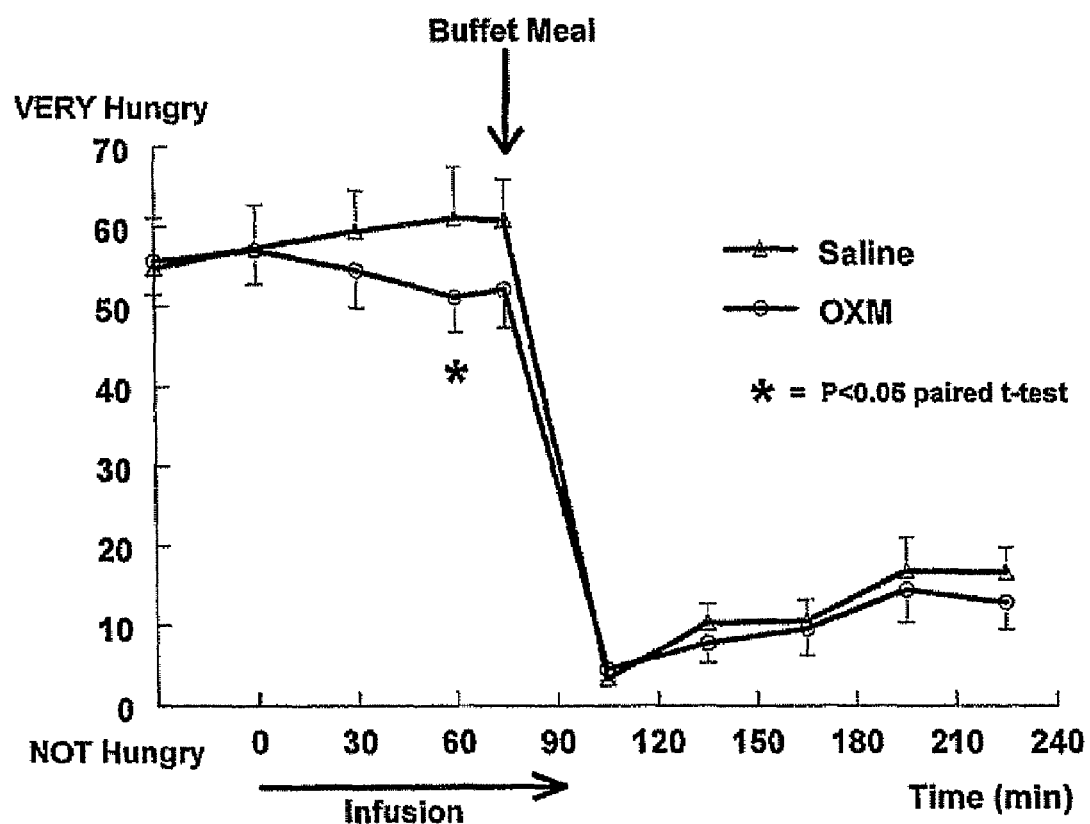
FIG. 14 is a visual analogue scale showing the response of the human subjects to the question 'How hungry are you right now?' There was a significant fall in subjective hunger during OXM infusion. Hunger scores diminished considerably following the buffet meal.

OXM infusion led to a significant fall in calories consumed at the buffet meal (192±59 kcal; 17.6±5.7%). 12/13 subjects showed a decrease in calories consumed with OXM infusion, see FIG. 13. OXM infusion was associated with a significant fall in subjective hunger scores, see FIG. 14 (VAS 'How hungry are you right now?' 60 min P<0.05). There were no adverse effects of OXM infusion. In particular there was no effect of OXM on feelings of sickness (nausea) (VAS 'How sick do you feel right now?' 75 min P=0.8). The effect appears to be rapid.

Study 2
The results obtained are shown in Table 4.

| Name | wt KG | BMI | nmol dose | nmol dose/kg | Energy (Kcal) saline | Energy (Kcal) sc oxm | Kcal Diff | Dif % |
|---|---|---|---|---|---|---|---|---|
| 01 | 89 | 27 | 100 | 1.12 | 1344 | 283 | −1061 | −79 |
| 02 | 95 | 28 | 100 | 1.05 | 1059 | 840 | −219 | −21 |
| 03 | 89 | 28 | 150 | 1.69 | 917 | 731 | −186 | −20 |
| 04 | 91 | 30 | 150 | 1.65 | 530 | 467 | −63 | −12 |
| 05 | 92 | 31 | 150 | 1.63 | 381 | 283 | −98 | −26 |
| 06 | 87 | 29 | 200 | 2.29 | 922 | 667 | −255 | −28 |
| 07 | 113 | 36 | 250 | 2.21 | 966 | 875 | −91 | −9 |
| 08 | 106 | 36 | 250 | 2.36 | 910 | 742 | −168 | −18 |
| | | | | MEAN | 879 | 611 | −268 | −32 |
| | | | | SEM | 106 | 84 | 116 | 12 |

Discussion

The demonstration that parenteral administration of OXM to human subjects results in a decrease in calories consumed and a significant reduction in subjective sensations of hunger without undesirable side effects, in particular, feelings of sickness (nausea) is confirmation the utility of OXM in the treatment or prevention of excess weight such as obesity in mammals, and as a novel target for the development of therapeutic agents in the treatment of excess weight such as obesity in mammals.

Example 4

Investigation of the Plasma OXM-Immunoreactivity (IR) and Ghrelin-Immunoreactivity IR (Ghrelin-IR) Levels Following IP Administration of OXM.

Methods

OXM or saline were administered to fasted rats to investigate the plasma OXM-IR and ghrelin-IR levels following IP OXM. Plasma OXM-IR levels were measured, using a previously described assay, which also measures enteroglucagon (i.e., N-terminally elongated OXM) (Ghatei M A, Uttenthal L O, Christofides N D, Bryant M G, Bloom S R 1983 J Clin Endocrinol Metab 57:488-495). The OXM-IR assay could detect changes of 10 pmol/L (95% confidence limit) with an intra-assay variation of 5.7%. The ghrelin radioimmunoassay (English P J, Ghatei M A, Malik I A, Bloom S R, Wilding J P 2002 J Clin Endocrinol Metab 87:2984) measured both octanoyl and des-octanoyl ghrelin (Total ghrelin). It did not cross-react with any known gastrointestinal or pancreatic peptide hormones and could detect changes of 10 pmol/L (95% confidence limit) with an intra-assay variation of 9.5%.

Rats (n=10 per group) were IP injected with OXM (30 nmoles/kg and 100 nmoles/kg) or saline at the beginning of the light phase. The rats were decapitated 30 and 90 minutes following the IP injection, trunk blood collected. All plasma was collected and frozen at −20 C until assayed for OXM-IR and ghrelin-IR. During the entire post-injection period the rats remained fasted. The time points and the doses of OXM were chosen by reference to previous feeding studies.

The release of gut hormones has been found to be influenced by the content of the diet, in particular the fat content. For this reason, a further three groups (n=10) were investigated: a) Rats fasted overnight and killed at the beginning of the light phase, b) Rats fed high fat rat chow (45% fat, Research Diets Inc.) overnight and decapitated at the beginning of the light phase, c) Rats fasted overnight and at lights-on, they were given ad libitum access to 45% high fat chow for 2 h. The rats were decapitated at the end of this 2-hour high fat meal (i.e., two hours into the light phase). All plasma was collected and frozen at −20° C. until assayed for OXM-IR and ghrelin-IR.

Results

IP administration of OXM (30 nmoles/kg and 100 nmoles/kg) increased plasma OXM-IR 30 and 90 minutes post-injection (30 min plasma OXM-IR pmol/L: saline 61.8±8.9, OXM 30 nmoles/kg 448.9±184.4, OXM 100 nmoles/kg 997.1±235.4. 90-min plasma OXM-IR pmol/L: saline 47.5±4.5, OXM 30 nmoles/kg 150.6±52.5 OXM 100 nmoles/kg 107.8±25.0).

The plasma OXM-IR levels were determined in three additional groups: a) Rats fasted overnight and killed at the beginning of the light phase (plasma OXM-IR pmol/L: 51.9±5.8), b) Rats fed high fat rat chow overnight and decapitated at the beginning of the light phase (plasma OXM-IR pmol/L: 220.2±22.2), c) Rats fasted overnight, then given ad libitum access to high fat chow for 2 hours at lights-on, were decapitated at the end of the 2-hour high fat meal (plasma OXM-IR pmol/L: 254.0±32.7).

Figure 15:
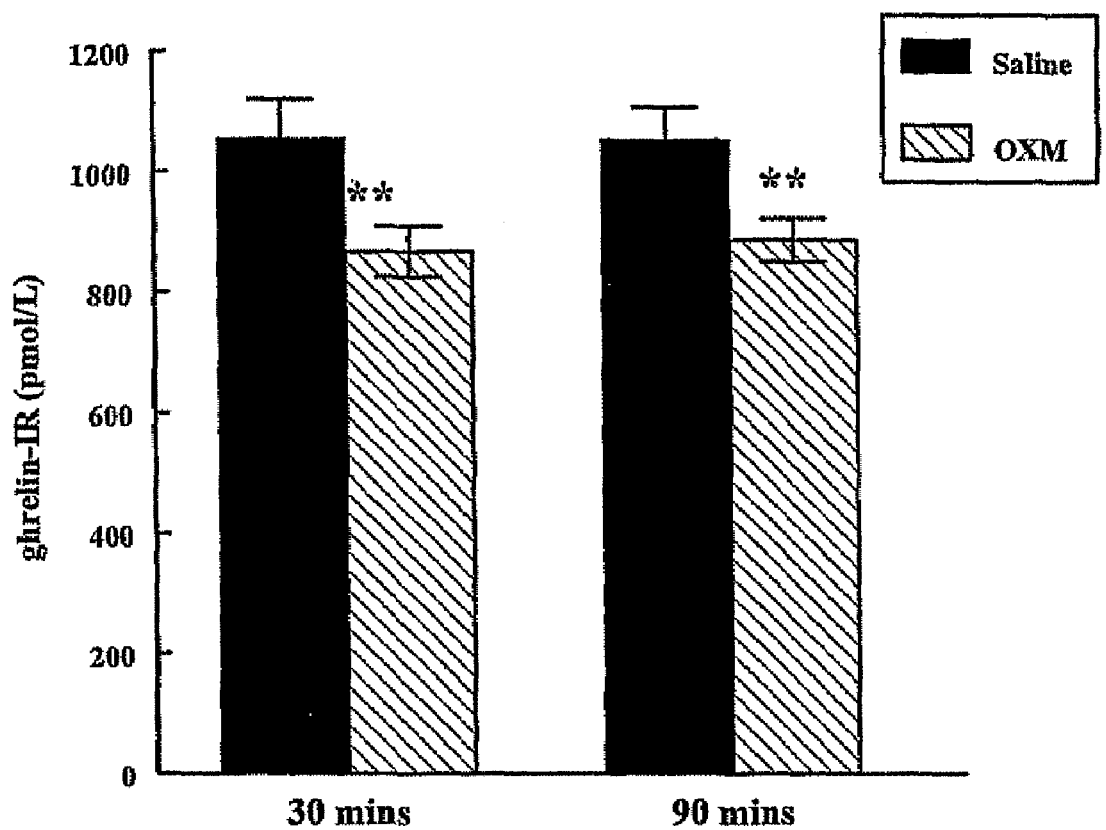
FIG. 15 shows the effect of IP administration of OXM (30 nmoles/kg and 100 nmoles/kg) on fasting plasma ghrelin-IR 30 and 90 minutes post-injection in rats. The solid blocks show the results with the saline control, the hatched block the results with OXM.
Figure 16:
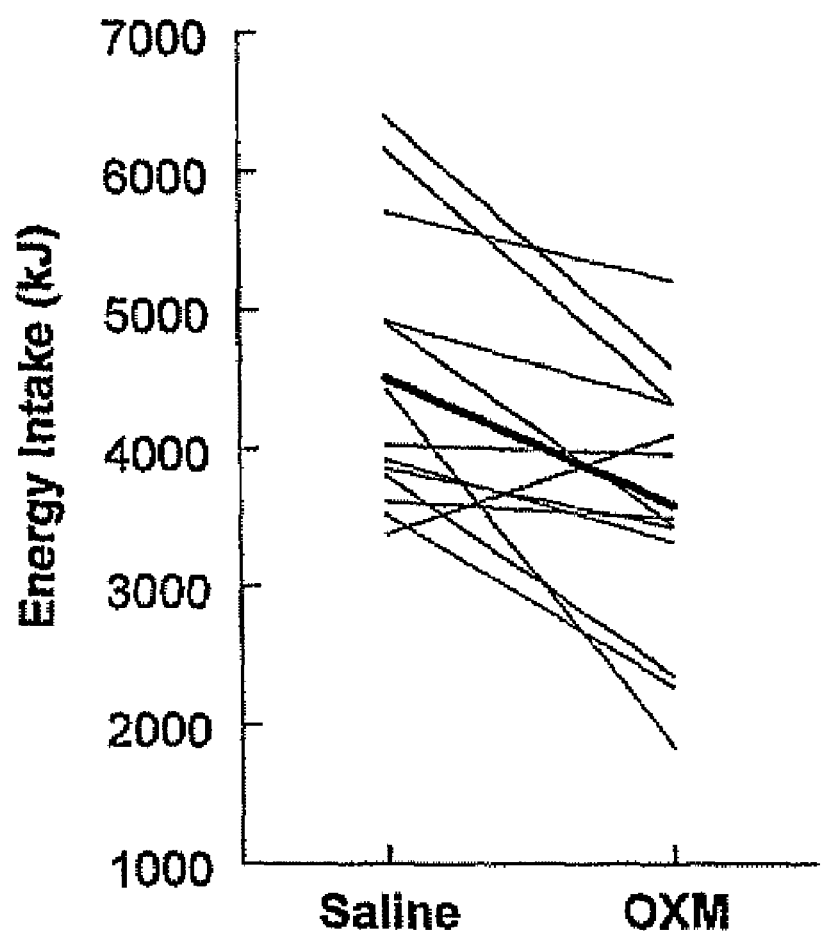
FIG. 16 shows energy intake in kJ calories consumed by human subjects at a buffet meal. Each line represents the energy intake of an individual subject with saline and with OXM infusion. The bold line shows the mean calorie intake for all volunteers.

IP administration of OXM (30 nmoles/kg and 100 nmoles/kg) significantly decreased fasting plasma ghrelin-IR 30 and 90 minutes post-injection (30 min plasma ghrelin pmol/L: saline, 1056.9±64.0, OXM, 30 nmoles/kg 867.4±42.0 ($p<0.01$), OXM, 100 nmoles/kg 860.0±47.5 ($p<0.02$). Ninety-minute plasma ghrelin-IR pmol/L: saline, 1055.2±52.5, OXM, 30 nmoles/kg 886.9±36.3 ($p<0.01$), OXM, 100 nmoles/kg 900.0±52.9 ($P<0.05$), see FIG. 15.

Plasma ghrelin-IR levels were determined in 3 additional groups: a) Rats fasted overnight and killed at the beginning of the light phase (plasma ghrelin-IR pmol/L: 1066.1±80.9), b) Rats fed high fat rat chow overnight and decapitated at the beginning of the light phase (plasma ghrelin-IR pmol/L: 611.3±16.9), c) Rats fasted overnight, at lights-on they were given ad libitum access to high fat chow for 2 h, were decapitated at the end of the 2-hour high fat meal (plasma ghrelin pmol/L: 648.9±57.3).

Example 5

Investigation of The Effect of OXM Infusion on Human Subjects

Methods

Study Design

The study design was as in Example 3. Subjects remained in the study room until $t_{225}$. They continued to complete VAS until 09:00 the following morning and recorded food intake in diaries for 24 hours following the buffet meal (until 13:00 the following day). Food diaries were analysed by a dietician blinded to the study and energy intake was calculated with the aid of the Dietplan program (Forestfield Software LTD, West Sussex, UK).

Plasma Hormone Measurements

All samples were assayed in duplicate and within one assay to eliminate inter-assay variation. Plasma OLI, pancreatic glucagon, peptide YY (PYY), insulin, glucagon-like peptide-1 (GLP-1) and ghrelin were measured using established in-house RIAs. The OLI assay (Ghatei M A, Uttenthal L O, Christofides N D, Bryant M G, Bloom S R 1983 J Clin Endocrinol Metab 57:488-495) could detect changes of 10 pmol/L (95% confidence limit) with an intra-assay variation of 5.7%. The PYY assay (Adrian T E, Savage A P, Sagor G R, Allen J M, Bacarese-Hamilton A J, Tatemoto K, Polak J M, Bloom S R 1985 Gastroenterology 89:494-499) could detect changes of 2 pmol/L (95% confidence limit) with an intra-assay variation of 5.8%. The PYY antibody was specific for the C-terminus of PYY and cross-reacts fully with human PYY 3-36. The insulin assay (Kreymann B, Williams G, Ghatei N M, Bloom S R 1987 Lancet 2:1300-1304) could detect changes of 6 pmol/L (95% confidence limit) with an intra-assay variation of 5.4%. The GLP-1 assay (Kreymann B, Williams G, Ghatei M A, Bloom S R 1987 Lancet 2:1300-1304) could detect changes of 8 pmol/L (95% confidence limit) with an intra-assay variation of 6.1%. The GLP-1 antibody was specific for amidated GLP-1 and does not cross-react with GLP-1 (1-37), GLP-1 (1-36) or GLP-1 (7-37). The ghrelin assay (English P J, Ghatei M A, Malik I A, Bloom S R, Wilding J P 2002 J Clin Endocrinol Metab 87:298) could detect changes of 10 pmol/L (95% confidence limit) with an intra-assay variation of 9.5%. Plasma leptin was measured using the Linco Research (Missouri, USA) human leptin RIA kit.

Results

1. Effects of OXM Infusion on Energy Intake

Figure 17:
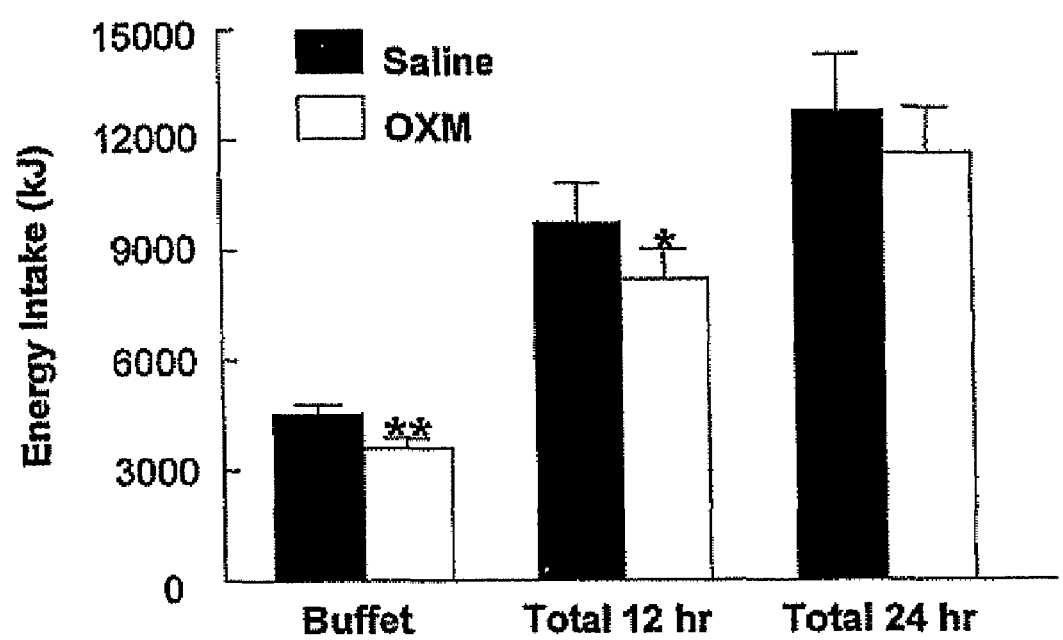
FIG. 17 shows the energy intake at the buffet meal, and the cumulative 12 and 24 hour energy intake of human subjects. The solid blocks show the results with the saline control, the hatched block the results with OXM.

OXM infusion significantly reduced energy intake at the buffet meal by 19.3±5.6% (reduction vs saline: 220±60 kcal, $P<0.01$). 12 out of the 13 subjects studied showed a decrease in energy intake with OXM infusion (FIG. 17). There was no obvious cause for the failure of response in one subject. OXM infusion significantly reduced cumulative 12 hour energy intake by 11.3±6.2% (reduction vs saline: 365±159 kcal, $P<0.05$) (FIG. 3). Cumulative 24 hour energy intake was not significantly altered (saline 3043±366 kcal, OXM 2768±297 kcal). OXM did not change water consumption or the proportion of calories obtained from different macronutrients at the buffet meal or in the subsequent cumulative 12 and 24 hr food intake.

2. Effects of OXM Infusion on Appetite and Palatability

Figure 18:
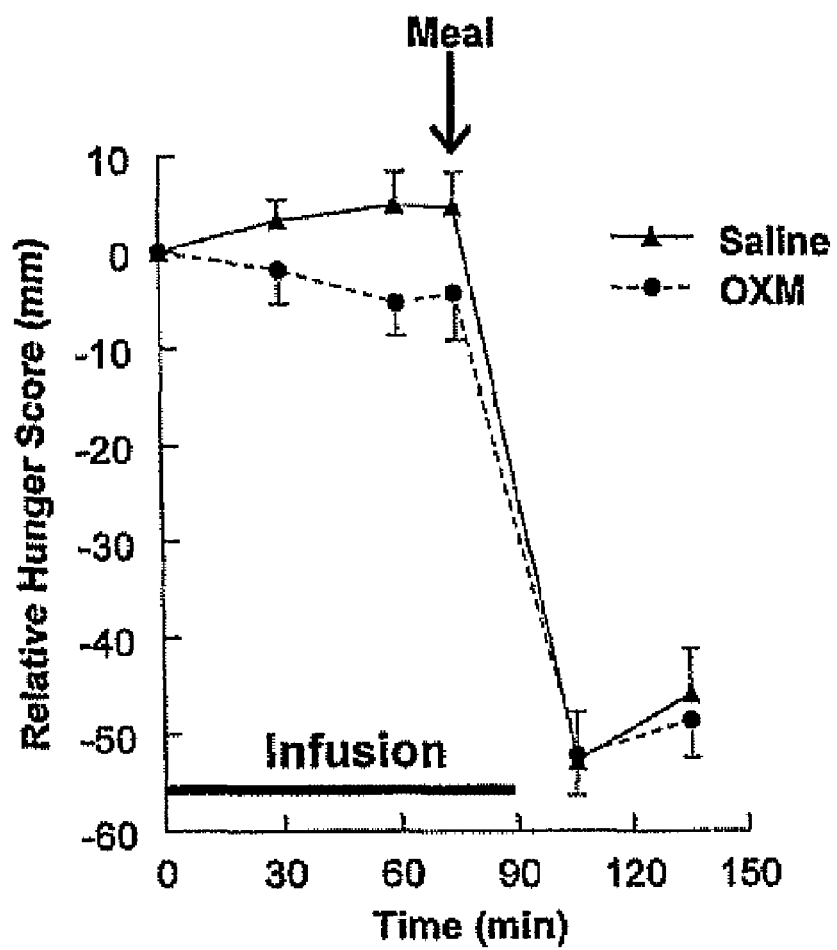
FIG. 18 shows the relative hunger scores of the human subjects during a fasting period and after a meal, with infusion of OXM or a saline control for the period shown.

During infusion of saline visual analogue scores for hunger did not change significantly throughout the fasting period (FIG. 18) whereas OXM infusion caused a significant fall in hunger (incremental AUC $t_0$ to $t_{75}$: saline+273±128 mm.min, OXM minus 374±185 mm.min, $P<0.05$). The decrease in hunger following the buffet meal was similar on saline and OXM infusion days and hunger scores remained similar thereafter. The duration of the meal was significantly reduced by OXM (saline 19.2±1.3 min, OXM 15.1±1.8 min, $P<0.05$). There was no significant effect of OXM on visual analogue scores for satiety, prospective food consumption, nausea and meal palatability (data not shown).

3. Plasma Levels of OXM-Like Immunoreactivity (OLI)

Figure 19:
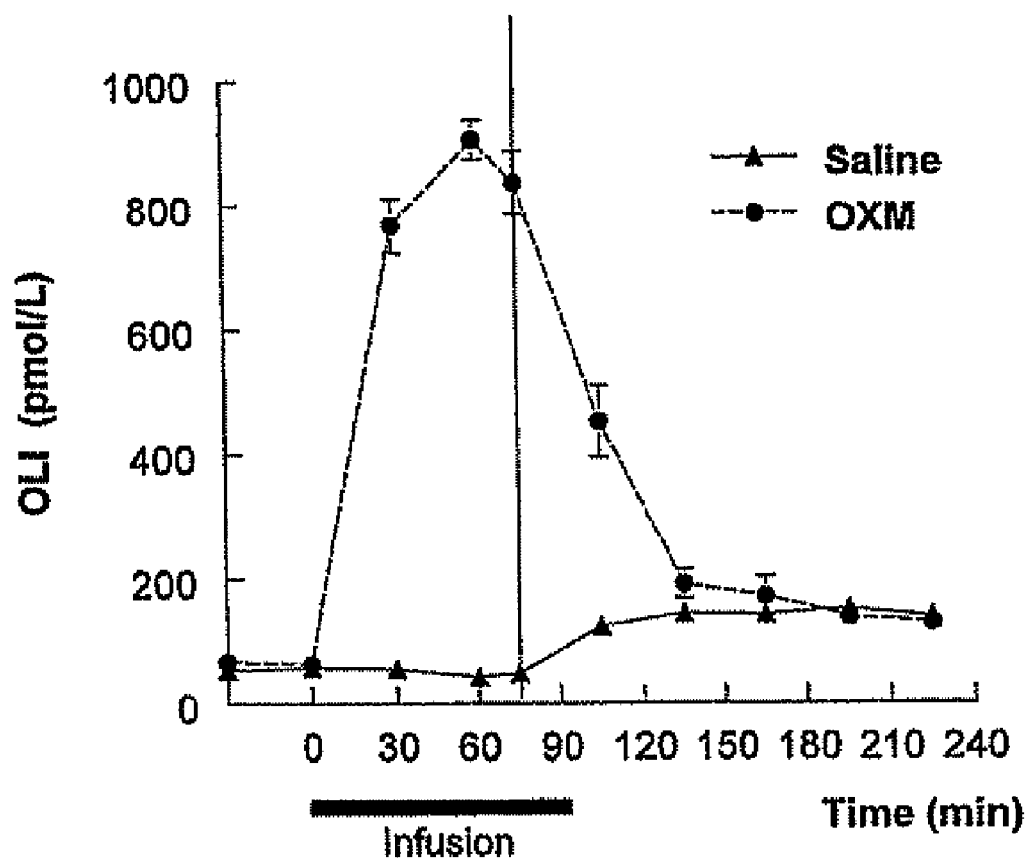
FIG. 19 shows the OXM-like immunoreactivity (OLI) in pmol/L determined by an RIA during a fasting period and after a meal, with infusion of OXM or a saline control for the period shown.
Figure 20:
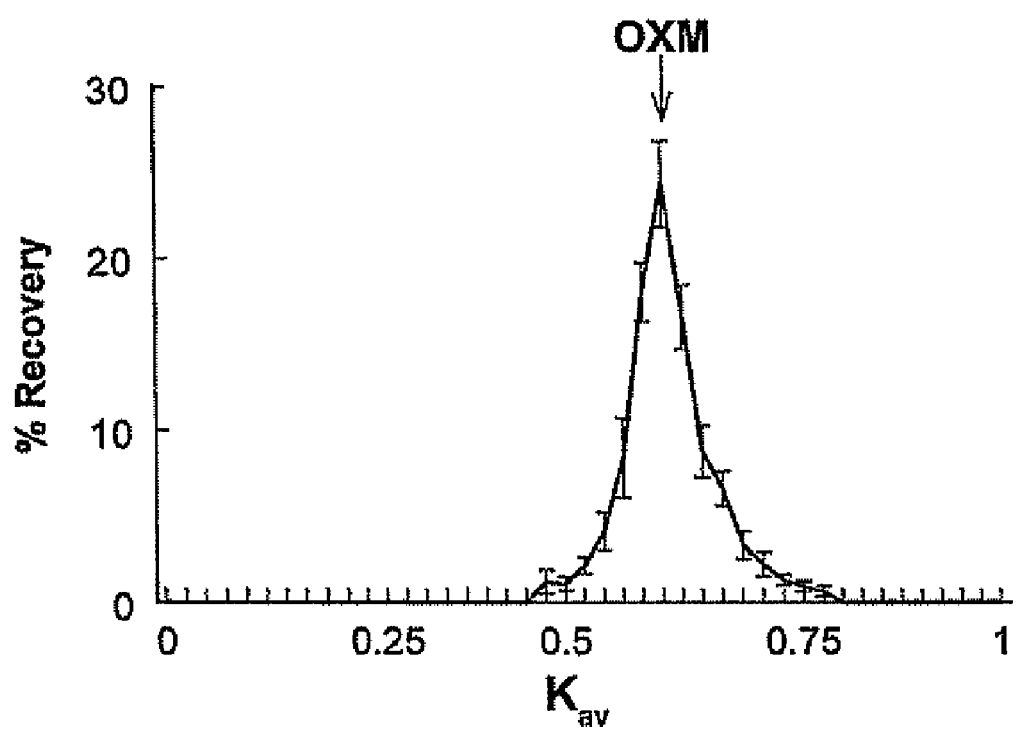
FIG. 20 shows gel permeation analysis of plasma samples during OXM infusion. The single immunoreactive peak elutes at the same position as synthetic OXM.

Infusion of OXM elevated plasma OLI from 62±5 pmol/L to a peak of 907±32 pmol/L at $t_{60}$ (FIG. 19). In comparison, on the saline infusion day, consumption of the buffet meal led to a peak postprandial OLI level of 151±18 pmol/L at 195 min. Gel permeation analysis of plasma samples during OXM infusion (FIG. 20) demonstrated a single immunoreactive peak elating in the same position as synthetic OXM ($K_{av}=0.6$). Thus intact full-length OXM was the principle circulating form.

4. Effects of OXM Infusion on Plasma Ghrelin

Figure 21:
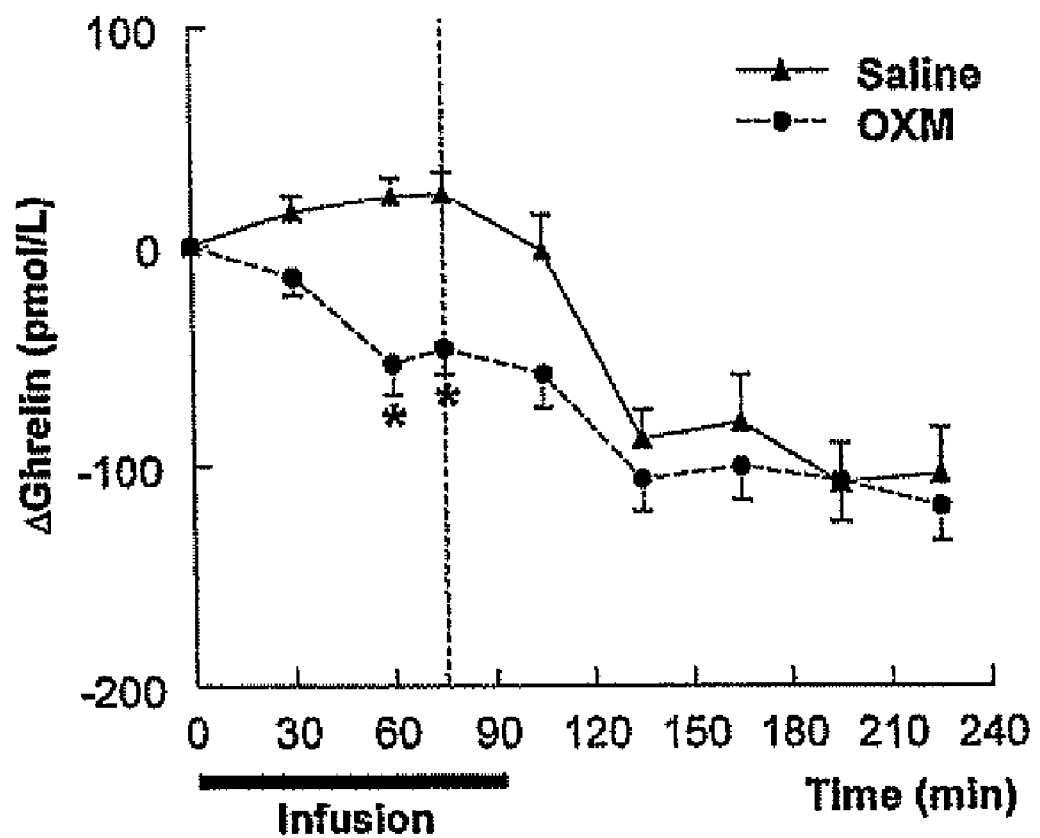
FIG. 21 shows the change in plasma ghrelin levels during a fasting period and after a meal, with infusion of OXM or a saline control for the period shown.

During the saline infusion, plasma ghrelin levels increased throughout the fasting period ($t_0$ 461±32 pmol/L, $t_{75}$ 484±35 pmol/L) and decreased postprandially ($t_{225}$ 357±28 pmol/L). However, during infusion of OXM fasting levels of ghrelin decreased before the meal ($t_0$ 482±33 pmol/L, $t_{75}$ 435±35 pmol/L) and there was a further postprandial reduction in ghrelin ($t_{225}$ 356±31 pmol/L). Hence plasma ghrelin prior to the buffet meal was significantly reduced by OXM infusion compared to saline (mean change in ghrelin from $t_0$ to $t_{75}$: saline+24±10 pmol/L, OXM minus 47±11 pmol/L, P<0.0001) (FIG. 21). The suppression in plasma ghrelin due to OXM infusion represents 44±10% of the postprandial decrease in ghrelin on the corresponding saline infusion day (mean postprandial decrease 155±19 pmol/L).

5. Effects of OXM Infusion on Plasma Hormones Levels

There was no significant effect of OXM infusion on fasting plasma levels of PYY, insulin, pancreatic glucagon, GLP-1 or leptin (table 1). Plasma concentrations of leptin in female subjects were higher than in males as has previously been reported.

Discussion

We have demonstrated that systemic administration of OXM significantly reduces food intake in healthy human subjects. Intravenous infusion of OXM reduced calorie intake by 19% at the buffet meal and cumulative energy intake was decreased in the 12 hours post-infusion. Much smaller alterations in food consumption would lead to weight loss if sustained in the long term. However there was no significant effect of OXM on cumulative 24 hour energy intake. Our work indicates that OXM may increase energy expenditure. OXM did not affect enjoyment of the meal, which is important in view of its potential therapeutic use.

Ghrelin is a powerful stimulant of appetite in man (Wren A M, Seal L J, Cohen M A, Brynes A S, Frost G S, Murphy K G, Dhillo W S, Ghatei M A, Bloom S R 2001 Ghrelin enhances appetite and increases food intake in humans. J Clin Endocrinol Metab 86:5992) and preprandial rises in plasma ghrelin have been suggested to be a trigger for meal initiation (Cummings D E, Purnell J Q, Frayo R S, Scbmidova K, Wisse B E, Weigle D S 2001 A preprandial rise in plasma ghrelin levels suggests a role in meal initiation in humans. Diabetes 50:1714-1719). Hence our novel finding that OXM infusion suppresses fasting plasma ghrelin is potentially important. Inhibition of the normal preprandial rise in ghrelin by OXM is likely to be one mechanism by which OXM infusion reduces appetite. This finding may also shed light on the poorly understood mechanism by which ghrelin levels are reduced postprandially. In rodents, fasting increases plasma ghrelin, while oral intake of glucose, but not water, decreases ghrelin secretion, suggesting that suppression of plasma ghrelin is related to ingestion of nutrients rather than stomach distension. Hence OXM released in response to nutrient ingestion may contribute to the normal postprandial inhibition of plasma ghrelin. It is believed that only a proportion of total circulating ghrelin is the biologically-active, octanoylated form. The effect of food consumption and OXM infusion may be to primarily reduce levels of this active ghrelin.

Intravenous infusion of OXM has been shown to inhibit gastric emptying in humans. Suppression of gastric-emptying may lead to increased gastric distension which may contribute to satiety by causing a sensation of fullness. In the current study hunger scores were significantly reduced by OXM in the fasting state when gastric distension is unlikely to be important. Hence the reduction in appetite in the pre-meal period is unlikely to result from effects of OXM on gastric emptying. The anorectic effect of OXM does not appear to be mediated by stimulation of the release of PYY or leptin as concentrations of these hormones were unaffected by OXM infusion.

We have demonstrated in humans the anorectic effect of elevated circulating levels of OXM. Infusion of OXM produced circulating levels of OLI which were comparable to the elevated concentrations seen in tropical sprue and following jejuno-ileal bypass surgery for morbid obesity. Therefore OXM may contribute to the loss of appetite and weight loss observed in these conditions. We consider that lower postprandial concentrations of OXM contribute to the physiological reduction of appetite in normal individuals and that exogenous administration of OXM has potential to reduce food intake and/or increase energy expenditure in the obese.

Taken together, these data demonstrate that OXM is potentially important in both long and short-term regulation of food intake, energy expenditure and body weight maintenance. Therefore, OXM may be useful in the treatment or prevention of excess weight such as obesity in mammals, and further represents a target for the development of therapeutic agents in the treatment of excess weight such as obesity in mammals, especially humans.

The invention claimed is:

1. A method for the prevention or treatment of excess weight in a subject mammal, which comprises administering oxyntomodulin and PYY to the subject.

2. The method according to claim 1, which is a method for the reduction or prevention of obesity.

3. The method according to claim 1, which comprises administering $PYY_{3-36}$.

4. The method according to claim 1, wherein the oxyntomodulin is administered via a route peripheral to the brain.

5. The method according to claim 1, wherein the PYY is administered via a route peripheral to the brain.

6. The method according to claim 4, wherein the oxyntomodulin is administered by a route selected from the group consisting of oral, rectal, intravenous, intramuscular, intraperitoneal, buccal, sublingual, nasal, subcutaneous, and transdermal administration.

7. The method according to claim 5, wherein the PYY is administered by a route selected from the group consisting of oral, rectal, intravenous, intramuscular, intraperitoneal, buccal sublingual, nasal, subcutaneous, and transdermal administration.

8. The method according to claim 1, wherein the oxyntomodulin is administered peripherally at a dose of 0.1 nmoles or more per kg body weight of the subject.

9. The method according to claim 1, wherein the oxyntomodulin is administered peripherally at a dose of up to 12 nmoles per kg body weight.

10. The method according to claim 1, wherein the oxyntomodulin is administered at a dose of 0.5 mg to 2 mg before meals.

11. The method according to claim 1, wherein the PYY is administered peripherally at a dose of 0.1 nmoles per kg body weight of the subject or more.

12. The method according to claim 1, wherein the PYY is administered peripherally at a dose of up to 3.2 nmoles per kg body weight.

13. The method according to claim 1, wherein the oxyntomodulin and the PYY are administered simultaneously, or sequentially in any order.

* * * * *

SEQUENCE LISTING

```
<160> NUMBER OF SEQ ID NOS: 9

<210> SEQ ID NO 1
<211> LENGTH: 37
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 2
<211> LENGTH: 36
<212> TYPE: PRT
<213> ORGANISM: Lophius piscatorius

<400> SEQUENCE: 2
```

His Ser Glu Gly Thr Phe Ser Asn Asp Tyr Ser Lys Tyr Leu Glu Asp
1               5                   10                  15

Arg Lys Ala Gln Glu Phe Val Arg Trp Leu Met Asn Asn Lys Arg Ser
            20                  25                  30

Gly Val Ala Glu
            35

<210> SEQ ID NO 3
<211> LENGTH: 36
<212> TYPE: PRT
<213> ORGANISM: Anguilla japonica

<400> SEQUENCE: 3

His Ser Gln Gly Thr Phe Thr Asn Asp Tyr Lys Tyr Leu Glu Thr
1               5                   10                  15

Arg Arg Ala Gln Asp Phe Val Gln Trp Leu Met Asn Ser Lys Arg Ser
            20                  25                  30

Gly Gly Pro Thr
            35

<210> SEQ ID NO 4
<211> LENGTH: 37
<212> TYPE: PRT
<213> ORGANISM: Homo sapiens

<400> SEQUENCE: 4

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
            35

<210> SEQ ID NO 5
<211> LENGTH: 36
<212> TYPE: PRT
<213> ORGANISM: Homo sapiens

<400> SEQUENCE: 5

His Asp Glu Phe Glu Arg His Ala Glu Gly Thr Phe Thr Ser Asp Val
1               5                   10                  15

Ser Ser Tyr Leu Glu Gly Gly Ala Ala Lys Glu Phe Ile Ala Trp Leu
            20                  25                  30

Val Lys Gly Arg
            35

<210> SEQ ID NO 6
<211> LENGTH: 31
<212> TYPE: PRT
<213> ORGANISM: Homo sapiens

<400> SEQUENCE: 6

His Ala Glu Gly Thr Phe Thr Ser Asp Val Ser Ser Tyr Leu Glu Gly
1               5                   10                  15

Gly Ala Ala Lys Glu Phe Ile Ala Trp Leu Val Lys Gly Arg Gly
            20                  25                  30

<210> SEQ ID NO 7
<211> LENGTH: 30
<212> TYPE: PRT

```
<213> ORGANISM: Homo sapiens

<400> SEQUENCE: 7

His Ala Glu Gly Thr Phe Thr Ser Asp Val Ser Ser Tyr Leu Glu Gly
1               5                   10                  15

Gly Ala Ala Lys Glu Phe Ile Ala Trp Leu Val Lys Gly Arg
            20                  25                  30

<210> SEQ ID NO 8
<211> LENGTH: 36
<212> TYPE: PRT
<213> ORGANISM: Homo sapiens

<400> SEQUENCE: 8

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 9
<211> LENGTH: 37
<212> TYPE: PRT
<213> ORGANISM: Homo sapiens

<400> SEQUENCE: 9

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```